United States Patent [19]

Branca et al.

[11] Patent Number: 5,140,011
[45] Date of Patent: Aug. 18, 1992

[54] AMINO ACID DERIVATIVES WHICH HAVE RENIN INHIBITING ACTIVITY

[75] Inventors: Quirico Branca; Hans P. Märki, both of Basel, Switzerland; Werner Neidhart, Freiburg im Breisgau, Fed. Rep. of Germany; Henri Ramuz, Birsfelden, Switzerland; Wolfgang Wostl, Grenzach-Wyhlen, Fed. Rep. of Germany

[73] Assignee: Hoffmann-La Roche, Inc., Nutley, N.J.

[21] Appl. No.: 501,694

[22] Filed: Mar. 29, 1990

[30] Foreign Application Priority Data

Apr. 5, 1989 [CH] Switzerland .................. 1290/89

[51] Int. Cl.$^5$ ................ A61K 37/02; C07K 1/00; C07K 5/06; C07K 5/08
[52] U.S. Cl. ......................... 514/18; 514/19; 530/331; 548/215; 548/218; 549/321; 549/322; 562/443; 562/445; 562/448; 564/153
[58] Field of Search ............... 514/18, 19, 929; 530/330, 331; 548/215, 218; 549/321, 322; 562/443, 445, 448, 561, 567; 564/152, 153, 197, 199, 204

[56] References Cited

U.S. PATENT DOCUMENTS

| | | | |
|---|---|---|---|
| 4,613,676 | 9/1986 | Fuhrer et al. | 930/10 |
| 4,652,551 | 3/1987 | Luby et al. | 514/18 |
| 4,713,445 | 12/1987 | Szelke et al. | 530/330 |
| 4,727,060 | 2/1988 | Buhlmayer et al. | 514/18 |
| 4,758,584 | 7/1988 | Bühlmayer et al. | 514/18 |
| 4,851,387 | 7/1989 | Kaike et al. | 530/331 |
| 4,880,781 | 11/1989 | Hester, Jr. et al. | 530/331 |

FOREIGN PATENT DOCUMENTS 0310918  4/1989  European Pat. Off. .............. 514/18

OTHER PUBLICATIONS

Buhlmayer et al, "Synthesis and Biological Activity of Some Transition-State Inhibitors of Human Renin", *J. Med. Chem*, vol. 31, No. 9, 1988, pp. 1839–1846.
Luly et al, "Resin Inhibitors. Dipeptide Analogues of Angiotensin Utilizing . . . ", J. Med. Chem, vol. 31, No. 12, 1988, pp. 2264–2276.
Burger, *Medicinal Chemistry*, 1960, pp. 565–571, 578–581, 600–601.
Plattner et al. *J. Med. Chem.* 1988, 31(12):2277–2288.
Bolis et al. *J. Med. Chem.* 1987, 30(10):1729–1737.
Haber et al. *J. Cardiovasc. Pharmacol.* 1987, 10(Suppl. 7):554–558.

*Primary Examiner*—Jeffrey E. Russel
*Attorney, Agent, or Firm*—George M. Gould; William H. Epstein; Bruce A. Pokras

[57] ABSTRACT

The compounds of the formula

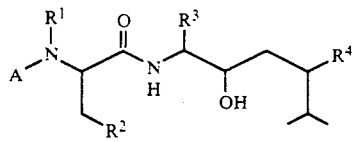

I wherein A, $R^1$, $R^2$, $R^3$ and $R^4$ have the significance given in claim 1, in the form of optically pure diastereomers, mixtures of diastereomers, diastereomeric racemates or mixtures of diastereomeric racemates as well as pharmaceutically usable salts thereof inhibit the activity of the natural enzyme renin and can accordingly be used in the form of pharmaceutical preparations in the control or prevention of high blood pressure and cardiac insufficiency.

21 Claims, No Drawings

AMINO ACID DERIVATIVES WHICH HAVE RENIN INHIBITING ACTIVITY

FIELD OF THE INVENTION

The present invention relates to amino acid derivatives.

SUMMARY OF THE INVENTION

The present invention relates to amino acid derivatives. In particular, it is concerned with amino acid derivatives of the general formula

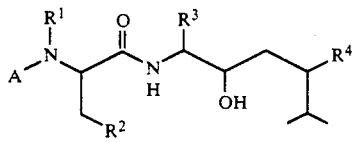

wherein $R^1$ signifies hydrogen or methyl, $R^2$ signifies ethyl, propyl, isopropyl, imidazol-2-yl, imidazol-4-yl, pyrazol-3-yl, thiazol-4-yl, thien-2-yl, ethoxycarbonyl, t-butylcarbonylmethyl, benzyloxycarbonylmethyl or t-butoxy, $R^3$ signifies isobutyl, cyclohexylmethyl or benzyl. A signifies one of the groups

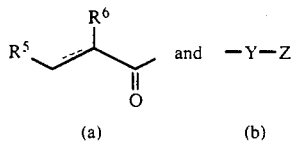

and $R^4$ signifies alkanoyl, arylcarbonyl, 2,2-dialkylvinyl or one of the groups

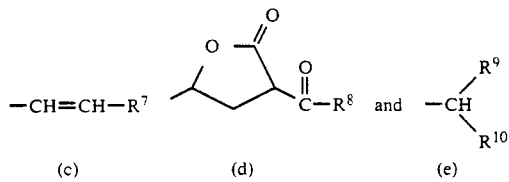

in which the dotted line can signify an additional bond, $R^5$ signifies phenyl, substituted phenyl, benzyl or naphthyl and $R^6$ signifies hydrogen, alkoxycarbonylalkyl, alkylcarbonylalkyl, cycloalkylcarbonylalkyl, heterocycloalkylcarbonylalkyl, arylcarbonylalkyl, aminocarbonylalkyl, substituted aminocarbonylalkyl, aminoalkylcarbonylalkyl, substituted aminoalkylcarbonylalkyl, aminoalkylsulphonylalkyl, substituted aminoalkylsulphonylalkyl, alkoxycarbonylhydroxyalkyl, alkylcarbonylhydroxyalkyl, cycloalkylcarbonylhydroxyalkyl, heterocycloalkylcarbonylhydroxyalkyl, arylcarbonylhydroxyalkyl, aminocarbonylhydroxyalkyl, substituted aminocarbonylhydroxyalkyl, dialkoxyphosphoroxyalkyl, diphenyloxyphosphoroxyalkyl, arylalkyl, alkoxycarbonylamino, arylalkoxycarbonylamino, alkylthioalkyl, alkylsulphinylalkyl, alkylsulphonylalkyl, arylthioalkyl, arylsulphinylalkyl, arylsulphonylalkyl, arylalkylthioalkyl, arylalkylsulphinylalkyl or arylalkylsulphonylalkyl, with the proviso that $R^6$ can not signify alkoxycarbonylamino or arylalkoxycarbonylamino when $R^5$ signifies phenyl, benzyl or α-naphthyl, Y signifies the bivalent residue of optionally N- and/or α-methylated phenylglycine, cyclohexylglycine, phenylalanine, cyclohexylalanine, 4-fluorophenylalanine, 4-chlorophenylalanine, tyrosine, O-methyltyrosine, α-naphthylalanine or homophenylalanine linked with Z at the N-terminal, Z signifies acyl, $R^7$ signifies alkyl, aryl, heteroaryl, alkylaminocarbonyl, arylalkylaminocarbonyl or heteroarylalkylaminocarbonyl, $R^8$ signifies alkoxy, $R^9$ signifies hydrogen or hydroxy and $R^{10}$ signifies azidomethyl, group (c) or one of the groups

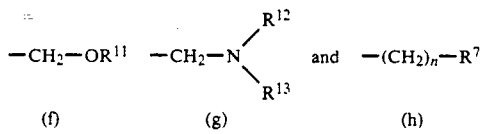

in which $R^{11}$ signifies hydrogen, alkyl, arylalkyl, aryl, alkanoyl, arylalkylcarbonyl, heteroarylalkylcarbonyl or alkylcarbamoyl, $R^{12}$ and $R^{13}$ each independently signify hydrogen, alkyl, arylalkyl, heteroarylalkyl, aryl, alkanoyl, alkoxycarbonyl, arylalkylcarbonyl, arylalkoxycarbonyl, heteroarylalkylcarbonyl, heterocycloalkylcarbonyl, alkylcarbamoyl or the group

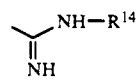

or $R^{12}$ and $R^{13}$ together with the nitrogen atom to which they are attached signify a 5- or 6-membered heterocycle or optionally substituted benzimidazolonyl, n signifies 0, 1 or 2 and $R^{14}$ signifies hydrogen or arylalkoxycarbonyl, in the form of optically pure diastereomers, mixtures of diastereomers, diastereomeric racemates or mixtures of diastereomeric racemates as well as pharmaceutically usable salts of these compounds.

These compounds are novel and are distinguished by valuable pharmacodynamic properties.

Objects of the present invention are the compounds of formula I and their pharmaceutically usable salts per se and for use as therapeutically active substances, the manufacture of these compounds, medicaments containing these and the manufacture of such medicaments, as well as the use of compounds of formula I and their pharmaceutically usable salts in the control or prevention of illnesses or in the improvement of health, especially in the control or prevention of high blood pressure and cardiac insufficiency.

DETAILED DESCRIPTION OF THE INVENTION

The following definitions of the general terms used in the present description apply irrespective of whether the terms in question appear alone or in combination.

The term "alkyl" used in the present description signifies straight-chain and branched, saturated hydrocarbon residues with 1-8, preferably 1-4, carbon atoms such as methyl, ethyl, n-propyl, isopropyl, n-butyl, isobutyl, sec.-butyl, t-butyl, pentyl, hexyl and the like. The term "alkoxy" signifies alkyl ether groups in which the term "alkyl" has the above significance, such as methoxy, ethoxy, propoxy, isopropoxy, butoxy, isobutoxy, sec.-butoxy, t-butoxy and the like. The term "cycloalkyl" signifies saturated, cyclic hydrocarbon residues with 3-8, preferably 3-6, carbon atoms such as cyclopropyl, cyclobutyl, cyclopentyl, cyclohexyl and the like. The term "heterocycloalkyl" relates in the same manner to saturated, 5-8-membered, preferably 5- or 6-membered, cyclic hydrocarbon residues in which one or two methylene groups is/are replaced by one or two oxygen, sulphur or optionally, alkyl-, phenylalkyl-, alkanoyl- or alkanoyloxy-substituted nitrogen atoms, such as piperidinyl, pyrazinyl, N-benzylpyrazinyl, morpholinyl, N-methylpiperidinyl, N-benzylmorpholinyl and the like. The term "alkanoyl" signifies the acid residue of a straight-chain or branched alkanoic acid with 1-8, preferably 1-4, carbon atoms such as formyl, acetyl, propionyl, butyryl, valeryl, isovaleryl and the like. The term "aryl" denotes a mono- or bicyclic aromatic hydrocarbon residue with 6-14 carbon atoms which is optionally mono- or multiply-substituted by alkyl, alkoxy, alkanoyloxy, amino, alkylamino, dialkylamino, alkylcarbonylamino, hydroxy, halogen, trifluoromethyl or nitro, such as phenyl, α- or β-naphthyl, indenyl, anthryl or phenanthryl and the like. The term "arylalkyl" denotes straight-chain or branched alkyl groups in which one or more hydrogen atoms is/are replaced by aryl groups, such as benzyl, diphenylmethyl, trityl, α- or β-naphthylmethyl, 2-phenylethyl, 3-phenyl-2-propyl, 4-phenyl-3-butyl, 2-(α- or β-naphthyl)ethyl, 3-α-naphthyl-2-propyl, 4-α-naphthyl-3-butyl and the like, whereby the aromatic residue in each case can be mono- or multiply-substituted as indicated above. The term "substituted phenyl" denotes phenyl which is optionally mono- or multiply-substituted by alkyl, alkoxy, alkoxyalkoxy, alkanoyl, alkanoyloxy, hydroxy, halogen or trifluoromethyl, such as 4-hydroxyphenyl, 4-methoxyphenyl, 4-methylphenyl, 4-chlorophenyl, 4-ethoxyethoxyphenyl and the like. Examples of optionally substituted benzimidazolonyl are benzimidazolonyl, 3-methylbenzimidazolonyl, 3-isopropylbenzimidazolonyl, 3-butylbenzimidazolonyl, 3-morpholinoethylbenzimidazolonyl, 3-benzylbenzimidazonyl and the like. The term "5- or 6-membered heterocycle" relates to saturated 5- or 6-membered heterocycles with at least one nitrogen atom and optionally an additional oxygen, nitrogen or sulphur atom as the ring member(s), which can be substituted on the second nitrogen atom by alkyl, phenyl, phenylalkyl or hydroxyalkyl or on a carbon atom by alkylamine, arylalkylamine, alkyl, phenyl or phenylalkyl, such as piperidinyl, 4-benzylaminopiperidinyl, pyrazinyl, piperazinyl, N-hydroxyethylpiperazinyl, morpholinyl, thiomorpholinyl, pyrrolidinyl, thiazolidinyl, imidazolidinyl, oxazolidinyl and the like. The term "heteroaryl" denotes a mono- or bicyclic aromatic hydrocarbon residue in which one or more carbon atoms is/are replaced by one to two nitrogen atoms and/or an oxygen or sulphur atom and which is optionally substituted on a nitrogen atom by alkyl, phenyl or phenylalkyl and/or on one or more carbon atoms by alkyl, phenyl, phenylalkyl, halogen, hydroxy, alkoxy, phenylalkoxy or oxo and which can be partially saturated, such as pyrrolyl, furyl, thienyl, imidazolyl, pyrazolyl, oxazolyl, thiazolyl, pyridyl, pyrazinyl, pyrimidinyl, indolyl, quinolyl, isoquinolyl or quinoxalinyl, e.g. 2- or 3-pyrrolyl, phenylpyrrolyl, e.g. 4- or 5-phenyl-2-pyrrolyl, 2-furyl, 2-thienyl, 2-imidazolyl, 2-, 3- or 4-pyridyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2-indolyl, 1-benzyl-3-indolyl, 4,5,6,7-tetrahydro-2-indolyl, 2-, 3- or 4-quinolyl, 4-hydroxy-2-quinolyl, 1-, 3- or 4-isoquinolyl, 1-oxo-1,2-dihydro-3-isoquinolyl, 2-quinoxalinyl, 2-benzofuranyl, 2-benzoxazolyl, 2-benzthiazolyl, 2-benzimidazolyl and the like.

The term "halogen" relates to the four halogens fluorine, chlorine, bromine and iodine.

The term "substituted amino" signifies an amino group which is mono- or di-substituted by alkyl, arylalkyl, alkanoyl, alkoxycarbonyl or arylalkoxycarbonyl or an amino group which is disubstituted by $C_3$-$C_6$-alkylene which is optionally interrupted by an oxygen, sulphur or optionally alkyl-, phenylalkyl-, alkanoyl- or alkanoyloxy-substituted nitrogen atom. The term "acyl" relates to the acyl group of a carboxylic acid, of a half ester of carbonic acid, of an optionally N-substituted carbamic or thiocarbamic acid, of an optionally N-substituted oxalamide, of a sulphonic acid or of an optionally N-substituted amidosulphonic acid, especially those with the partial formulae $R^b$—CO—, $R^a$—O—CO—, $(R^b)(R^b)$N—CO—, $(R^b)(R^b)$N—CS—, $(R^b)(R^b)$N—CO—CO—, $R^b$—SO$_2$— or $(R^b)(R^b)$N—SO$_2$—, in which $R^a$ signifies an unsubstituted or substituted, saturated or unsaturated aliphatic, cycloaliphatic, cycloaliphatic-aliphatic hydrocarbon residue with up to 18, preferably 10, carbon atoms which is optionally functionalized with amino, monoalkylamino, dialkylamino, alkanoylamino or alkanoyloxyamino, an unsubstituted or substituted aromatic, heteroaromatic, aromatic-aliphatic or heteroaromatic-aliphatic hydrocarbon residue with up to 18, preferably 10, carbon atoms or an unsubstituted or substituted, saturated 5- or 6-membered heterocyclic residue and $R^b$ signifies hydrogen or has the significance of $R^a$. The term "acyl" also relates to the monovalent residue of an acylated amino acid or of an acylated dipeptide attached via the carboxyl group.

An unsubstituted or substituted, saturated or unsaturated, aliphatic, cycloaliphatic or cycloaliphatic-aliphatic hydrocarbon residue $R^a$ or $R^b$ is, for example, unsubstituted or substituted alkyl, alkenyl, alkynyl, mono-, bi- or tricycloalkyl, monocycloalkenyl, bicycloalkenyl, cycloalkylalkyl, cycloalkylalkenyl or cycloalkenylalkyl. "Substituted alkyl" signifies an alkyl residue in which one or more hydrogen atoms can be substituted by hydroxy, alkoxy, aryloxy, alkanoyloxy, halogen, hydroxysulphonyloxy, carboxy, alkoxycarbonyl, carbamoyl, alkylcarbamoyl, dialkylcarbamoyl, cyano, phosphono, esterified phosphono, amino or oxo, whereby the substituents are present in the 1-position of the alkyl residue only when this is attached to the carbonyl group in the partial formula $R^b$—CO—.

Examples of substituted alkyl are 2-hydroxyethyl, methoxymethyl, 2-methoxyethyl, phenoxymethyl, α- or β-naphthoxymethyl, acetoxymethyl, 2-acetoxymethyl, 2-acetoxyethyl, chloromethyl, bromomethyl, 2-chloro- or 2-bromoethyl, hydroxysulphonyloxymethyl, 2-hydroxysulphonyloxyethyl, carboxymethyl, 2-carboxyethyl, methoxycarbonylmethyl, 2-methoxycarbonylethyl, ethoxycarbonylmethyl, 2-ethoxycarbonylethyl, carbamoylmethyl, 2-carbamoylethyl, methylcarbamoylmethyl, dimethylcarbamoylmethyl, cyanomethyl, 2-cyanoethyl, 2-oxopropyl, 2-oxobutyl, hydroxycarboxymethyl, 1-hydroxy-2-carboxyethyl, hydroxyethoxycarbonylethyl, hydroxymethoxycarbonylethyl, acetoxymethoxycarbonylmethyl, 1,2-dihydroxy-2-carboxyethyl, 1,2-dihydroxy-2-ethoxycarbonylethyl, 1,2-dihydroxy-2-methoxycarbonylethyl, 1,2-diacetoxy-2-ethoxycarbonylethyl, 1,2-diacetoxy-2-methoxycarbonylethyl, 1-α-naphthoxy-3-carboxypropyl, 1-α-naphthoxy-2-ethoxycarbonylethyl, 1-α-naphthoxy-3-t-butoxycarbonylpropyl, 1-α-naphthoxy-2-benzyloxycarbonylethyl, 1-α-naphthoxy-3-carbamoylpropyl, α-naphthoxycyanomethyl, 1-α-naphthoxy-3-cyanopropyl. 1-α-naphthoxy-4-dimethylaminobutyl or 1-α-naphthoxy-3-oxobutyl.

The term "alkenyl" relates to straight-chain or branched, unsaturated hydrocarbon residues with 2-8, preferably 2-4, carbon atoms, whereby the double bond is present in the 1-position of the alkenyl residue only when this is attached to the carbonyl group in the partial formula $R^b$—CO—. Examples of such alkenyl residues are vinyl, allyl, 2-butenyl or 3-butenyl. The alkenyl residues can be substituted by the same substituents as the alkyl residues.

The term "alkynyl" relates to hydrocarbon residues with 2-8, preferably 2-4, carbon atoms which contain a triple bond, such as ethynyl, 1-propynyl or 2-propynyl. The term "bicycloalkyl" relates to bicyclic saturated hydrocarbon residues with 5-10, preferably 6-9, carbon atoms such as bicyclo[3.1.0]hex-1-yl, bicyclo[3.1.0]hex-2-yl, bicyclo[3.1.0]hex-3-yl, bicyclo[4.1.0]hept-1-yl, bicyclo[4.1.0]hept-4-yl, bicyclo[2.2.1]hept-2-yl, bicyclo[3,2,1]oct-2-yl, bicyclo[3.3.0]oct-3-yl, bicyclo[3.3.1]-non-9-yl, α- or β-decahydronaphthyl and the like.

The term "tricycloalkyl" relates to a tricyclic saturated hydrocarbon residue with 8-10 carbon atoms such as 1-adamantyl.

The term "cycloalkenyl" relates to an unsaturated cyclic hydrocarbon residue with 3-8, preferably 3-6, carbon atoms such as 1-cyclohexenyl, 1,4-cyclohexadienyl and the like.

The term "bicycloalkenyl" relates to a bicyclic unsaturated hydrocarbon residue with 5-10, preferably 7-10, carbon atoms such as 5-norbornen-2-yl, bicyclo[2.2.2]octen-2-yl, hexahydro-4,7-methanoind-1-en-6-yl and the like.

Cyclopropylmethyl, cyclobutylmethyl, cyclopentylmethyl, cyclohexylmethyl and the like are examples of cycloalkylalkyl. Cyclohexylvinyl and cyclohexylallyl and the like can be named as examples of cycloalkylalkenyl. 1-Cyclohexenylmethyl, 1,4-cyclohexadienylmethyl and the like are examples of cycloalkenylalkyl.

The mentioned cycloaliphatic and cycloaliphatic-aliphatic residues can be substituted by the same substituents as alkyl.

An optionally substituted aromatic or aromatic-aliphatic hydrocarbon residue is, for example, unsubstituted or substituted aryl, arylalkyl or arylalkenyl. Styryl, 3-phenylallyl, 2-(α-naphthyl)vinyl, 2-(β-naphthyl)vinyl and the like are examples of arylalkenyl.

In a heteroaromatic or heteroaromatic-aliphatic hydrocarbon residue the heterocycle is mono-, bi- or tricyclic and contains one or two nitrogen atoms and/or an oxygen or sulphur atom and is linked with the group —CO—, —O—CO—, >N—CO—, >N—CS—, >N—CO—CO—, —SO₂ or >N—SO₂— with one of its ring carbon atoms. Examples of such heteroaromatic hydrocarbon residues are pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl or a benz-fused, cyclopenta-, cyclohexa- or cyclohepta-fused derivative of these residues. The heteroaromatic residue can be substituted on a nitrogen atom by alkyl, phenyl or phenylalkyl, e.g. benzyl, and/or on one or more carbon atoms by alkyl, phenyl, phenylalkyl, halogen, hydroxy, alkoxy, phenylalkoxy or oxo and can be partially saturated. Examples of such heteroaromatic residues are 2- or 3-pyrrolyl, phenylpyrrolyl, e.g. 4- or 5-phenyl-2-pyrrolyl, 2-furyl, 2-thienyl, 2-imidazolyl, 2-, 3- or 4-pyridyl, 2-, 3- or 5-indolyl, substituted 2-indolyl, for example 1-methyl-, 5-methyl-, 5-methoxy-, 5-benzyloxy-, 5-chloro- or 4,5-dimethyl-2indolyl, 1-benzyl-2-indolyl, 1-benzyl-3-indolyl, 4,5,6,7-tetrahydro-2-indolyl, cyclohepta[b]-5-pyrrolyl, 2-, 3- or 4-quinolyl, 4-hydroxy-2-quinolyl, 1-, 3- or 4-isoquinolyl, 1-oxo-1,2-dihydro-3-isoquinolyl, 2-quinoxalinyl, 2-benzofuranyl, 2-benzoxazolyl, 2-benzthiazolyl, benz[e]indol-2-yl, β-carbolin-3-yl and the like.

Examples of heteroaromatic-aliphatic hydrocarbon residues are 2- or 3-pyrrolylmethyl, 2-, 3- or 4-pyridylmethyl, 2-(2-, 3- or 4-pyridyl)ethyl, 4-imidazolylmethyl, 2-(4-imidazolyl)ethyl, 2-indolylmethyl, 3-indolylmethyl, 2-(3-indolyl)ethyl, 2-quinolylmethyl and the like.

A saturated 5- or 6-membered heterocyclic residue has at least one carbon atom, 1-3 nitrogen atoms and optionally an oxygen or sulphur atom as ring members and is linked with the group —CO— or —O—CO—, >N—CO—, >N—CS—, >N—CO—CO—, —SO₂— or >N—SO₂— with one of its ring carbon atoms. The heterocycle can be substituted on one of its carbon atoms or on a ring nitrogen atom by alkyl, e.g. methyl or ethyl, phenyl or phenylalkyl, e.g. benzyl, or on one of its carbon atoms by hydroxy or oxo and/or can be benz-fused on two adjacent carbon atoms. Examples of such residues are pyrrolidin-3-yl, 4-hydroxypyrrolidin-2-yl, 5-oxopyrrolidin-2-yl, piperidin-2-yl, piperidin-3-yl, 1-methylpiperidin-2-yl, 1-methylpiperidin-3-yl, 1-methylpiperidin-4-yl, morpholin-2-yl, morpholin-3-yl, thiomorpholin-2-yl, thiomorpholin-3-yl, 1,4-dimethylpiperazin-2-yl, 2-indolinyl, 3-indolinyl, 1,2,3,4-tetrahydroquinol-2-, -3- or -4-yl, 1,2,3,4-tetrahydroisoquinol-1-, -3- or -4-yl, 1-oxo-1,2,3,4-tetrahydroisoquinol-3-yl and the like.

As residues of an amino acid attached via the carboxyl group there come into consideration natural α-amino acids having the L-configuration, homologues of such amino acids, e.g. in which the amino acid side-chain is lengthened or shortened by one or two methylene groups and/or a methyl group is replaced by hydrogen, substituted aromatic α-amino acids, e.g. substituted phenylalanine or phenylglycine in which the substituent can be alkyl, e.g. methyl, halogen, e.g. fluorine, chlorine, bromine or iodine, hydroxy, alkoxy, e.g. methoxy, alkanoyloxy, e.g. acetoxy, amino, alkylamino, e.g. methylamino, dialkylamino, e.g. dimethylamino, alkanoylamino, e.g. acetylamino or pivaloylamino, alkoxycarbonylamino, e.g. t-butoxycarbonylamino, arylmethoxycarbonylamino, e.g. benzyloxycarbonylamino, and/or nitro and can be present singly or multiply, benz-fused phenylalanine or phenylglycine such as α-naphthylalanine or hydrogenated phenylalanine or phenylglycine such as cyclohexylalanine or cyclohexylglycine, a 5- or 6-membered cyclic benz-fused α-amino acid, e.g. indoline-2-carboxylic acid or 1,2,3,4-tetrahydroisoquinoline-3-carboxylic acid, a natural or homologous α-amino acid in which a carboxy group in the side-chain is present in esterified or amidated form, e.g. as an alkyl ester group such as methoxycarbonyl or t-butoxycarbonyl, or as carbamoyl group, an alkylcarbamoyl group such as methylcarbamoyl or a dialkylcarbamoyl group such as dimethylcarbamoyl, in which an amino group of the side-chain is present in acylated form, e.g. as an alkanoylamino group such as acetylamino or pivaloylamino, as an alkoxycarbonylamino group such as t-butoxycarbonylamino or as an arylmethoxycarbonylamino group such as benzyloxycarbonylamino, or in which a hydroxy group of the side-chain is present in etherified or esterified form, e.g. as an alkoxy group such as methoxy, as an arylalkoxy group such as benzyloxy or as a lower alkanoyloxy group such as acetoxy, or epimers of such amino acids, i.e. with the unnatural D-configuration. Examples of such amino acids are glycine, alanine, valine, norvaline, leucine, isoleucine, norleucine, serine, homoserine, threonine, methionine, cysteine, proline, trans-3- and trans-4-hydroxyproline, phenylalanine, tyrosine, 4-nitrophenylalanine, 4-aminophenylalanine, 4-chlorophenylalanine, β-phenylserine, phenylglycine, α-naphthylalanine, cyclohexylalanine, cyclohexylglycine, tryptophane, indoline-2-carboxylic acid, 1,2,3,4-tetrahydroisoquinoline-3-carboxylic acid, aspartic acid, asparagine, aminomalonic acid, aminomalonic acid monoamide, glutamic acid, glutamic acid mono-t-butyl ester, glutamine, N-dimethylglutamine, histidine, arginine, lysine, N-t-butoxycarbonyllysine, δ-hydroxylysine, ornithine, N-pivaloylornithine, α,γ-diaminobutyric acid or α,β-diaminopropionic acid and the like. The residue of the α-amino acid attached via the carboxyl group can be substituted N-terminally by alkyl, e.g. methyl or ethyl, in order to increase the stability of the compound of formula I against enzymatic degradation.

The residue of a dipeptide attached via the carboxyl group consists of two of the above-mentioned amino acids.

The term "acylated amino acid" or "acylated dipeptide" relates to one of the above-mentioned amino acids or to a dipeptide of two of the above-mentioned amino acids which is N-terminally substituted by the acyl residue of a carboxylic acid, of a half ester of carbonic acid, of an optionally N-substituted carbamic or thiocarbamic acid, of an optionally N-substituted oxalamide, of a sulphonic acid or of an optionally N-substituted amidosulphonic acid.

The term "pharmaceutically usable salts" embraces salts with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like. Such salts can be manufactured readily by any person skilled in the art having regard to the state of the art and taking into consideration the nature of the compound to be converted into a salt.

The compounds of formula I have at least three asymmetric carbon atoms and are therefore present in the form of optically pure diastereomers, mixtures of diastereomers, diastereomeric racemates or mixtures of diastereomeric racemates. The present invention embraces all forms. Mixtures of diastereomers, diastereomeric racemates or mixtures of diastereomeric racemates can be separated according to usual methods, e.g. by column chromatography, thin-layer chromatography, HPLC and the like.

Those compounds of formula I in which $R^1$ signifies hydrogen are preferred. $R^2$ preferably signifies imidazol-2-yl, imidazol-4-yl or thiazol-4-yl, particularly imidazol-4-yl. Further, those compounds of formula I in which $R^3$ signifies cyclohexylmethyl are preferred. $R^4$ preferably signifies alkanoyl or group (c) or (e), particularly alkanoyl or group (e). The preferred significance of $R^7$ is heteroarylalkylaminocarbonyl, preferably pyridylalkylaminocarbonyl. $R^{10}$ preferably signifies group (f), (g) or (h), particularly group (g) or group (h) in which n signifies O and $R^7$ signifies alkylaminocarbonyl. Alkanoyl is the preferred significance of $R^{11}$. $R^{12}$ preferably signifies hydrogen. $R^{13}$ in the significances alkyl, arylalkyl, heteroarylalkyl and heteroarylalkylcarbonyl, especially arylalkyl and heteroarylalkyl, is preferred. Phenylalkyl and pyridylalkyl are the most preferred significances of $R^{13}$. Likewise preferred are the compounds of formula I in which A signifies group (b). Y preferably signifies the bivalent residue of phenylalanine linked with Z at the N-terminal. Z preferably signifies the group $R^a$—O—CO— or the residue of an α-amino acid, preferably proline, which is acylated by this group, wherein $R^a$ signifies an optionally substituted, saturated aliphatic hydrocarbon residue with up to 10 carbon atoms or an optionally substituted heteroaromatic hydrocarbon residue with up to 18 carbon atoms, particularly a saturated, aliphatic hydrocarbon residue with up to 6 carbon atoms, quite particularly t-butyl. Where A signifies group (a), then there are preferred those compounds of formula I in which $R^5$ signifies phenyl or substituted phenyl, particularly phenyl. The preferred significance of $R^6$ is alkylcarbonylalkyl, aminoalkylcarbonylalkyl, substituted aminoalkylcarbonylalkyl, aminoalkylsulphonylalkyl, substituted aminoalkylsulphonylalkyl or alkylsulphonylalkyl, preferably alkylcarbonylalkyl or alkylsulphonylalkyl, particularly $C_1$-$C_4$-alkylcarbonylmethyl or $C_1$-$C_4$-alkylsulphonylmethyl.

From the above it follows that there are quite particularly preferred those compounds of formula I in which $R^1$ signifies hydrogen, $R^2$ signifies imidazol-4-yl, $R^3$ signifies cyclohexylmethyl, $R^4$ signifies alkanoyl or group (e), $R^{10}$ signifies group (g) or group (h) in which n signifies O and $R^7$ signifies alkylaminocarbonyl, $R^{12}$ signifies hydrogen, $R^{13}$ signifies arylalkyl or heteroarylalkyl, preferably phenylalkyl or pyridylalkyl, Y signifies the bivalent residue of phenylalanine linked with Z at the N-terminal and Z signifies the group $R^a$—O—CO— or the residue of proline which is acylated by this group, wherein $R^a$ signifies a saturated, aliphatic hydrocarbon residue with up to 6 carbon atoms, preferably t-butyl.

Quite especially preferred compounds of formula I are:

(S)-N-[(1S,2S,4R)-4-[(Butylcarbamoyl)methyl]-1-(cyclohexylmethyl)-2-hydroxy-5-methylhexyl]-α-[(R)-α-(3,3-dimethyl-2-oxobutyl)hydrocinnamamido]imidazole-4-propionamide, t-butyl [(S)-α-[[(S)-1-[[(1S,2S,4R)-4-[(butylcarbamoyl)methyl]-1-(cyclohexylmethyl)-2-hydroxy-5-methylhexyl]carbamoyl]-2-imidazol-4-ylethyl]carbamoyl]phenethyl]carbamate, (S)-N-[(1S,2S,4S)-1-(cyclohexylmethyl)-2-hydroxy-4-isopropyl-5-oxodecyl]-α-[(R)-α-(3,3-dimethyl-2-oxobutyl)hydrocinnamamido]imidazole-4-propionamide, (S)-N-[(1S,2S,4S,E)-1-(cyclohexylmethyl)-2-hydroxy-4-isopropyl-6-[(2-pyridylmethyl)carbamoyl]-5-hexenyl]-α-[(R)-α-(3,3-dimethyl-2-oxobutyl)hydrocinnamamido]imidazole-4-propionamide, t-butyl [(S)-α-[[(S)-1-[[(1S,2S,4S)-1-(cyclohexylmethyl)-2-hydroxy-4-isopropyl-6-(propionyloxy)hexyl]carbamoyl]-2-imidazol-4-ylethyl]carbamoyl]phenethyl]carbamate, t-butyl (R)-2-[[(S)-α-[[(R and S)-1-[[(1S,2S,4S)-1-(cyclohexylmethyl]-2-hydroxy-4-isopropyl-6-(pivaloyloxy)hexyl]carbamoyl]-2-imidazol-4-ylethyl]carbamoyl]-phenethyl]carbamoyl]-1-pyrrolidinecarboxylate, (2S or R,3S,5S,6S)-6-(Boc-D-Pro-Phe-His-NH)-7-cyclohexyl-3-isopropyl-1-(phenethylamino)-2,5-heptanediol, (2R or S,3S,5S,6S)-6-(Boc-D-Pro-Phe-His-NH)-7-cyclohexyl-3-isopropyl-1-(phenethylamino)-2,5-heptanediol and (2RS,3S,5S,6S)-6-(Boc-D-Pro-Phe-His-NH)-7-cyclohexyl-3-isopropyl-1-[(2-pyridylmethyl)amino]-2,5-heptanediol.

The compounds of formula I in the form of optically pure diastereomers, mixtures of diastereomers, diastereomeric racemates or mixtures of diastereomeric racemates as well as pharmaceutically usable salts thereof can be manufactured by a) reacting a compound of the general formula

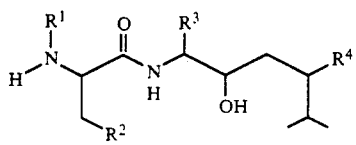

wherein $R^1$, $R^2$, $R^3$ and $R^4$ have the significance given above, with an acylating agent yielding the group

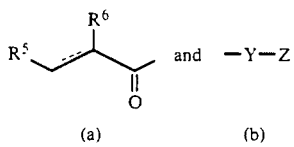

wherein $R^5$, $R^6$, Y, Z and the dotted line have the significance given above, or b) reacting a compound of the general formula

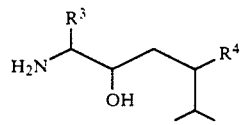

wherein $R^3$ and $R^4$ have the significance given above, with a compound of the general formula

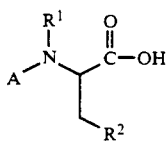

wherein $R^1$, $R^2$ and A have the significance given above, or an activated derivative thereof, or c) reacting a compound corresponding to formula I, but in which Z signifies hydrogen and the remaining symbols have the significance given above with an acylated amino acid or an acylated dipeptide, or d) for the manufacture of a compound of formula I in which $R^2$ signifies imidazol-2-yl, imidazol-4-yl or pyrazol-3-yl and/or $R^{12}$ signifies hydrogen, cleaving off the N-protecting group and/or the substituent $R^{12}$ from a compound of the general formula

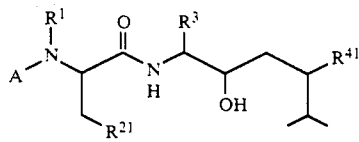

wherein $R^{21}$ signifies ethyl, propyl, isopropyl, thiazolyl-4-yl, thien-2-yl, ethoxycarbonyl, t-butylcarbonylmethyl, benzyloxycarbonylmethyl, t-butoxy or optionally N-protected imidazol-2-yl, imidazol-4-yl or pyrazol-3-yl and $R^{41}$ signifies alkanoyl, arylcarbonyl, 2,2-dialkylvinyl or one of groups (c), (d) and (e) and the remaining symbols have the significance given above, with the proviso that $R^{21}$ signifies N-protected imidazol-2-yl, imidazol-4-yl or pyrazol-3-yl and/or $R^{41}$ signifies group (e) in which $R^{10}$ signifies group (g) and $R^{12}$ signifies readily cleavable arylalkyl, alkoxycarbonyl or arylalkoxycarbonyl, and e) if desired, separating a mixture of diastereomeric racemates into the diastereomeric racemates or optically pure diastereomers, and/or f) if desired, separating a mixture of diastereomers into the optically pure diastereomers, and/or g) if desired, converting a compound obtained into a pharmaceutically usable salt.

The acylation of a compound of formula II is effected according to methods known per se. Especially suitable acylating agents are activated acid derivatives such as esters, mixed esters, acid halides and acid anhydrides or mixed acid anhydrides. The reaction is carried out in an organic solvent or solvent mixture which is inert under the reaction conditions at a temperature between about 0° C. and room temperature. As solvents there come into consideration especially aromatic hydrocarbons such as benzene, toluene or xylene, chlorinated hydrocarbons such as methylene chloride or chloroform, ethers such as diethyl ether, tetrahydrofuran or dioxan, and the like. Where the acylating agent is a peptide, the reaction is effected under reaction conditions which are usual in peptide chemistry, i.e. preferably in the presence of a condensation agent such as HBTU (O-benzotriazolyl-N,N,N',N'-tetramethyluronium hexafluorophosphate), BOP (benzotriazol-1-yloxy-bis-(dimethylamino)phosphonium hexafluorophosphate), BOPC (bis(2-oxo-2-oxazolidinyl)phosphine chloride), HOBT (N-hydroxybenzotriazole), DBU (1,8-diazabicyclo[5.4.0]undec-7-ene), DCC (dicyclohexylcarbodiimide), EDC (N-ethyl-N'(3-dimethylaminopropyl)carbodiimide hydrochloride), Hünig base (ethyldiisopropylamine), and the like. The reaction is conveniently carried out in an organic solvent or solvent mixture which is inert under the reaction conditions at a temperature between about 0° and 50° C., preferably at about room temperature. As solvents there come into consideration especially dimethylformamide, methylene chloride, acetonitrile, tetrahydrofuran, and the like.

The reaction of a compound of formula III with a compound of formula IV is also effected according to methods which are known per se in peptide chemistry, i.e. under the same conditions as given above for the reaction of a compound of formula II with a peptide. Examples of suitable activated derivatives of a compound of formula IV are acid halides, acid anhydrides, mixed anhydrides, esters, mixed esters, and the like.

The reaction of a compound of formula I in which Z signifies hydrogen with an acylated amino acid or an acylated dipeptide in accordance with process variant c) is also effected according to methods which are known per se in peptide chemistry, i.e. under the conditions given above for the reaction of a compound of formula II with a peptide.

The cleavage of the N-protecting group(s) in accordance with process variant d) is also effected according to methods known per se depending on the nature of the N-protecting group to be cleaved off. However, the cleavage is conveniently effected by acidic or basic hydrolysis. For the acidic hydrolysis there is advantageously used a solution of a mineral acid such as hydrochloric acid, hydrobromic acid, trifluoroacetic acid, sulphuric acid, phosphoric acid and the like in an inert solvent or solvent mixture. Suitable solvents are alcohols such as methanol or ethanol, ethers such as tetrahydrofuran or dioxan, chlorinated hydrocarbons such as methylene chloride, and the like. For the basic hydrolysis there can be used alkali metal hydroxides and carbonates such as potassium or sodium hydroxide or potassium or sodium carbonate, organic amines such as piperidine, and the like. Inert organic solvents, such as have been mentioned above for the acidic hydrolysis, can be added as solubilizers. The reaction temperature for the acidic and basic hydrolysis can be varied in a range from about 0° C. to the reflux temperature, whereby the reaction is preferably carried out between about 0° C. and room temperature. The t-butoxycarbonyl residue is conveniently cleaved off with trifluoroacetic acid or formic acid in the presence or absence of an inert solvent. The Fmoc protecting group is preferably cleaved off with piperidine at about room temperature. The benzyloxycarbonyl group can be cleaved off in a known manner by acidic hydrolysis as described above or hydrogenolytically. The benzyl group is conveniently cleaved off hydrogenolytically.

The starting materials of formula II are novel and are also an object of the present invention. These compounds can be prepared by reacting a compound of formula III with optionally N-methylated histidine, leucine, norleucine, norvaline, thiazolylalanine, thienylalanine, aspartic acid ethyl ester, glutamic acid t-butyl ester, glutamic acid benzyl ester or t-butoxyserine. This reaction is also effected according to methods which are known per se in peptide chemistry, i.e. under the reaction conditions which are described above for the reaction of a compound of formula II with a dipeptide.

The starting materials of formula III are also novel and are an object of the present invention. They can be prepared, for example, by cleaving off the amino protecting group and, where applicable, simultaneously also the O-protecting group(s) in a compound of the general formulae

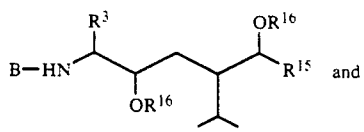

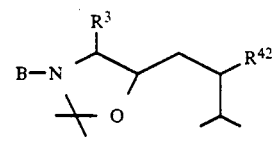

wherein B signifies an amino protecting group, preferably t-butoxycarbonyl or benzyloxycarbonyl, $R^{15}$ signifies group (f) or alkylaminocarbonylethyl, arylalkylaminocarbonylethyl or heteroarylalkylaminocarbonylethyl and $R^{16}$ signifies an O-protecting group, preferably tetrahydropyranyl or 1-ethoxyethyl, or $R^{15}$ signifies alkylaminocarbonyl, arylalkylaminocarbonyl or heteroarylalkylaminocarbonyl and $R^{16}$ signifies hydrogen and $R^{42}$ signifies alkanoyl, arylcarbonyl, 2,2-dialkylvinyl or one of groups (c), (d) and (e), with the proviso that $R^9$ signifies hydrogen in group (e) when $R^{10}$ signifies group (f) or group (h) in which n signifies 0 or 2 and $R^7$ signifies alkylaminoacarbonyl, arylalkylaminocarbonyl or heteroarylalkylaminocarbonyl, and $R^3$ has the significance given above.

The cleavage of the N-protecting group and, where applocable, O-protecting group(s) is also effected according to methods known per se, for example in an organic solvent or solvent mixture which is inert under the reaction conditions at a temperature between about 0° C. and room temperature with an acid such as hydrochloric acid, trifluoroacetic acid, and the like. Suitable solvents are ethers such as tetrahydrofuran or dioxan, alcohols such as methanol or chlorinated hydrocarbons such as methylene chloride, and the like. Under these reaction conditions the O-protecting groups in a compound of formula VI in which $R^{16}$ signifies an O-protecting group or the oxazolidine ring in a compound of formula VII are/is—as already mentioned—simultaneously cleaved off or cleaved, respectively.

The starting materials of formula IV are known or can be obtained in analogy to the preparation of the known compounds.

The compounds of formulae VI and VII are also novel and are an object of the present invention. They can be prepared according to various methods known per se starting from compounds of formula VIII. These preparative procedures are compiled in the following Schemes I–IV. In these Schemes $R^{71}$ signifies alkyl, aryl or heteroaryl, $R^{72}$ signifies alkylaminocarbonyl, arylalkylaminocarbonyl or heteroarylalkylaminocarbonyl, $R^{73}$ signifies alkyl or aryl, $R^{121}$ and $R^{131}$ each independently signify hydrogen, alkyl, arylalkyl, heteroarylalkyl or aryl or $R^{121}$ and $R^{131}$ together with the nitrogen atom to which they are attached signify a 5- or 6-membered heterocycle or optionally substituted benzimidazolonyl, $R^{161}$ signifies an O-protecting group, Et signifies ethyl and X signifies p-tolylsulphonyl, methylsulphonyl, trifluoromethylsulphonyl or p-bromobenzenesulphonyl and B, $R^3$, $R^{12}$ and $R^{13}$ have the significance given above. With respect to the precise reaction conditions, reference is made to the experimental section.

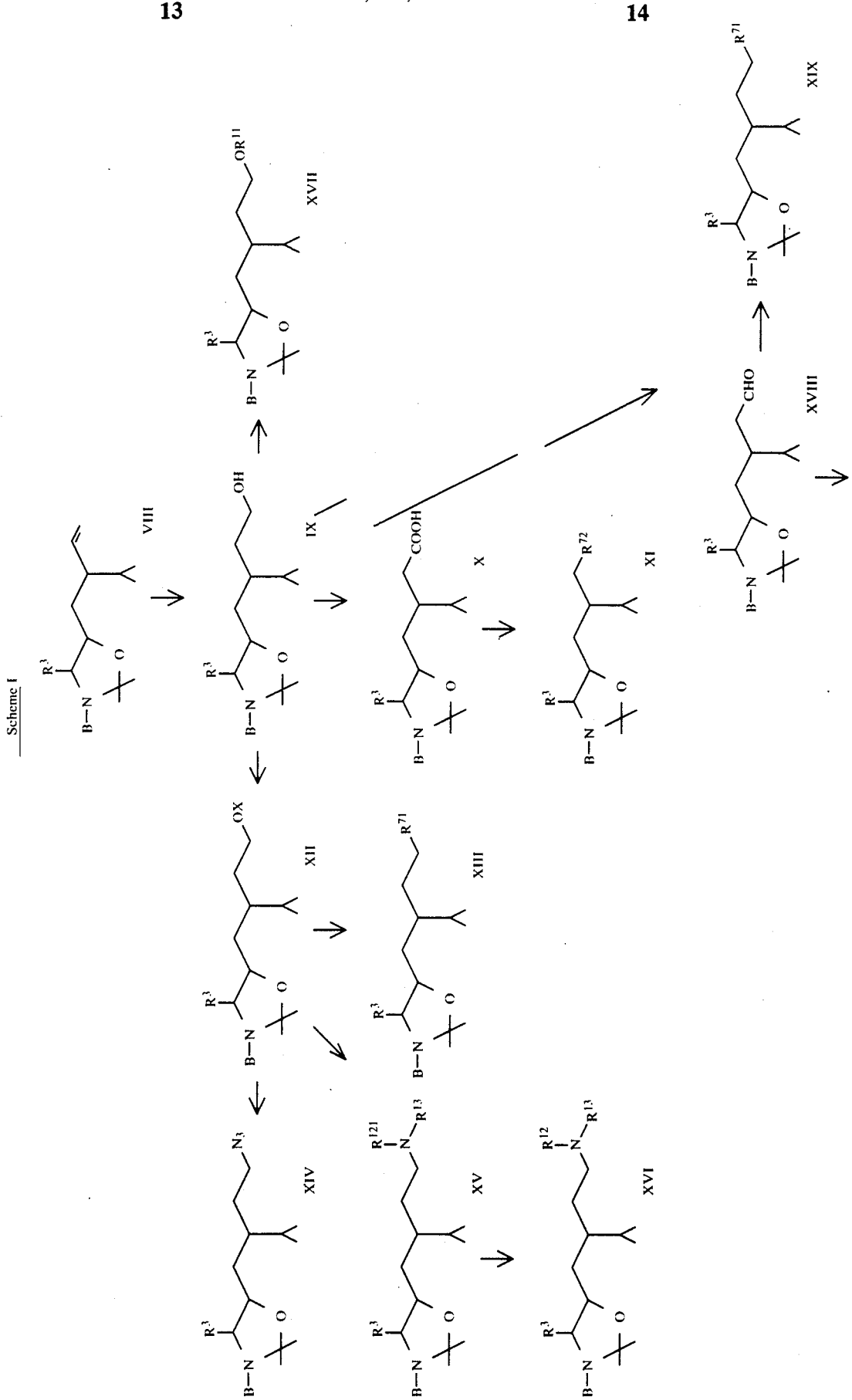

-continued
Scheme I
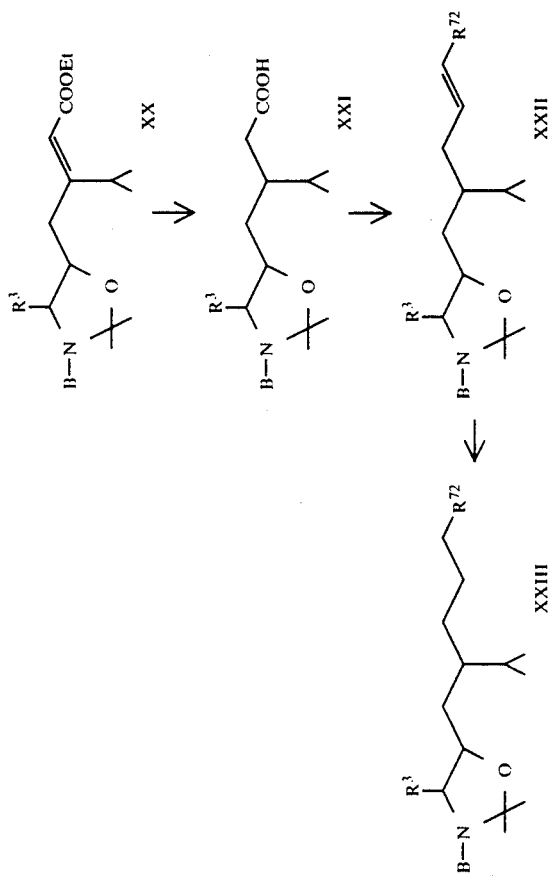

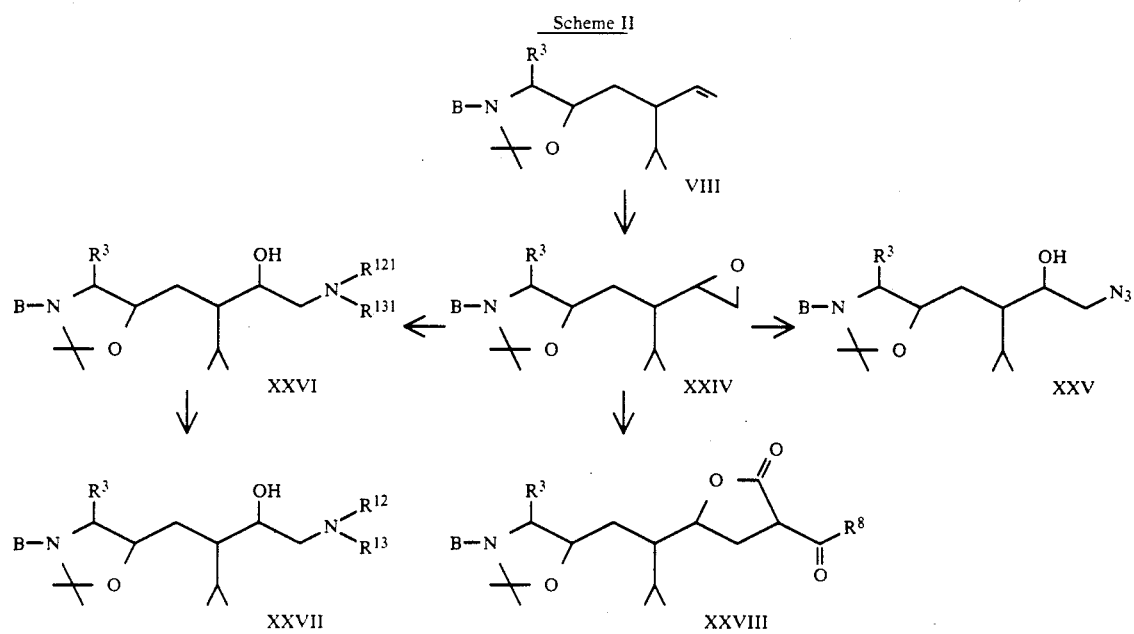

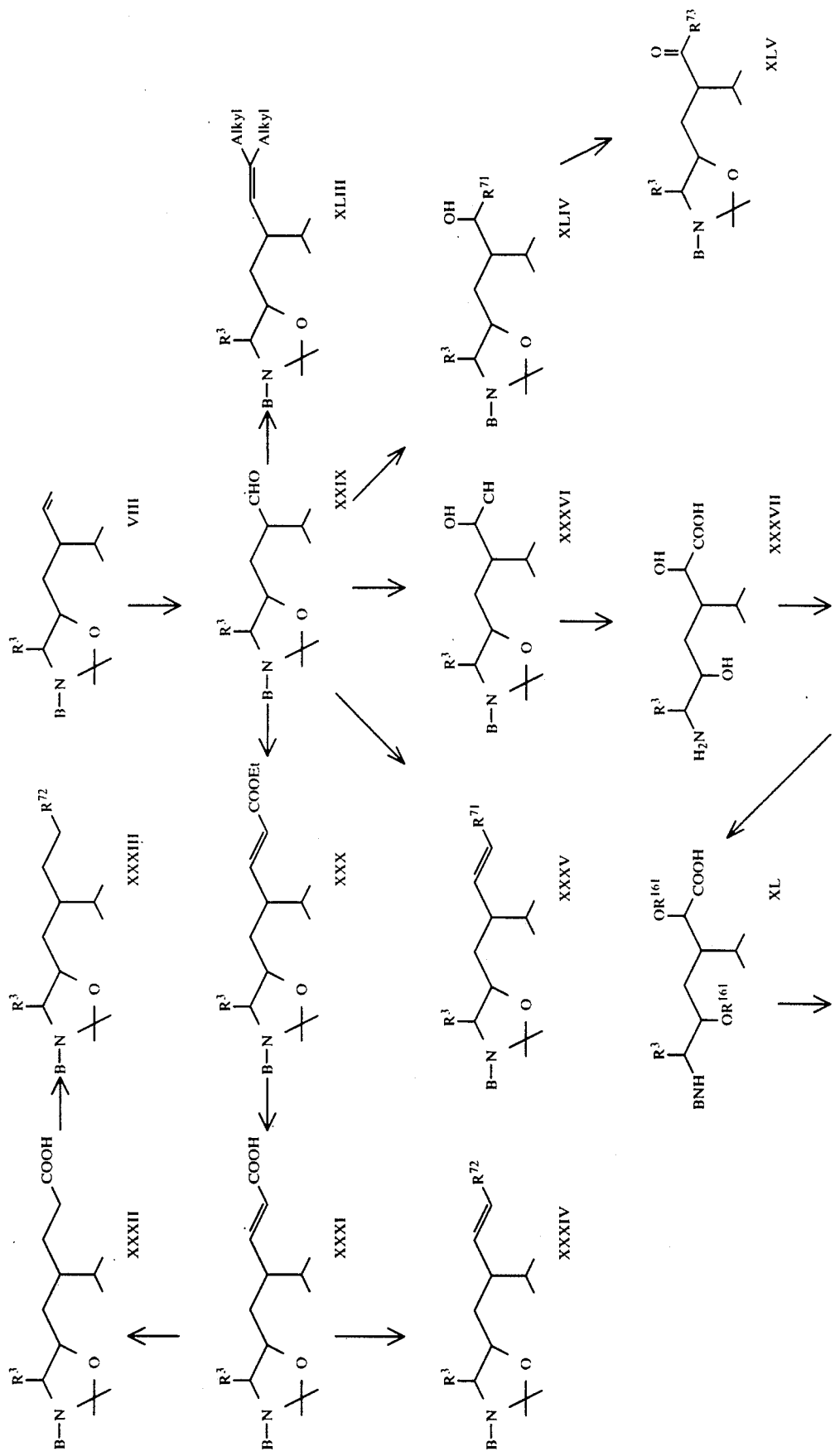
Scheme III

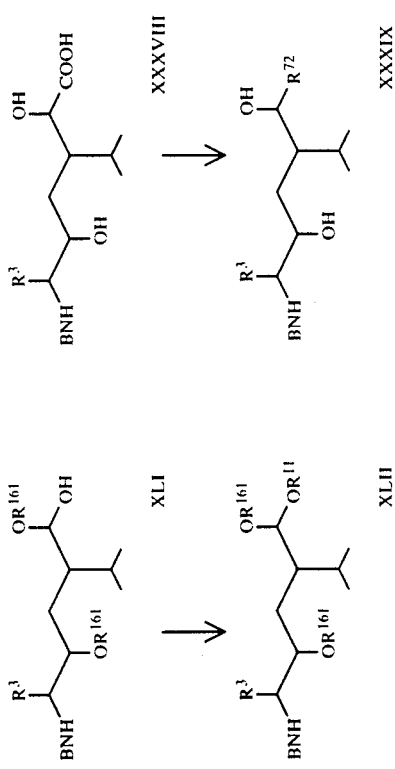

Scheme IV

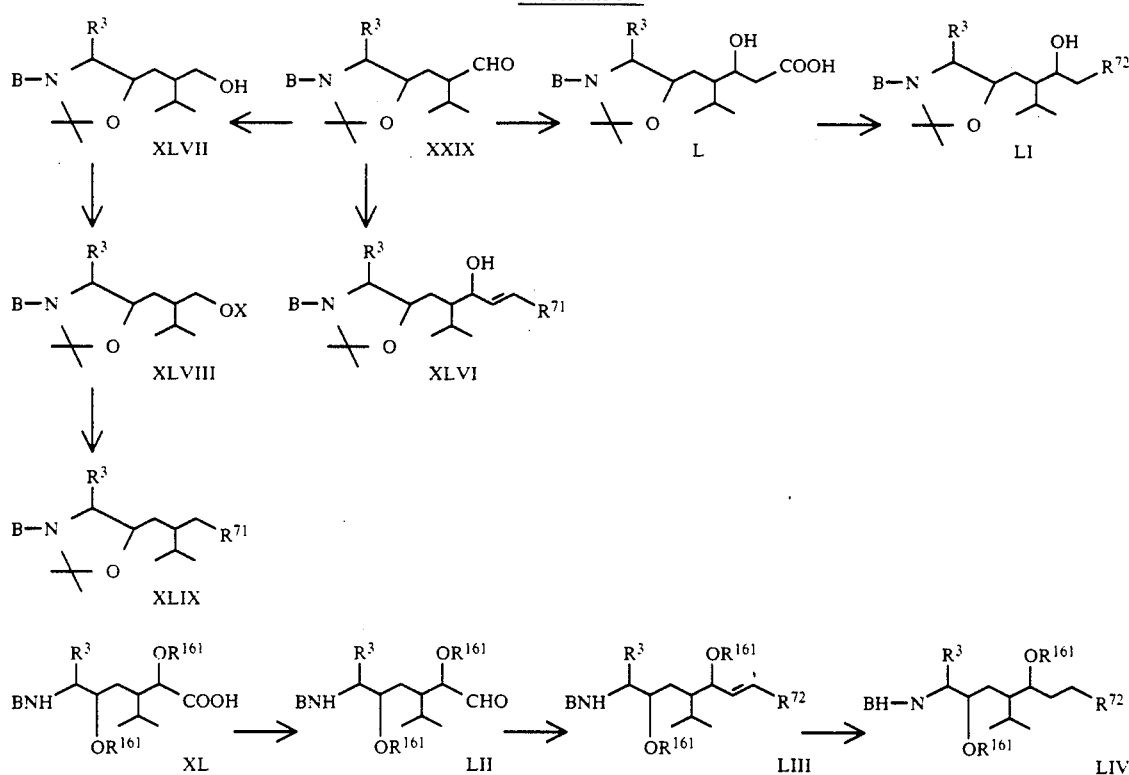

It will be appreciated that the compounds of formulae XXXIX, XLII and LIV fall under formula VI above, while the compounds of formulae XI, XIII–XVII, XIX, XXII, XXIII, XXV–XXVIII, XXXIII–XXXV, XLIII–-XLVII, XLIX and LI fall under formula VII above.

All of the compounds which appear in Schemes I–IV, with the exception of those of formulae VIII and XXIX, are novel and are likewise objects of the present invention.

The compounds of formula VIII are also novel and can be prepared, for example, by reacting an aldehyde of the general formula

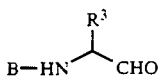

LV wherein B and $R^3$ have the significance given above, with a compound of the general formula

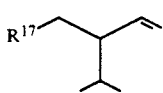

LVI wherein $R^{17}$ signifies chlorine, bromine or iodine, preferably bromine, in a Grignard reaction. This reaction is also effected according to methods known per se, for example in a solvent which is inert under the reaction conditions, such as an ether, at a temperature between about 0° and 50° C., preferably at room temperature. Subsequently, the resulting compound of the general formula

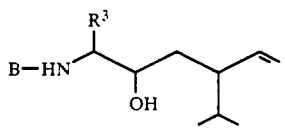

LVII wherein B and $R^3$ have the significance given above, is reacted with 2,2-dimethoxypropane in the presence of p-toluenesulphonic acid to give the desired compound of formula VIII.

The starting materials of formula V in which $R^{21}$ signifies N-protected imidazol-2-yl, imidazol-4-yl or pyrazol-3-yl are also novel and are an object of the present invention. They can be prepared, for example, by reacting a compound of formula III with a compound corresponding to formula IV, but in which $R^2$ signifies N-protected imidazol-2-yl, imidazol-4-yl or pyrazol-3-yl or an activated derivative thereof. The reaction is effected according to methods which are known per se in peptide chemistry, i.e. under the same conditions as have been given above for the reaction of a compound of formula III with a compound of formula IV.

The remaining compounds of formula V fall under formula I and can be prepared according to the procedures given for the manufacture of the compounds of formula I.

The compounds of formula I and their pharmaceutically usable salts have an inhibitory activity on the natural enzyme renin. The latter passes from the kidneys into the blood and there brings about the cleavage of angiotensinogen with the formation of the decapeptide angiotensin I which is then cleaved in the lungs, the kidneys and other organs to the octapeptide angiotensin II. Angiotensin II increases the blood pressure not only directly by arterial constriction, but also indirectly by the liberation of the sodium ion-retaining hormone aldosterone from the adrenal gland, with which is associated an increase in the extracellular fluid volume. This increase is attributed to the action of angiotensin II itself or to the heptapeptide angiotensin III which is formed therefrom as a cleavage product. Inhibition of the enzymatic activity of renin brings about a decrease in the formation of angiotensin I and as a consequence thereof the formation of a smaller amount of angiotensin II. The reduced concentration of this active peptide hormone is the actual reason for the blood pressure-lowering activity of renin inhibitors.

The activity of renin inhibitors can be demonstrated experimentally by means of the in vitro test described hereinafter:

In vitro test with pure human renin

The test is carried out in Eppendorf test tubes. The incubation mixture consists of (1) 100 μl of human renin in buffer A (0.1M sodium phosphate solution, pH 7.4, containing 0.1% bovine serum albumin, 0.1% sodium azide and 1 mM ethylenediaminetetraacetic acid), sufficient for a renin activity of 2-3 ng of angiotensin I/ml/hr.; (2) 145 μl of buffer A; (3) 30 μl of a 10 μM human tetradecapeptide renin substrate (hTD) in 10 mM hydrochloric acid; (4) 15 μl of dimethyl sulphoxide with or without inhibitor and (5) 10 μl of a 0.03 molar solution of hydroxyquinoline sulphate in water.

The samples are incubated for 3 hours at 37° C. or 4° C. in triplicate. 2×100 μl samples per experimental test tube are used in order to measure the production of angiotensin I via RIA (standard radioimmunoassay; clinical assay solid phase kit). Cross reactivities of the antibody used in the RIA are: angiotensin I 100%; angiotensin II 0.0013%; hTD (angiotensin I-Val-Ile-His-Ser-OH) 0.09%. The production of angiotensin I is determined by the difference between the experiment at 37° C. and that at 4° C.

The following controls are carried out:

(a) Incubation of hTD samples without renin and without inhibitor at 37° C. and 4° C. The difference between these two values gives the base value of angiotensin I production.

(b) Incubation of hTD samples with renin, but without inhibitor at 37° C. and 4° C. The difference between these values give the maximal value of angiotensin I production.

In each sample the base value of the angiotensin I production is subtracted from the angiotensin I production which is determined. The difference between the maximal value and the base value gives the value of the maximal substrate hydrolysis (=100%) by renin.

The results are given as $IC_{50}$ values which denote that concentration of the inhibitor at which the enzymatic activity is inhibited by 50%. The $IC_{50}$ values are determined from a linear regression curve from a logit-log plot.

The results obtained in this test are compiled in the following Table:

TABLE

| Compound | $IC_{50}$ values in μmol/lt. |
| --- | --- |
| A | 0.003 |
| B | 0.009 |
| C | 0.007 |
| D | 0.013 |
| E | 0.009 |
| F | 0.010 |
| G | 0.011 |
| H | 0.004 |
| I | 0.008 |

A = (S)-N-[(1S,2S,4R)-4-[Butylcarbamoyl)methyl]-1-(cyclohexylmethyl)-2-hydroxy-5-methylhexyl]-α-(3,3-dimethyl-2-oxobutyl)hydrocinnamamido]imidazole-4-propionamide,
B = t-Butyl [(S)-α-[[(S)-1-[[(1S,2S,4R)-4-[(butyl-carbamoyl)methyl]-1-(cyclohexylmethyl)-2-hydroxy-5-methylhexyl]carbamoyl]-2-imidazol-4-ylethyl]carbamoyl]-phenethyl]-carbamate,
C = (S)-N-[(1S,2S,4S)-1-(Cyclohexylmethyl)-2-hydroxy-4-isopropyl-5-oxodecyl]-α-[(R)-α-(3,3-dimethyl-2-oxobutyl]hydrocinnamamido]imidazole-4-propionamide,
D = (S)-N-[(1S,2S,4S,E)-1-(Cyclohexylmethyl)-2-hydroxy-4-isopropyl-6-[(2-pyridylmethyl)carbamoyl]-5-hexenyl]-α-[(R)-α-(3,3-dimethyl-2-oxobutyl) hydrocinnamamide]-imidazole-4-propionamide,
E = t-Butyl [(S)-α-[[(S)-1-[[(1S,2S,4S)-1-(Cyclohexylmethyl)-2-hydroxy-4-isopropyl-6-(propionyloxy)-hexyl]-carbamoyl]-2-imidazol-4-ylethyl]carbamoyl]-phenethyl]-carbamate,
F = t-Butyl (R)-2-[[(S)-α-[[(R and S)-1-[[(1S,2S,4S)-1-(cyclohexylmethyl)-2-hydroxy-4-isopropyl-6-(pivaloyloxy)-hexyl]carbamoyl]-2-imidazol-4-ylethyl]carbamoyl]phenethyl]-carbamoyl]-1-pyrrolidinecarboxylate,
G = (2S or R,3S,5S,6S)-6-(Boc—D—Pro—Phe—His—NH)-7-cyclohexyl-3-isopropyl-1-(phenethylamino)-2,5-heptanediol,
H = (2R or S,3S,5S,6S)-6-(Boc—D—Pro—Phe—His—NH)-7-cyclohexyl-3-isopropyl-1-(phenethylamino)-2,5-heptanediol, and
I = (2RS,3S,5S,6S)-6-(Boc—D—Pro—Phe—His—NH)-7-cyclohexyl-3-isopropyl-1-[(2-pyridylmethyl)-amino]-2,5-heptanediol.

The compounds of formula I as well as their pharmaceutically usable salts can be used as medicaments, e.g. in the form of pharmaceutical preparations. The pharmaceutical preparations can be administered enterally such as orally, e.g. in the form of tablets, coated tablets, dragees, hard and soft gelatine capsules, solutions, emulsions or suspensions, nasally, e.g. in the form of nasal sprays, or rectally, e.g. in the form of suppositories. However, the administration can also be effected parenterally such as intramuscularly or intravenously, e.g. in the form of injection solutions.

For the manufacture of tablets, coated tablets, dragees and hard gelatine capsules the compounds of formula I as well as their pharmaceutically usable salts can be processed with pharmaceutically inert, inorganic or organic excipients. Lactose, maize starch or derivatives thereof, talc, stearic acid or its salts etc. can be used e.g. as such excipients for tablets, dragees and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preserving agents, solubilizers, viscosity-increasing substances, stabilizing agents, wetting agents, emulsifying agents, sweetening agents, colouring agents, flavouring agents, salts for varying the osmotic pressure, buffers, coating agents or antioxidants. They can also contain still other therapeutically valuable substances.

In accordance with the invention the compounds of general formula I as well as their pharmaceutically usable salts can be used in the control or prevention of high blood pressure and cardiac insufficiency. The dosage can vary within wide limits and will, of course, be fitted to the individual requirements in each particular case. In general, in the case of oral administration there should suffice a daily dosage of about 3 mg to about 3 g, preferably about 10 mg to about 1 g, e.g. approximately 300 mg per person, divided in preferably 1-3 unit doses, which can e.g. be of the same amount, whereby, however, the upper limit just given can also be exceeded when this is found to be indicated. Usually, children receive half of the adult dosage.

The following Examples are intended to illustrate the present invention, but are not intended to be limiting in any manner. All temperatures are given in degrees Celsius. The following abbreviations or combinations thereof are used:

| | |
|---|---|
| Boc = | t-butoxycarbonyl |
| Fmoc = | 9-fluorenylmethoxycarbonyl |
| H—His—OH = | L-histidine |
| H—Phe—OH = | L-phenylalanine |
| H—D—Pro—OH = | D-proline |
| H—Phe—His—OH = | N-[(S)-2-amino-3-phenylpropyl]-L-histidine |
| (Phe—His—NH) = | L-phenylalaninyl-L-histidinamido |
| (Fmoc)₂His—OH = | N-α-N-im-di-Fmoc-L-histidine |
| Boc—Phe—His(Boc)—OH = | Boc-L-phenylalaninyl-N-im-Boc-L-histidine |

EXAMPLE 1

A mixture of 290 mg (0.36 mmol) of benzyl [(2RS,3S,5S,6S)-7-cyclohexyl-2,5-dihydroxy-3-isopropyl-6-[[N-(3-phenyl-L-alanyl)-L-histidyl]amino]heptyl]-(2-pyridylmethyl)carbamate, 86 mg (0.40 mmol) of Boc-D-Pro-OH, 0.092 ml (0.73 mmol) of 4-ethylmorpholine, 108 mg (0.80 mmol) of HOBT, 84 mg (0.44 mmol) of EDC and 10 ml of dimethylformamide is stirred at room temperature for 2 days. Thereafter, the reaction mixture is poured into 70 ml of ice-cold 2N sodium bicarbonate solution and extracted three times with 150 ml of ethyl acetate each time. The organic extracts are washed in succession with 70 ml of sodium bicarbonate solution and 70 ml of saturated sodium chloride solution, combined, dried and evaporated. Chromatography of the residue on 25 g of silica gel with a 14:1:0.1 mixture of methylene chloride, methanol and ammonia yields, after recrystallization from methylene chloride/ether/hexane, 280 mg of benzyl [(2RS,3S,5S,6S)-6-(Boc-D-Pro-Phe-His-NH)-7-cyclohexyl-2,5-dihydroxy-3-isopropylheptyl]-(2-pyridylmethyl)-carbamate as a white solid, melting point 108°.

The benzyl [(2RS,3S,5S,6S)-7-cyclohexyl-2,5-dihydroxy-3-isopropyl-6-[[N-(3-phenyl-L-alanyl)-L-histidyl]amino]heptyl]-(2-pyridylmethyl)carbamate used as the starting material was prepared as follows:

100 mg (0.27 mmol) of t-butyl [(1S,2S,4S,5RS)-1-(cyclohexylmethyl)-5,6-epoxy-2-hydroxy-4-isopropylhexyl]carbamate and 0.136 ml (1.35 mmol) of 2-aminomethylpyridine in 5 ml of methanol are heated to reflux under argon for 24 hours. Thereafter, the reaction mixture is evaporated to dryness and the residue is chromatorgraphed on 20 g of silica gel with a 14:1:0.1 mixture of methylene chloride, methanol and ammonia as the eluting agent, whereby there are obtained 100 mg of t-butyl [(1S,2S,4S, 5RS)-1-(cyclohexylmethyl)-2,5-dihydro-4-isopropyl-6-(2-pyridylmethyl)hexyl]carbamate as an oil, MS: 477 (M+H)⁺.

A mixture of 770 mg (1.49 mmol) of t-butyl [(1S,2S, 4S,5RS)-1-(cyclohexylmethyl)-2,5-dihydro-4-isopropyl-6-(2-pyridylmethyl)hexyl]carbamate, 0.414 ml (2.97 mmol) of triethylamine, 4.44 mg (1.784 mmol) of N-(benzyloxycarbonyloxy)succinimide and 20 ml of methylene chloride is stirred at room temperature for 1.5 hours. Thereafter, the reaction mixture is evaporated to dryness under reduced pressure and the residue is dissolved in 250 ml of ether. The ether solution is washed in succession with 80 ml of 2N sodium bicarbonate solution and sodium chloride solution, dried and evaporated under reduced pressure. The residue (1.2 g) is left to stand overnight in 9 ml of 3N methanolic hydrochloric acid and thereafter evaporated to dryness under reduced pressure. Chromatography of the residue on 100 g of silica gel with a 150:10:1 mixture of methylene chloride, methanol and ammonia yields 640 mg of (2RS,3S,5S,6S)-6-amino-7-cyclohexyl-3-isopropyl-1-[(2-pyridylmethyl)amino]-2,5-heptanediol as an oil, MS: 377 (M+H)⁺.

A mixture of 350 mg (0.68 mmol) of (2RS,3S,5S,6S)-6-amino-7-cyclohexyl-3-isopropyl-1-[(2-pyridylmethyl)amino]-2,5-heptanediol, 450 mg (0.75 mmol) of (Fmoc)₂His-OH, 0.17 ml (1.37 mmol) of 4-ethylmorpholine, 203 mg (1.5 mmol) of HOBT, 157 mg (0.82 mmol) of EDC and 10 ml of dimethylformamide is stirred at room temperature overnight, subsequently poured into 70 ml of ice-cold 2N sodium bicarbonate solution and extracted three times with 150 ml of ethyl acetate each time. The organic extracts are washed in succession with 70 ml of sodium bicarbonate solution and 70 ml of saturated sodium chloride solution, combined, dried and evaporated. The residue (910 mg) in 30 ml of methylene chloride and 1 ml of piperidine is stirred at room temperature for 2.5 hours. Thereafter, the reaction mixture is evaporated and the residue is triturated with hexane. Filtration of the separated precipitate yields 620 mg of a solid which is chromatographed on 50 g of silica gel with a 14:1:0.1 mixture of methylene chloride, methanol and ammonia. In this manner there are obtained 360 mg of benzyl [(2RS,3S,5S,6S)-6-[(S)-α-amino-4-imidazolepropionamido]-7-cyclohexyl-2,5-dihydroxy-3-isopropylheptyl]-(2-pyridylmethyl)carbamate as a foam, MS: 649 (M+H)⁺.

A mixture of 340 mg (0.52 mmol) of benzyl [(2RS,3S, 5S,6S)-6-[(S)-α-amino-4-imidazolepropionamido]-7-cyclohexyl-2,5-dihydroxy-3-isopropylheptyl]-(2-pyridylmethyl)carbamate, 225 mg (0.58 mmol) of Fmoc-Phe-OH, 0.132 ml (1.05 mmol) of 4-ethylmorpholine, 155 mg (1.15 mmol) of HOBT, 121 mg (0.63 mmol) of EDC and 10 ml of dimethylformamide is stirred at room temperature overnight. Thereafter, the reaction mixture is poured into 70 ml of ice-cold 2N sodium bicarbonate solution and extracted three times with 150 ml of ethyl acetate each time. The organic extracts are washed in succession with 70 ml of sodium bicarbonate solution and 70 ml of saturated sodium chloride solution, combined, dried and evaporated. The residue (640 mg) in 30 ml of methylene chloride and 1 ml of piperidine is stirred at room temperature for 2.5 hours. Then, the reaction mixture is evaporated and the residue (500 mg) is chromatographed on 50 mg of silica gel with a 14:1:0.1 mixture of methylene chloride, methanol and ammonia as the eluting agent. Recrystallization of the crude product obtained (320 mg) from methylene chloride/ether/hexane yields 280 mg of benzyl [(2RS,3S,5S,6S)-7-cyclohexyl-2,5-dihydroxy-3-isopropyl-6-[[N-(3-phenyl-L-alanyl)-L-histidyl]amino]heptyl]-(2-pyridylmethyl)carbamate as a white solid, melting point 94°.

EXAMPLE 2

100 mg (0.1 mmol) of benzyl [(2RS,3S,5S,6S)-6-(Boc-D-Pro-Phe-His-NH)-7-cyclohexyl-2,5-dihydroxy-3-isopropylheptyl]-(2-pyridylmethyl)carbamate are hydrogenated at room temperature and atmospheric pressure for 4 hours in 15 ml of 1N methanolic ammonia in the presence of 40 mg of 5% palladium on charcoal. After completion of the hydrogen uptake the catalyst is filtered off, the filtrate is evaporated to dryness under reduced pressure and the residue is recrystallized from methylene chloride/ether. In this manner there are obtained 90 mg of (2RS,3S,5S,6S)-6-(Boc-D-Pro-Phe-His-NH)-7-cyclohexyl-3-isopropyl-1-[(2-pyridylmethyl)amino]-2,5-heptanediol as a white solid, melting point 103°.

EXAMPLE 3

The following compounds were manufactured in an analogous manner to that described in Example 1 starting from t-butyl [(1S,2S,4S,5RS)-1-(cyclohexylmethyl)-5,6-epoxy-2-hydroxy-4-isopropylhexyl]carbamate by reaction with an amine, introduction of the carbobenzoxy protecting group and cleavage of the Boc protecting group, reaction with (Fmoc)$_2$His-OH and cleavage of the Fmoc protecting group with piperidine, reaction with Fmoc-Phe-OH and cleavage of the Fmoc protecting group with piperidine and reaction with Boc-D-Pro-OH:

Using butylamine the benzyl [(2RS,3S,5S,6S)-6-(Boc-D-Pro-Phe-His-NH)-7-cyclohexyl-2,5-dihydroxy-3-isopropylheptyl]butylcarbamate as a white solid, melting point 111° (from methylene chloride/ether/hexane), MS: 959 (M+H)+, and using phenethylamine the benzyl (2S or R,3S,5S,6S)-6-[(Boc-D-Pro-Phe-His-NH)-7-cyclohexyl-2,5-dihydroxy-3-isopropylheptyl]phenethylcarbamate as a white solid, melting point 98° (from methylene chloride/ether/hexane), MS: 1007 (M+H)+.

EXAMPLE 4

The following two epimeric compounds were manufactured in an analogous manner to that described in Example 1:

From benzyl [(2S or R,3S,5S,6S)-7-cyclohexyl-2,5-dihydroxy-6-(His-NH)-3-isopropylheptyl]]phenethylcarbamate and Boc-Phe-OH the benzyl [(2S or R,3S,5S,6S)-6-[[N-[N-(t-butoxycarbonyl)-3-phenyl-L-alanyl]-L-histidyl]amino]-7-cyclohexyl-2,5-dihydroxy-3-isopropylheptyl]phenethylcarbamate as a white solid, MS: 910 (M+H)+, and from benzyl [(2R or S,3S,5S,6S)-7-cyclohexyl-2,5-dihydroxy-6-(His-NH)-3-isopropylheptyl]phenethylcarbamate and Boc-Phe-OH the benzyl [(2R or S,3S,5S,6S)-6-[[N-[N-(t-butoxycarbonyl)-3-phenyl-L-alanyl]-L-histidyl]amino]-7-cyclohexyl-2,5-dihydroxy-3-isopropylheptyl]phenethylcarbamate as a white solid, melting point 80° (dec., from methylene chloride/ether/methanol/hexane), MS: 910 (M+H)+.

The epimeric compounds benzyl [(2S or S,3S,5S,6S)-7-cyclohexyl-2,5-dihydroxy-6-(His-NH)-3-isopropylheptyl]phenethylcarbamate and benzyl [(2R or S,3S,5S,6S)-7-cyclohexyl-2,5-dihydroxy-6-(His-NH)-3-isopropylheptyl]phenethylcarbamate used as the starting materials were prepared in an analogous manner to that described in Example 1 by reacting t-butyl [(1S,2S,4S,5RS)-1-(cyclohexylmethyl)-5,6-epoxy-2-hydroxy-4-isopropylhexyl]carbamate with phenethylamine, introducing the carbobenzoxy protecting group and cleaving off the Boc protecting group with hydrochloric acid in methanol, reacting the compound obtained with (Fmoc)$_2$His-OH and cleaving off the Fmoc protecting group with piperidine and subsequently separating the two epimeric compounds, both as a white foam, by column chromatography, MS: 662 (M+H)+.

EXAMPLE 5

The following compounds were manufactured in an analogous manner to that described in Example 2 by hydrogenolytically cleaving off the carbobenzoxy protecting group:

From benzyl [(2RS,3S,5S,6S)-6-(Boc-D-Pro-Phe-His-NH)-7-cyclohexyl-2,5-dihydroxy-3-isopropylheptyl]butylcarbamate the (2RS,3S,5S,6S)-6-(Boc-D-Pro-Phe-His-NH)-1-(butylamino)-7-cyclohexyl-3-isopropyl-2,5-heptanediol as a white solid, melting point 110° (from methylene chloride/ether), MS: 825 (M+H)+;

from benzyl (2S or R,3S,5S,6S)-6-[(Boc-D-Pro-Phe-His-NH)-7-cyclohexyl-2,5-dihydroxy-3-isopropylheptyl]phenethylcarbamate the (2R or S,3S,5S,6S)-6-(Boc-D-Pro-Phe-His-NH)-7-cyclohexyl-3-isopropyl-1-(phenethylamino)-2,5-heptanediol and the epimeric (2S or R,3S,5S,6S)-6-(Boc-D-Pro-Phe-His-NH)-7-cyclohexyl-3-isopropyl-1-(phenethylamino)-2,5-heptanediol, each as foam, MS (each): 873 (M+H)+, which were separated by column chromatography;

from benzyl [(2S or R,3S,5S,6S)-6-[[N-[N-(t-butoxycarbonyl)-3-phenyl-L-alanyl]-L-histidyl]amino]-7-cyclohexyl-2,5-dihydroxy-3-isopropylheptyl]phenethylcarbamate the t-butyl [(S)-α-[[(S)-1-[[(1S, 2S,4S,5S or R)-1-cyclohexyl-2,5-dihydroxy-4-isopropyl-6-(phenethylamino)hexyl]carbamoyl]-2-imidazol-4-ylethyl]carbamoyl]phenethyl]carbamate as a foam, MS: 776 (M+H)+, and from benzyl [(2R or S,3S,5S,6S)-6-[[N-[N-(t-butoxycarbonyl)-3-phenyl-L-alanyl]-L-histidyl]amino]-7-cyclohexyl-2,5-dihydroxy-3-isopropylheptyl]phenethylcarbamate the t-butyl [(S)-α-[[(S)-1][(1S, 2S,4S,5R or S)-1-cyclohexyl-2,5-dihydroxy-4-isopropyl-6-(phenethylamino)hexyl]carbamoyl]-2-imidazol-4-ylethyl]carbamoyl]phenethyl]carbamate as a foam, MS: 776 (M+H)+.

EXAMPLE 6

490 mg (0.565 mmol) of (S)-N-[(1S,2S,4S,5S or R)-1-(cyclohexylmethyl)-2,5-dihydroxy-6-[4-(2-hydroxyethyl)-1-piperazinyl]-4-isopropylhexyl]-α-[(R)-α-(3,3-dimethyl-2-oxobutyl)hydrocinnamamido]-3-t-butoxycarbonylimidazole-4-propionamide are dissolved in 5.5 ml of methanol, treated with 23 mg of potassium carbonate and stirred at room temperature for 5 hours. Thereafter, the reaction mixture is evaporated and the residue is chromatographed on 35 g of silica gel with a 110:10:1 mixture of methylene chloride, methanol and ammonia as the eluting agent, whereby there are obtained 347 mg of (S)-N-[(1S,2S,4S,5S or R)-1-(cyclohexylmethyl)-2,5-dihydroxy-6-[4-(2-hydroxyethyl)-1-piperazinyl]-4-isopropylhexyl]-α-[(R)-α-(3,3-dimethyl-2-oxobutyl)hydrocinnamamido]imidazole-4-propionamide as a white foam, MS: 768 (M+H)+.

The (S)-N-[(1S,2S,4S,5S or R)-1-(cyclohexylmethyl)-2,5-dihydroxy-6-[4-(2-hydroxyethyl)-1-piperazinyl]-4-isopropylhexyl]-α-[(R)-α-(3,3-dimethyl-2-oxobutyl)hydrocinnamamido]-3-t-butoxycarbonylimidazole-4-propionamide used as the starting material was prepared as follows:

315.3 g (1.28 mmol) of t-butoxycarbonyl-L-phenylalanine methyl ester are hydrogenated in the presence of 5% rhodium on aluminium oxide at room temperature and 440 kPa according to the method described by J. Boger et al. in J. Med. Chem., 28, 1779 (1985), whereby there are obtained 315.3 g of methyl 2-t-butoxycarbonylamino-3-cyclohexylpropionate as an oil which is used directly in the next step.

750 ml (750 mmol) of a 20% solution of diisobutylaluminum hydride in hexane are added dropwise in the course of 90 minutes at −75° to 85.61 g (300 mmol) of methyl 2-t-butoxycarbonylamino-3-cyclohexylpropionate in 1.2 l of toluene. After completion of the addition the reaction mixture is stirred at −75° for a further 10 minutes. Subsequently, there are added dropwise, each within 25 minutes at a temperature of −75° to −70°, firstly 70 ml of methanol and then 840 ml of saturated potassium sodium tartrate solution. The milky reaction solution, warmed slowly to room temperature, is thereafter extracted with ether and the extracts are dried and evaporated, whereby there are obtained 82 g of 2-t-butoxycarbonylamino-3-cyclohexylpropylaldehyde as an oil which is used in the next step without furthe purification.

A solution of 179.7 g (1.01 mmol) of 4-bromo-3-isopropyl-1-butene (which had been prepared according to the method described by R. G. Helmquist in Tetrahendron Letters, 2533 (1982)) in 900 ml of ether is added dropwise within 2.5 hours to 24.65 g of magnesium shavings in 300 ml of ether in an argon atmosphere and at a temperature between 30° and the reflux temperature of the solvent. After completion of the addition the reaction mixture is heated to reflux for 3.5 hours. A solution of 82 g of 2-t-butoxycarbonylamino-3-cyclohexylpropylaldehyde in 900 ml of ether is added dropwise to the reaction mixture, cooled to −60°, within 75 minutes, whereby the temperature amounts to −60° to −70°. After completion of the addition the cooling bath is removed and the reaction mixture is stirred at room temperature under argon for 21 hours. It is then cooled to 5° and 225 ml of a saturated ammonium chloride solution are cautiously added thereto while stirring, whereby the temperature rises to 20°. The two phases are separated and the organic phase is dried over sodium sulphate and evaporated, whereby there are obtained 127.5 g of a yellow oil. Chromatographic separation of this oil on 2.5 kg of silica gel with methylene chloride which contains 2.5% ether as the eluting agent yields 33.9 g of ($\alpha$S,$\beta$S)-$\beta$-t-butoxycarbonylamino-$\alpha$-[(S)-2-isopropyl-3-butenyl]cyclohexylpropanol, 13.62 g of ($\alpha$S,$\beta$S)-$\beta$-t-butoxycarbonylamino-$\alpha$-[(R)-2-isopropyl-3-butenyl]cyclohexylpropanol as well as 35.5 g of a mixture of the two above-named diastereomers in the form of oils, MS: 354 (M+H)$^+$.

1.0 g (2.83 mmol) of ($\alpha$S,$\beta$S)-$\beta$-t-butoxycarbonylamino-$\alpha$-[(S)-2-isopropyl-3-butenyl]cyclohexylpropanol in 15 ml of 2,2-dimethoxypropane and 30 mg of p-toluenesulphonic acid is stirred at room temperature overnight. Thereafter, the reaction mixture is poured into 2N sodium bicarbonate solution and extracted three times with 150 ml of ether each time. The ether extracts are washed with water, combined, dried and evaporated, whereby there are obtained 1.2 g of t-butyl (4S,5S)-4-(cyclohexylmethyl)-5-[(S)-2-isopropyl-3-butenyl]-3-oxazolidinecarboxylate as an oil, MS: 393 (M+H)$^+$.

1.2 g (about 3 mmol) of t-butyl (4S,5S)-4-(cyclohexylmethyl)-5-[(S)-2-isopropyl-3-butenyl]-3-oxazolidinecarboxylate in 50 ml of methylene chloride are treated in succession with 1.2 g of sodium bicarbonate and 1.27 g of m-chloroperbenzoic acid (85%, 6 mmol). Thereafter, the reaction mixture is stirred at room temperature overnight, subsequently poured into 2N sodium bicarbonate solution and extracted twice with 200 ml of methylene chloride. The organic extracts are washed with 2N sodium bicarbonate solution and with water, combined, dried and evaporated. Chromatography of the residue (1.2 g) on 90 g of silica gel with a 98:2 mixture of toluene and ethyl acetate as the eluting agent yields 535 mg of t-butyl (4S,5S)-4-(cyclohexylmethyl)-5-[(2S,3R or S)-3,4-epoxy-2-isopropylbutyl]-2,2-dimethyl-3-oxazolidinecarboxylate as the more polar component and 465 mg of the epimeric compound t-butyl (4S,5S)-4-(cyclohexylmethyl)-5-[(2S,3S or R)-3,4-epoxy-2-isopropylbutyl]-2,2-dimethyl-3-oxazolidinecarboxylate as the less polar component, both as an oil, MS (both): 409 (M+H)$^+$.

In an analogous manner to that described in Example 1, t-butyl (4S,5S)-4-(cyclohexylmethyl)-5[(2S,3R or S)-3,4-epoxy-2-isopropylbutyl]-2,2-dimethyl-3-oxazolidinecarboxylate was converted into (S)-N-[(1S,2S,4S,5S or R)-1-(cyclohexylmethyl)-2,5-dihydroxy-6-[4-(2-hydroxyethyl)-1-piperazinyl]-4-isopropylhexyl]-$\alpha$-[(R)-$\alpha$-(3,3-dimethyl-2-oxobutyl)hydrocinnamamido]-3-t-butoxycarbonylimidazole-4-propionamide by reaction with N-hydroxyethylpiperazine with the formation of t-butyl (4S,5S)-4-(cyclohexylmethyl)-5-[(2S,3R or S)-3-hydroxy-4-[4-(2-hydroxyethyl)-1-piperazinyl]-2-isopropylbutyl]-2,2-dimethyl-3-oxazolidinecarboxylate (oil, MS: 539 (M+H)$^+$), cleavage of the Boc protecting group with hydrochloric acid in methanol with simultaneous opening of the oxazolidine ring and reaction with 1-(t-butoxycarbonyl)-N-[(R)-$\alpha$-(3,3-dimethyl-2-oxobutyl)hydrocinnamoyl]-L-histidine.

The 1-(t-butoxycarbonyl)-N-[(R)-$\alpha$-(3,3-dimethyl-2-oxobutyl)hydrocinnamoyl]-L-histidine which is also used as a starting material was prepared as follows:

A suspension of 3.0 g (12 mmol) of (R)-$\alpha$-(pivaloylmethyl)hydrocinnamic acid (see EPA 0,184,550) and 2.66 g (11 mmol) of L-histidine methyl ester dihydrochloride in 340 ml of dimethylformamide is treated at room temperature under a nitrogen atmosphere with 3.45 g (34 mmol) of triethylamine and 4.58 g (12 mmol) of HBTU. The reaction mixture is stirred at room temperature for 5 hours and subsequently evaporated in a high vacuum. The residue is dissolved in 500 ml of ethyl acetate and washed in succession with 100 ml of water, three times with 100 ml of saturated sodium bicarbonate solution each time and 100 ml of saturated sodium chloride solution. The organic phase is dried over sodium sulphate, evaporated under reduced pressure and the yellowish crude product obtained is chromatographed on silica gel with a 95:5 mixture of methylene chloride and methanol which contains 0.1% ammonia. In this manner there are obtained 3.6 g N-[(R)-$\alpha$-(3,3-dimethyl-2-oxobutyl)hydrocinnamoyl]-L-histidine methyl ester as a colourless foam, MS: 399 (M+H)$^+$.

A solution of 3.56 g (8.9 mmol) of N-[(R)-$\alpha$-(3,3-dimethyl-2-oxobutyl)hydrocinnamoyl]-L-histidine and 9.36 ml of 1N sodium hydroxide solution in 50 ml of methanol is stirred at room temperature for 15 hours and thereafter evaporated under reduced pressure in the cold. The residue is dissolved in 70 ml of dioxan and 30 ml of water, a solution of 2.95 g (13.5 mmol) of di-t-butyl dicarbonate in 100 ml of dioxan is added dropwise thereto at room temperature and the mixture is thereafter stirred at room temperature for 15 hours. For the working-up, the reaction solution is concentrated to about ⅓ of its volume under reduced pressure and then diluted with 200 ml of ethyl acetate. After the addition of 50 ml of ice-water, the reaction mixture is adjusted to pH 2.5 and the aqueous phase is saturated with solid sodium chloride. The aqueous phase is extracted twice with ethyl acetate and the combined ethyl acetate phases are dried over sodium sulphate and evaporated. The crude product obtained is chromatographed on silica gel with a 95:5 mixture of methylene chloride and methanol which contains 0.1% acetic acid, whereby there are obtained 3.5 g of 1-(t-butoxycarbonyl)-N-[(R)-α-(3,3-dimethyl-2-oxobutyl)hydrocinnamoyl]-L-histidine as a colourless powder, MS: 486 (M+H)+.

EXAMPLE 7

The following compounds were manufactured in an analogous manner to that described in Example 6:

From (S)-N-[(1S,2S,4S,5R or S)-6-(dibenzylamino)-1-(cyclohexylmethyl)-2,5-dihydroxy-4-isopropylhexyl]-α-[(R)-α-(3,3-dimethyl-2-oxobutyl)hydrocinnamamido]-3-t-butylcarbonylimidazole-4-propionamide the (S)-N-[(1S,2S,4S,5R or S)-6-(dibenzylamino)-1-(cyclohexylmethyl)-2,5-dihydroxy-4-isopropylhexyl]-α-[(R)-α-(3,3-dimethyl-2-oxobutyl)hydrocinnamamido]imidazole-4-propionamide as a foam, MS: 835 (M+H)+;

from (S)-N-[(1S,2S,4S,5R or S)-6-[4-(benzylamino)-piperidino]-1-(cyclohexylmethyl)-2,5-dihydroxy-4-isopropylhexyl]-α-[(R)-α-(3,3-dimethyl-2-oxobutyl)hydrocinnamamido]-3-t-butoxycarbonylimidazole-4-propionamide the (S)-N-[(1S,2S,4S,5R or S)-6-[4-(benzylamino)piperidino]-1-(cyclohexylmethyl)-2,5-dihydroxy-4-isopropylhexyl]-α-[(R)-α-(3,3-dimethyl-2-oxobutyl)hydrocinnamamido]imidazole-4-propionamide as a white solid, melting point 81° (dec., from methylene chloride/ether/hexane), MS: 828 (M+H)+, and from (S)-N-[(1S,2S,4S,5R or S)-6-azido-1-(cyclohexylmethyl)-2,5-dihydroxy-4-isopropylhexyl]-α-[(R)-α-(3,3-dimethyl-2-oxobutyl)hydrocinnamamido]-3-t-butoxycarbonylimidazole-4-propionamide the (S)-N-[(1S,2S,4S,5R or S)-6-azido-1-(cyclohexylmethyl)-2,5-dihydroxy-4-isopropylhexyl]-α-[(R)-α-(3,3-dimethyl-2-oxobutyl)hydrocinnamamido]imidazole-4-propionamide as a white foam, MS: 680 (M+H)+.

The propionamides used as the starting materials were prepared as follows in an analogous manner to that described in Example 6:

(S)-N-[(1S,2S,4S,5R or S)-6-(Dibenzylamino)-1-(cyclohexylmethyl)-2,5-dihydroxy-4-isopropylhexyl]-α-[(R)-α-(3,3-dimethyl-2-oxobutyl)hydrocinnamamido]-3-t-butylcarbonylimidazole-4-propionamide By reacting t-butyl (4S,5S)-4-(cyclohexylmethyl)-5-[(2S,3R or S)-3,4-epoxy-2-isopropylbutyl]-2,2-dimethyl-3-oxazolidinecarboxylate with N,N-dibenzylamine there was obtained t-butyl (4S,5S)-4-(cyclohexylmethyl)-5-[(2S,3R or S)-4-(dibenzylamino)-3-hydroxy-2-isopropylbutyl]-2,2-dimethyl-3-oxazolidinecarboxylate as an oil, MS: 606 (M+H)+, from which by cleaving off the Boc protecting group with simultaneous opening of the oxazoldine ring with hydrochloric acid in methanol and subsequently reacting with 1-(t-butoxycarbonyl)-N-[(R)-α-(3,3-dimethyl-2-oxobutyl)hydrocinnamoyl]-L-histidine there was prepared the above propionamide which was used in the next step without further purification.

(S)-N-[(1S,2S,4S,5R or S)-6-[4-(Benzylamino)piperidino]-1-(cyclohexylmethyl)-2,5-dihydroxy-4-isopropylhexyl]-α-[(R)-α-(3,3-dimethyl-2-oxobutyl)hydrocinnamamido]-3-t-butoxycarbonylimidazole-4-propionamide By reacting t-butyl (4S,5S)-4-(cyclohexylmethyl)-5-[(2S,3R or S)-3,4-epoxy-2-isopropylbutyl]-2,2-dimethyl-3-oxazolidinecarboxylate with 4-benzylaminopiperidine there was obtained t-butyl (4S,5S)-5-[(2S,3R or S)-4-[(benzylamino)piperidino]-3-hydroxy-2-isopropylbutyl]-4-(cyclohexylmethyl)-2,2-dimethyl-3-oxazolidinecarboxylate as an oil, MS: 599 (M+H)+, from which by cleaving off the Boc protecting group with simultaneous opening of the oxazolidine ring with hydrochloric acid in methanol and subsequently reacting with 1-(t-butoxycarbonyl)-N-[(R)-α-(3,3-dimethyl-2-oxobutyl)hydrocinnamoyl]-L-histidine there was prepared the above propionamide which was used directly in the next step without further purification.

(S)-N-[(1S,2S,4S,5R or S)-6-Azido-1-(cyclohexylmethyl)-2,5-dihydroxy-4-isopropylhexyl]-α-[(R)-α-(3,3-dimethyl-2-oxobutyl)hydrocinnamamido]-3t-butoxycarbonylimidazole-4-propionamide By reacting t-butyl (4S,5S)-4-(cyclohexylmethyl)-5-[(2S,3R or S)-3,4-epoxy-2-isopropylbutyl]-2,2-dimethyl-3-oxazolidinecarboxylate with ammonium azide there was obtained t-butyl (4S,5S)-5-[(2S,3R or S)-4-azido-3-hydroxy-2-isopropylbutyl]-4-(cyclohexylmethyl)-2,2-dimethyl-3-oxazolidinecarboxylate as a white foam, MS: 453 (M+H)+, from which by cleaving off the Boc protecting group with simultaneous opening of the oxazolidine ring with hydrochloric acid in methanol and subsequently reacting with 1-(t-butoxycarbonyl)-N-[(R)-α-(3,3-dimethyl-2-oxobutyl)hydrocinnamoyl]-L-histidine there was prepared the above propionamide which was used directly in the next step.

EXAMPLE 8

A mixture of 410 mg (1 mmol) of t-butyl [(1S,2S,4S,5RS)-1-(cyclohexylmethyl)-5,6-epoxy-2-hydroxy-4-isopropylhexyl]carbamate, 0.38 ml (2.5 mmol) of diethyl malonate, 3.02 ml (3.5 mmol) of 1.16N ethanolic sodium ethylate and 4 ml of ethanol is heated to reflux under argon for 8 hours. Thereafter, the reaction mixture is extracted three times with 150 ml of ethyl acetate each time and the organic extracts are washed twice with 70 ml of water each time, combined, dried over magnesium sulphate and evaporated. The residual oil (460 mg) is chromatographed on 30 g of silica gel with a 95:5 mixture of toluene and ethyl acetate as the eluting agent, whereby there are obtained 160 mg of an oil. In an analogous manner to that described in Example 6, this oil is treated with methanolic hydrochloric acid for the cleavage of the Boc protecting group with simultaneous opening of the oxazolidine ring and subsequently reacted with Boc-Phe-His(Boc)-OH (see U.S. Pat. No. 4,599,198). By cleaving off the Boc protecting group on the imidazole ring with potassium carbonate in methanol there are obtained 62 mg (27%) of t-butyl [(S)-α-[[(S)-1-[[(1S,2S,4S)-1-(cyclohexylmethyl)-2-hydroxy-5-methyl-4-[(2RS,4RS)-tetrahydro-4-(methoxycarbonyl)-5-oxo-2-furyl]hexyl]carbamoyl]-2-imidazol-4-ylethyl]carbamoyl]phenethyl]-carbamate as a white solid, melting point 95° (from methylene chloride/ether/hexane), MS: 754 (M+H)+.

EXAMPLE 9

174 mg (0.5 mmol) of (2S,3S,5S)-2-amino-1-cyclohexyl-5-isopropyl-7-phenoxy-3-heptanol are dissolved in 8 ml of acetonitrile, the solution is treated with 0.102 ml (0.5 mmol) of Hünig base, 220 mg (0.5 mmol) of BOP and 204 mg (0.5 mmol) of Boc-Phe-His-OH and the reaction mixture is stirred at room temperature for 3.5 hours. Thereafter, the mixture is taken up in ethyl acetate and the organic phase is washed once each time with 1N hydrochloric acid and 2N sodium carbonate solution, dried over sodium sulphate and evaporated under reduced pressure. Chromatography of the residue on silica gel with a 15:1 mixture of methylene chloride and methanol as the eluting agent yields 226 mg (60%) of t-butyl [(S)-α-[[1-[[(1S,2S,4S)-1-(cyclohexylmethyl)-2-hydroxy-4-isopropyl-6-phenoxyhexyl]carbamoyl]-2-imidazol-4-ylethyl]carbamoyl]phenethyl]-carbamate as a resin, MS: 732 (M+H)+.

The (2S,3S,5S)-2-amino-1-cyclohexyl-5-isopropyl-7-phenoxy-3-heptanol used as the starting material was prepared as follows:

8.0 g (22.6 mmol) of (αS,βS)-β-t-butoxycarbonylamino-α-[(S)-2-isopropyl-3-butenyl]cyclohexylpropanol are dissolved in 50 ml of 2.2-dimethoxypropane, treated with 0.8 g of p-toluenesulphonic acid hydrate and stirred at room temperature overnight. The crude product (5.34 g; 13.56 mmol) obtained after the usual working-up is dissolved in 200 ml of hexane, treated dropwise rapidly with 0.5 ml of boranedimethyl sulphide complex (5 mmol based on borohydride) while cooling with ice and thereafter heated to reflux for 1 hour. Then, the reaction mixture is allowed to cool to room temperature, 30 ml of ethanol and 1.67 ml of 3N sodium hydroxide solution are added thereto in succession and finally 1.67 ml of 30% hydrogen peroxide are added dropwise thereto while cooling with ice. After completion of the addition the reaction solution is heated to reflux for 1 hour. Thereafter, the reaction solution is poured into 200 ml of water, extracted with ethyl acetate, the extracts are dried over sodium sulphate and evaporated to dryness under reduced pressure. Flash chromatography of the residue on silica gel with 1:1 mixture of ether and petroleum ether as the eluting agent yields 4 g (71%) of t-butyl 4-(cyclohexylmethyl)-5-(4-hydroxy-2-isopropylbutyl)-2,2-dimethyl-3-oxazolidinecarboxylate as a pale yellow solid, MS: 396 (M-CH3)+.

A solution of 1.0 g (2.43 mmol) of t-butyl 4-(cyclohexylmethyl)-5-(4-hydroxy-2-isopropylbutyl)-2,2-dimethyl-3-oxazolidinecarboxylate in 70 ml of tetrahydrofuran is treated in succession with 0.637 g (2.56 mmol) of triphenylphosphine and 228 mg (2.43 mmol) of phenol. Thereto there is added dropwise within 5 minutes 0.418 g (2.42 mmol) of diethyl azodicarboxylate in 10 ml of tetrahydrofuran. Thereafter, the reaction mixture is stirred at room temperature for 20 hours, subsequently evaporated under reduced pressure and finally treated with a mixture of ether and petroleum ether. Thereafter, the separated solid is filtered off and the filtrate is evaporated under reduced pressure. Flash chromatography of the residue on silica gel with a 2:3 mixture of ether and petroleum ether as the eluting agent yields 459 mg (39%) of t-butyl (4S,5S)-4-(cyclohexylmethyl)-5-[(S)-2-isopropyl-4-phenoxybutyl)-2,2-dimethylbutyl-3-oxazolidinecarboxylate as a pale yellow resin, MS: 486 (M-CH3)+.

450 mg (0.9 mmol) of t-butyl (4S,5S)-4-(cyclohexylmethyl)-5-[(S)-2-isopropyl-4-phenoxybutyl)-2,2-dimethylbutyl-3-oxazolidinecarboxylate are dissolved in 1.5 ml of methylene chloride and treated with 1.5 ml of trifluoroacetic acid and 0.15 ml of water. The reaction mixture is subsequently stirred at room temperature for 4.5 hours and thereafter poured into 2N sodium bicarbonate solution. The aqueous solution is extracted with ethyl acetate and the organic extracts are dried over sodium sulphate and evaporated under reduced pressure. Chromatography of the residue on silica gel with a 10:1 mixture of methylene chloride and methanol as the eluting agent yields 182 mg (58%) of (2S, 3S, 5S)-2-amino-1-cyclohexyl-5-isopropyl-7-phenoxy-3-heptanol as a resin, MS: 348 (M+H)+.

EXAMPLE 10

The following compounds were manufactured in an analogous manner to that described in Example 9:

From 100 mg (0.37 mmol) of (3S,5S,6S)-6-amino-7-cyclohexyl-5-hydroxy-3-isopropyl-1-heptanol by reaction with 160 mg (0.4 mmol) of Boc-Phe-His-OH 56 mg (27%) of t-butyl [(S)-α-[[(S)-1-[[(1S, 2S, 4S)-1-(cyclohexylmethyl)-2,6-dihydroxy-4-isopropylhexyl]carbamoyl]-2-imidazol-4-ylethyl]carbamoyl]phenethyl]-carbamate as an amorphous solid, MS: 656 (M+H)+;

from 109 mg (0.4 mmol) of (3S,5S,6S)-6-amino-7-cyclohexyl-5-hydroxy-3-isopropylheptyl propionate by reaction with 200 mg (0.5 mmol) of Boc-Phe-His-OH 94 mg (33%) of t-butyl [(S)-α-[[(S)-1-[[(1S,2S,4S)-1-(cyclohexylmethyl)-2-hydroxy-4-isopropyl-6-(propionyloxy)hexyl]carbamoyl]-2-imidazol-4-ylethyl]carbamoyl]phenethyl]carbamate as a resin, MS: 712 (M+H)+, and from 90 mg (0.248 mmol) of (2S,3S,5S)-2-amino-7-(benzyloxy)-1-cyclohexyl-5-isopropyl-3-heptanol by reaction with 102mg (0.248 mmol) of Boc-Phe-His-OH 50 mg (27%) of t-butyl [(S)-α-[[(RS)-1-[[(1S,2S,4S)-6-(benzyloxy)-1-(cyclohexylmethyl)-2-hydroxy-4-isopropylhexyl]carbamoyl]-2-imidazol-4-ylethyl]carbamoyl]phenethyl]carbamate as a resin, MS: 746 (M+H)+.

The amines used as starting materials were prepared as follows:

(3S,5S,6S)-6-Amino-7-cyclohexyl-5-hydroxy-3-isopropyl-1-heptanol 1.1 g (2.67 mmol) of t-butyl 4-(cyclohexylmethyl)-5-(4-hydroxy-2-isopropylbutyl)-2,2-dimethyl-3-oxazolidinecarboxylate are dissolved in 1.85N hydrochloric acid in dioxan and stirred at room temperature for 2 hours. Thereafter, the reaction mixture is poured into 2N potassium bicarbonate solution and extracted with ethyl acetate. The crude product obtained after drying and evaporating the organic extracts is chromatographed on silica gel with a 4:1 mixture of methylene chloride and methanol as the eluting agent, whereby there are obtained 268 mg (37%) of (3S,5S,6S)-6-amino-7-cyclohexyl-5-hydroxy-3-isopropyl-1-heptanol as a resin, MS: 272 (M+H)+.

(3S,5S,6S)-6-Amino-7-cyclohexyl-5-hydroxy-3-isopropylheptyl propionate 1.0 g (2.43 mmol) of t-butyl 4-(cyclohexylmethyl)-5-(4-hydroxy-2-isopropylbutyl)-2,2-dimethyl-3-oxazolidinecarboxylate in 50 ml of methylene chloride is treated with 0.38 ml (2.7 mmol) of triethylamine and 0.24 ml (2.7 mmol) of propionyl chloride and stirred at room temperature for 12 hours. After the usual working-up the crude product is purified by flash chromatography on silica gel with a 1:5 mixture of ether and petroleum ether, whereby there is obtained 1.0 g (88%) of t-butyl (4S,5S)-4-(cyclohexylmethyl)-5-[(S)-2-isopropyl-4-(propionyloxy)butyl]-2,2-dimethyl-3-oxazolidinecarboxylate as an oil, MS: 452 (M−CH$_3$)$^+$.

From 950 mg (2.03 mmol) of t-butyl (4S,5S)-4-(cyclohexylmethyl)-5-[(S)-2-isopropyl-4-(propionyloxy)butyl]-2,2-dimethyl-3-oxazolidinecarboxylate there are obtained by cleaving off the Boc protecting group with trifluoroacetic acid in an analogous manner to that described in Example 9 392 mg (59%) of (3S,5S,6S)-6-amino-7-cyclohexyl-5-hydroxy-3-isopropylheptyl propionate as a resin, MS: 328 (M+H)$^+$.

(2S,3S,5S)-2-Amino-7-(benzyloxy)-1-cyclohexyl-5-isopropyl-3-heptanol

A mixture of 500 mg (1.2 mmol) of t-butyl 4-(cyclohexylmethyl)-5-(4-hydroxy-2-isopropylbutyl)-2,2-dimethyl-3-oxazolidinecarboxylate in 3 ml of toluene, 191 mg (0.5 mmol) of tetrabutylammonium iodide, 5.9 g (150 mmol) of sodium hydroxide in water (8.8 ml) and 1.16 ml (9.8 mmol) of benzyl bromide is stirred at room temperature for 24 hours. Thereafter, water is added thereto, the mixture is extracted with ether, the ether extracts are dried over sodium sulphate and evaporated to dryness under reduced pressure. Chromatography of the residue on silica gel with a 1:8 mixture of ether and petroleum ether yields 457 mg (78.5%) of t-butyl (4S,5S)-5-[(S)-2-(benzyloxy)-2-isopropylbutyl]-4-(cyclohexylmethyl)-2,2-dimethyl-3-oxazolidinecarboxylate as a pale yellow resin, MS: 486 (M−CH$_3$)$^+$.

From 450 mg (0.9 mmol) of t-butyl (4S,5S)-5-[(S)-2-(benzyloxy)-2-isopropylbutyl]-4-(cyclohexylmethyl)-2,2-dimethyl-3-oxazolidinecarboxylate there are obtained by cleaving off the Boc protecting group with trifluoroacetic acid in an analogous manner to that described in Example 9 100 mg (29%) of (2S,3S,5S)-2-amino-7-(benzyloxy)-1-cyclohexyl-5-isopropyl-3-heptanol as a resin, MS: 264 (M-cyclohexylmethyl)$^+$.

EXAMPLE 11

In an analogous manner to that described in Example 9, 635 mg (1.78 mmol) of t-butyl [(4S,5S)-4-(cyclohexylmethyl)-5-(S)-2-isopropyl-4-(pivaloyloxy)butyl]-2,2-dimethyl-3-oxazolidinecarboxylate are treated with trifluoroacetic acid/water/methylene chloride for the cleavage of the Boc protecting group with simultaneous opening of the oxazolidine ring and the resulting 347 mg (76%) of (3S,5S,6S)-6-amino-7-cyclohexyl-5-hydroxy-3-isopropylheptyl pivaloate are reacted without further purification with Boc-Phe-His-OH, whereby there are obtained 280 mg (37%) of t-butyl [(S)-α-[[(RS)-1-[[(1S,2S,4S)-1-(cyclohexylmethyl)-2-hydroxy-4-isopropyl-6-(pivaloyloxy)hexyl]carbamoyl]-2-imidazole-4-ylethyl]carbamoyl]phenethyl]carbamate as an amorphous solid, MS: 740 (M+H)$^+$.

In an analogous manner to that described above, from 270 mg (0.53 mmol) of (S)-4-[(4S,5S)-3-(t-butoxycarbonyl)-4(cyclohexylmethyl)-2,2-dimethyl-5-oxazolidinyl]-[3-isopropylbutyl]butylcarbamate there were obtained 80 mg (25%) [(3S,5S,6S)-6-[[N-[N-(t-butoxycarbonyl)-3-phenyl-L-alanyl]-DL-histidyl-]amino]-7-cyclohexyl-5-hydroxy-3-isopropylheptyl]-butylcarbamate as a resin, MS: 755 (M+H)$^+$.

The t-butyl [(4S,5S)-4-(cyclohexylmethyl)-5-(S)-2-isopropyl-4-(pivaloyloxy)butyl]-2,2-dimethyl-3-oxazolidinecarboxylate used as the starting material was prepared as follows:

630 mg (1.53 mmol) of t-butyl 4-(cyclohexylmethyl)-5-(4-hydroxy-2-isopropylbutyl)-2,2-dimethyl-3-oxazolidinecarboxylate in 20 ml of methylene chloride are treated with 0.234 ml (1.7 mmol) of triethylamine and 0.206 ml (1.7 mmol) of pivaloyl chloride and subsequently stirred at room temperature for 12 hours. The crude product obtained after the usual working-up is purified by flash chromatography on silica gel with a 1:5 mixture of ether and petroleum ether as the eluting agent, whereby there are obtained 635 mg (83%) of t-butyl [(4S,5S)-4-(cyclohexylmethyl)-5-(S)-2-isopropyl-4-(pivaloyloxy)butyl]-2,2-dimethyl-3-oxazolidinecarboxylate as a resin, MS: 480 (M−CH$_3$)$^+$.

The (S)-4-[(4S,5S)-3-(t-butoxycarbonyl)-4-(cyclohexylmethyl)-2,2-dimethyl-5-oxazolidinyl]-[3-isopropylbutyl]butylcarbamate used as the starting material was prepared as follows:

411 mg (1.0 mmol) of t-butyl 4-(cyclohexylmethyl)-5-(4-hydroxy-2-isopropylbutyl)-2,2-dimethyl-3-oxazolidinecarboxylate in 5 ml of ether are treated with a catalytic amount of triethylamine (about 0.1 mmol) and 0.22 ml (2.0 mmol) of butyl isocyanate in 5 ml of tetrahydrofuran and subsequently heated to reflux for 72 hours. Thereafter, the reaction solution is evaporated under reduced pressure and the residue, for purification, is flash-chromatographed on silica gel with a 1:1 mixture of ether and petroleum ether, whereby there are obtained 275 mg (54%) of (S)-4-[(4S,5S)-3-(t-butoxycarbonyl)-4-(cyclohexylmethyl)-2,2-dimethyl-5-oxazolidinyl]-[3-isopropylbutyl]butylcarbamate as a resin, MS: 495 (M−CH$_3$)$^+$.

EXAMPLE 12

The Boc protecting group is cleaved off from 180 mg (0.245 mmol) of t-butyl [(S)-α-[[1-[[(1S,2S,4S)-1-(cyclohexylmethyl)-2-hydroxy-4-isopropyl-6-phenoxyhexyl]carbamoyl]-2-imidazol-4-ylethyl]carbamoyl]phenethyl]carbamate with 1.8N hydrochloric acid in dioxan in analogy to Example 10. The thus-obtained free amine is dissolved in 5 ml of acetonitrile and treated in succession with 41 µl (0.2 mmol) of Hünig base. 88 mg (0.2 mmol) of BOP and 43 mg (0.2 mmol) of Boc-D-Pro-OH and subsequently stirred at room temperature for 20 hours. The crude product obtained after the usual working-up is chromatographed on silica gel with a 10:1 mixture of methylene chloride and methanol as the eluting agent, whereby there are obtained 107 mg (64%) of t-butyl (R)-[[(S)-1-[[1-[[(1S,2S,4S)-1-(cyclohexylmethyl)-2-hydroxy-4-isopropyl-6-phenoxyhexyl]carbamoyl]-2-imidazol-4-ylethyl]]carbamoyl]phenethyl]carbamoyl]-1-pyrrolidinecarboxylate as an amorphous solid, MS: 829 (M+H)$^+$.

In an analogous manner to that described above, from 240 mg (0.324 mmol) of t-butyl [(S)-α-[[(RS)-1-[[(1S,2S,4S)-1-(cyclohexylmethyl)-2-hydroxy-4-isopropyl-6-(pivaloyloxy)hexyl]carbamoyl]-2-imidazol-4-ylethyl]carbamoyl]phenethyl]carbamate there were obtained 124 mg (50%) of t-butyl (R)-2-[[(S)-α-[[(R and S)-1-[[(1S,2S,4S)-1-(cyclohexylmethyl)-2-hydroxy-4-isopropyl-6-(pivaloyloxy)hexyl]carbamoyl]-2-imidazol-4-ylethyl]-carbamoyl]phenethyl]carbamoyl]-1-pyrrolidinecarboxylate as an amorphous solid, MS: 740 (M+H)$^+$.

EXAMPLE 13

The following compounds were manufactured in an analogous manner to that described in Example 6 by cleaving off the Boc protecting group on the imidazole ring with potassium carbonate in methanol:

From (S)-N-[(1S,2S,4S,E)-6-(butylcarbamoyl)-1-(cyclohexylmethyl)-2-hydroxy-4-isopropyl-5-hexenyl]-α-[(R)-α-(3,3-dimethyl-2-oxobutyl)hydrocinnamamido]-3-t-butoxycarbonylimidazole-4-propionamide the (S)-N-[(1S,2S,4S,E)-6-(butylcarbamoyl)-1-(cyclohexylmethyl)-2-hydroxy-4-isopropyl-5-hexenyl]-α-[(R)-α-(3,3-dimethyl-2-oxobutyl)hydrocinnamamido]-imidazole-4-propionamide as a yellowish amorphous solid, MS: 720 $(M+H)^+$;

from (S)-N-[(1S,2S,4S,E)-1-(cyclohexylmethyl)-2-hydroxy-4-isopropyl-6-[(2-pyridylmethyl)carbamoyl]-5-hexenyl]-α-[(R)-α-(3,3-dimethyl-2-oxobutyl)hydrocinnamamido]-3-t-butoxycarbonyl]imidazole-4-propionamide the (S)-N-[(1S,2S,4S,E)-1-(cyclohexylmethyl)-2-hydroxy-4-isopropyl-6-[(2-pyridylmethyl)carbamoyl]-5-hexenyl]-α-[(R)-α-(3,3-dimethyl-2-oxobutyl)hydrocinnamamido]imidazole-4-propionamide as a white amorphous solid, MS: 755 $(M+H)^+$;

from (S)-N-[(1S,2S,4S)-1-(cyclohexylmethyl)-2-hydroxy-4-isopropyl-6-methyl-5-heptenyl]-α-[(R)-α-(3,3-dimethyl-2-oxobutyl)hydrocinnamamido]-3-t-butoxycarbonylimidazole-4-propionamide the (S)-N-(1S,2S,4S)-1-(cyclohexylmethyl)-2-hydroxy-4-isopropyl-6-methyl-5-heptenyl]-α-[(R)-α-(3,3-dimethyl-2-oxobutyl)hydrocinnamamido]imidazole-4-propionamide as an amorphous solid, MS: 649 $(M+H)^+$;

from (S)-N-[(1S,2S,4S,E)-1-(cyclohexylmethyl)-2-hydroxy-4-isopropyl-6-(2-pyridyl)-5-hexenyl]-α-[(R)-α-(3,3-dimethyl-2-oxobutyl)hydrocinnamamido]-3-t-butoxycarbonylimidazole-4-propionamide the (S)-N-[(1S,2S,4S,E)-1-(cyclohexylmethyl)-2-hydroxy-4-isopropyl-6-(2-pyridyl)-5-hexenyl]-α-[(R)-α-3,3-dimethyl-2-oxobutyl]hydrocinnamamido]imidazole-4-propionamide as a white amorphous solid, MS: 698 $(M+H)^+$, and from (S)-N-[(1S,2S,4S,E)-1-(cyclohexylmethyl)-2-hydroxy-4-isopropyl-6-phenyl-5-hexenyl]-α[(R)-α-(3,3-dimethyl-2-oxobutyl)hydrocinnamamido]-3-t-butoxycarbonylimidazole-4-propionamide the (S)-N-[(1S,2S,4S,E)-1-(cyclohexylmethyl)-2-hydroxy-4-isopropyl-6-phenyl-5-hexenyl]-α-[(R)-α-(3,3-dimethyl-2-oxobutyl)hydrocinnamamido]imidazole-4-propionamide as a white amorphous solid, MS: 697 $(M+H)^+$.

The propionamides used as the starting materials were prepared as follows:

(S)-N-[(1S,2S,4S,E)-6-(Butylcarbamoyl)-1-(cyclohexylmethyl)-2-hydroxy-4-isopropyl-5-hexenyl]-α-[(R)-α-(3,3-dimethyl-2-oxobutyl)hydrocinnamamido]-3-t-butoxycarbonylimidazole-4-propionamide 0.5 g (2 mmol) of osmium tetroxide are covered with 25 ml of distilled water and thereafter treated with 9.6 g (82 mmol) of N-methylmorpholine N-oxide. Then, 25 ml of water and 50 ml of acetone are added to this mixture and the reaction mixture is cooled to 5°. While stirring and cooling there are then added dropwise within 40 minutes 20.0 g (50.8 mmol) of t-butyl (4S,5S)-4-(cyclohexylmethyl)-5-[(S)-2-isopropyl-3-butenyl]-3-oxazolidinecarboxylate in 70 ml of acetone. After completion of the addition the cooling bath is removed and the reaction mixture is stirred for a further 20 hours. Thereafter, a suspension of 2.5 g (13 mmol) of sodium pyrosulphite and 16.6 g of Florisil in 80 ml of water is added and the mixture is stirred intensively at room temperature for a further 2 hours. Subsequently, the reaction mixture is filtered through Dicalit and the filtrate is neutralized to pH 7 with aqueous potassium bisulphate solution. After evaporating the organic solvent the aqueous phase is extracted with ethyl acetate and the ethyl acetate extracts are dried over sodium sulphate and evaporated. The residue remaining is chromatographed on 300 g of silica gel with a mixture of methylene chloride and isopropanol as the eluting agent, whereby there are obtained 19.5 g of t-butyl (4S,5S)-4-(cyclohexylmethyl)-5-[(2S,3RS)-3,4-dihydroxy-2-isopropylbutyl]-2,2-dimethyl-3-oxazolidinecarboxylate as an oil which is used in the next step without further purification.

20.0 g (46.8 mmol) of t-butyl (4S,5S)-4-(cyclohexylmethyl)-5-[(2S,3RS)-3,4-dihydroxy-2-isopropylbutyl]-2,2-dimethyl-3-oxazolidinecarboxylate are dissolved in 250 ml of benzene, cooled to 5° and treated portionwise within 10 minutes with 20.8 g (47 mmol) of lead tetraacetate. After stirring at 5° for 4 hours 500 ml of ether are added and the reaction mixture is stirred for a further 15 minutes. Thereafter, the reaction mixture is filtered and the filtrate is evaporated under reduced pressure. Chromatography of the residue on 300 g of silica gel with methylene chloride as the eluting agent yields 15.9 g of t-butyl (4S,5S)-4-(cyclohexylmethyl)-5-[(S)-2-formyl-3-methylbutyl]-2,2-dimethyl-3-oxazolidinecarboxylate as an oil, MS: 380 $(M-CH_3)^+$.

330 mg of a sodium hydride suspension (55% in mineral oil) are washed free from oil with hexane and subsequently covered with 15 ml of tetrahydrofuran. The suspension is thereafter cooled to 0° and treated dropwise with a solution of 2.25 ml (11 mmol) of triethyl phosphonoacetate in 5 ml of tetrahydrofuran. After completion of the addition the reaction mixture is stirred at room temperature for 30 minutes, then again cooled to 0° and treated dropwise within 10 minutes with 1.50 g (3.8 mmol) of t-butyl (4S,5S)-4-(cyclohexylmethyl)-5-[(S)-2-formyl-3-methylbutyl]-2,2-dimethyl-3-oxazolidinecarboxylate in 10 ml of tetrahydrofuran. After completion of the addition the reaction mixture is stirred at 0° for 0.5 hour and subsequently at room temperature for 2 hours. Thereafter, the mixture is poured into ice-water and extracted with ethyl acetate. The ethyl acetate extracts are dried over magnesium sulphate and evaporated under reduced pressure. Chromatography of the residue on 30 g of silica gel with a mixture of methylene chloride and isopropanol as the eluting agent yields 1.7 g of ethyl (S)-5-[(4S,5S)-3-(t-butoxycarbonyl)-4-(cyclohexylmethyl)-2,2-dimethyl-5-oxazolidinyl]-4-isopropyl-2-pentenoate which is used in the next step without further purification.

1.7 g (3.7 mmol) of ethyl (S)-5-[(4S,5S)-3-(t-butoxycarbonyl)-4-(cyclohexylmethyl)-2,2-dimethyl-5-oxazolidinyl]-4-isopropyl-2-pentenoate are dissolved in 10 ml of methanol, treated with 2 ml (18 mmol) of 28% sodium hydroxide solution and stirred at room temperature for 16 hours. Thereafter, the reaction mixture is poured into ice-water, the pH value is adjusted to 5 with acetic acid and the mixture is extracted with ethyl acetate. The ethyl acetate extracts are dried over magnesium sulphate and evaporated under reduced pressure. Chromatography of the residue on 20 g of silica gel with a mixture of methylene chloride and isopropanol as the eluting agent yields 1.2 g of (S)-5-[(4S,5S)-3-(t- butoxycarbonyl)-4-(cyclohexylmethyl)-2,2-dimethyl-5-oxazolidinyl]-4-isopropyl-2-pentenoic acid as an oil, MS: 422 (M−CH₃)⁺.

A mixture of 0.55 g (1.26 mmol) of (S)-5-[(4S,5S)-3-(t-butoxycarbonyl)-4-(cyclohexylmethyl)-2,2-dimethyl-5-oxazolidinyl]-4-isopropyl-2-pentenoic acid, 0.22 g (1.6 mmol) of HOBT, 0.14 ml (1.4 mmol) of butylamine and 8 ml of methylene chloride is cooled to 0° and treated dropwise with a solution of 0.29 g (1.5 mmol) of EDC in 2 ml of dimethylformamide. Thereafter, the reaction mixture is stirred at 0° for 1 hour and subsequently at room temperature for 16 hours and then poured into ice-water and extracted with methylene chloride. The methylene chloride extracts are dried over potassium carbonate and evaporated under reduced pressure. Chromatography of the residue obtained on 10 g of silica gel with a mixture of methylene chloride and isopropanol as the eluting agent yields 0.53 g of t-butyl (4S,5S)-5-[(S,E)-4-(butylcarbamoyl)-2-isopropyl-3-butenyl]-4-(cyclohexylmethyl)-2,2-dimethyl-3-oxazolidinecarboxylate as a pale yellow oil which is used directly in the next step without further purification.

0.53 g (1.07 mmol) of t-butyl (4S,5S)-5-[(S,E)-4-(butylcarbamoyl)-2-isopropyl-3-butenyl]-4-(cyclohexylmethyl)-2,2-dimethyl-3-oxazolidinecarboxylate is dissolved in 18.2 ml of methanol and treated at 10° with 6.4 ml of 3.88M hydrochloric acid in methanol. The reaction mixture is subsequently stirred at room temperature for 5 hours and thereafter evaporated. The residue is dissolved in methylene chloride and the methylene chloride solution is washed with 2N sodium bicarbonate solution, dried over potassium carbonate and evaporated under reduced pressure. In this manner there is obtained 0.314 g of (E,4S,6S,7S)-7-amino-N-butyl-8-cyclohexyl-6-hydroxy-4-isopropyl-2-octenamide as an oil which is used in the next step without further purification.

In an analogous manner to that described in Example 6, by reacting (E,4S,6S,7S)-7-amino-N-butyl-8-cyclohexyl-6-hydroxy-4-isopropyl-2-octenamide with 1-(t-butoxycarbonyl)-N-[(R)-α(3,3-dimethyl-2-oxobutyl)hydrocinnamoyl]-L-histidine there is obtained (S)-N-[(1S,2S,4S,))-6-(butylcarbamoyl)-1-(cyclohexylmethyl)-2-hydroxy-4-isopropyl-5-hexenyl]-α-[(R)-α-(3,3-dimethyl-2-oxobutyl)hydrocinnamamido]-3-t-butoxycarbonylimidazole-4-propionamide which is used directly in the next step without further purification.

(S)-N-[(1S,2S,4S,E)-1-(Cyclohexylmethyl)-2-hydroxy-4-isopropyl-6-[(2-pyridylmethyl)carbamoyl]-5-hexenyl]-α-[(R)-α-(3,3-dimethyl-2-oxobutyl)hydrocinnamamido]-3-t-butoxycarbonylimidazole-4-propionamide This compound was prepared in an analogous manner to that described above by reacting (S)-5-[(4S,5S)-3-(t-butoxycarbonyl)-4-(cyclohexylmethyl)-2,2-dimethyl-5-oxazolidinyl]-4-isopropyl-2-pentenoic acid with 2-pyridylmethylamine, subsequently cleaving off the Boc protecting group with the simultaneous opening of the oxazolidine ring with hydrochloric acid in methanol and reacting with 1-(t-butoxycarbonyl)-N-[(R)-α-(3,3-dimethyl-2-oxobutyl)hydrocinnamoyl]-L-histidine.

(S)-N-[(1S,2S,4S)-1-(Cyclohexylmethyl)-2-hydroxy-4-isopropyl-6-methyl-5-heptenyl]-α-[(R)-α-(3,3-dimethyl-2-oxobutyl)hydrocinnamamido]-3-t-butoxycarbonylimidazole-4-propionamide 2.60 g (6 mmol) of isopropyltriphenylphosphonium iodide are suspended in 20 ml of tetrahydrofuran, cooled to −10° and treated while stirring with 3.5 ml (5.6 mmol) of 1.6M butyllithium solution in hexane. Thereafter, the reaction mixture is stirred at room temperature for 1 hour, then cooled to −65° and treated dropwise with a solution of 1.58 g (4.0 mmol) of t-butyl (4S,5S)-4-(cyclohexylmethyl)-5-[(S)-2-formyl-3-methylbutyl]-2,2-dimethyl-3-oxazolidinecarboxylate in 10 ml of tetrahydrofuran. Thereafter, the reaction mixture is stirred for 2 hours without cooling and subsequently poured into ice-water and extracted with methylene chloride. The methylene chloride extracts are dried over magnesium sulphate and evaporated. Chromatography of the residue on 20 g of silica gel with methylene chloride as the eluting agent yields 1.02 g of t-butyl (4S,5S,)-4-(cyclohexylmethyl)-5-[(S)-2-isopropyl-4-methyl-3-pentenyl]-2,2-dimethyl-3-oxazolidinecarboxylate as an oil, MS: 421 (M+H)⁺.

1.0 g (2.37 mmol) of t-butyl (4S,5S,)-4-(cyclohexylmethyl)-5-[(S)-2-isopropyl-4-methyl-3-pentenyl]-2,2-dimethyl-3-oxazolidinecarboxylate is dissolved in 40 ml of methanol and treated with 12.9 ml (50 mmol) of 3.9M hydrochloric acid in methanol. Thereafter, the reaction mixture is stirred at room temperature for 3.5 hours and subsequently evaporated under reduced pressure. The residue is dissolved in methylene chloride and the methylene chloride solution is washed with 2N sodium bicarbonate solution, dried over potassium carbonate and evaporated under reduced pressure. Chromatography of the residue on 10 g of silica gel with a mixture of methylene chloride and isopropanol as the eluting agent yields 0.377 g of (αS,βS)-β-amino-α-[(S)-2isopropyl-4-methyl-3-pentenyl]cyclohexylpropanol as an oil, MS: 282 (M+H)⁺.

In an analogous manner to that described in Example 6, (αS,βS)-β-amino-α-[(S)-2-isopropyl-4-methyl-3-pentenyl]cyclohexylpropanol is reacted with 1-(t-butoxycarbonyl)-N-[(R)-α-(3,3-dimethyl-2-oxobutyl)hydrocinnamoyl]-L-histidine to give (S)-N-[(1S,2S,4S)-1-(cyclohexylmethyl)-2-hydroxy-4-isopropyl-6-methyl-5-heptenyl]-α-[(R)-α-(3,3-dimethyl-2-oxobutyl)hydrocinnamamido]-3-t-butoxycarbonylimidazole-4-propionamide which is used directly in the next step.

(S)-N-[(1S,2S,4S,E)-1-(Cyclohexylmethyl)-2-hydroxy-4-isopropyl-6-(2-pyridyl)-5-hexenyl]-α-[(R)-α-(3,3-dimethyl-2-oxobutyl)hydrocinnamamido]-3-t-butoxycarbonylimidazole-4-propionamide This compound was prepared in an analogous manner to that described above by reacting t-butyl (4S,5S)-4-(cyclohexylmethyl)-5-[(S)-2-formyl-3-methylbutyl]-2,2-dimethyl-3-oxazolidinecarboxylate with 2-pyridylmethyl-triphenylphosphonium iodide, cleaving off the Boc protecting group with simultaneous opening of the oxazolidine ring with hydrochloric acid in methanol and reacting the resulting (2S,3S,5S)-2-amino-1-cyclohexyl-5-isopropyl-7-(2-pyridyl)-6-hepten-3-ol with 1-(t-butoxycarbonyl)-N-[(R)-α-(3,3-dimethyl-2-oxobutyl)hydrocinnamoyl]-L-histidine.

(S)-N-[(1S,2S,4S,E)-1-(Cyclohexylmethyl)-2-hydroxy-4-isopropyl-6-phenyl-5-hexenyl]-α-[(R)-α-(3,3-dimethyl-2-oxobutyl)hydrocinnamamido]-3-t-butoxycarbonylimidazole-4-propionamide This compound was also prepared in an analogous manner to that described above by reacting t-butyl (4S,5S)-4-(cyclohexylmethyl)-5-[(S)-2-formyl-3-methylbutyl]-2,2-dimethyl-3-oxazolidinecarboxylate with benzyl-triphenylphosphonium iodide, cleaving off the Boc protecting group with simultaneous opening of the oxazolidine ring with hydrochloric acid in methanol and reacting the resulting (αS,βS)-β-amino-α-[(S,E)-2-isopropyl-4-phenyl-3-butenyl]cyclohexylpropanol with 1-(t-butoxycarbonyl)-N-[(R)-α-(3,3-dimethyl-2-oxobutyl)hydrocinnamoyl]-L-histidine.

EXAMPLE 14

150 mg (0.22 mmol) of (S)-N-[(1S,2S,4S,E)-1-(cyclohexylmethyl)-2-hydroxy-4-isopropyl-6-(2-pyridyl)-5-hexenyl]-α-[(R)-α-3,3-dimethyl-2-oxobutyl]hydrocinnamamido]imidazole-4-propionamide are dissolved in 5 ml of methanol, treated with 0.15 ml (0.6 mmol) of 3.9M hydrochloric acid in methanol and 80 mg of palladium on charcoal (10%) and hydrogenated for 6 hours at room temperature and atmospheric pressure. After completion of the hydrogen uptake the catalyst is filtered off and the filtrate is evaporated under reduced pressure. There are thus obtained 150 mg of (S)-N-[(1S,2S,4S)-1-(cyclohexylmethyl)-2-hydroxy-4-isopropyl-6-(2-pyridyl)hexyl]-α-[(R)-α-(3,3-dimethyl-2-oxobutyl)hydrocinnamamido]imidazole-4-propionamide dihydrochloride as an amorphous solid, MS: 700 (M+H)+.

The following compounds were manufactured in an analogous manner to that described above:

From (S)-N-[(1S,2S,4S,E)-1-(cyclohexylmethyl)-2-hydroxy-4-isopropyl-6-phenyl-5-hexenyl]-α-[(R)-α-(3,3-dimethyl-2-oxobutyl]hydrocinnamamido]-imidazole-4-propionamide the (S)-N-[(1S,2S,4S)-1-(cyclohexylmethyl)-2-hydroxy-4-isopropyl-6-phenylhexyl-α-[(R)-α-(3,3-dimethyl-2-oxobutyl)hydrocinnamamido]imidazole-4-propionamide hydrochloride as an amorphous solid, MS: 699 (M+H)+;

from (S)-N-[(1S,2S,4S,E)-6-(butylcarbamoyl)-1-(cyclohexylmethyl)-2-hydroxy-4-isopropyl-5-hexenyl]-α-[(R)-α-(3,3-dimethyl-2-oxobutyl)hydrocinnamamido]imidazole-4-propionamide the (S)-N-[(1S,2S,4S)-6-(butylcarbamoyl)-1-(cyclohexylmethyl)-2-hydroxy-4-isopropylhexyl]-α-[(R)-α-(3,3-dimethyl-2-oxobutyl)hydrocinnamamido]imidazole-4-propionamide hydrochloride as an amorphous solid, MS: 722 (M+H)+, and from (S)-N-[(1S,2S,4S,E)-1-(cyclohexylmethyl)-2-hydroxy-4-isopropyl-6-[(2-pyridylmethyl)carbamoyl]-5-hexenyl]-α-[(R)-α-(3,3-dimethyl-2-oxobutyl)-hydrocinnamamido]imidazole-4-propionamide the (S)-N-[(1S,2S,4S)-1-(cyclohexylmethyl)-2-hydroxy-4-isopropyl-6-[(2-pyridyl)carbamoyl]hexyl]-α-[(R)-α-(3,3-dimethyl-2-oxobutyl)hydrocinnamamido]imidazole-4-propionamide dihydrochloride as an amorphous solid, MS: 757 (M+H)+.

EXAMPLE 15

The following compounds were manufactured in an analogous manner to that described in Example 6 by cleaving off the Boc protecting group on the imidazole ring with potassium carbonate in methanol:

From t-butyl [(S)-α-[[(S)-1-[[(1S,2S,4S)-6-[1-(benzyloxy)formamido]-1-(cyclohexylmethyl)-2-hydroxy-4-isopropylhexyl]carbamoyl]-2-(3-t-butoxycarbonyl)imidazol-4-ylethyl]carbamoyl]phenethyl]-carbamate the t-butyl [(S)-α-[[(S)-1-[[(1S,2S,4S)-6-[1-(benzyloxy)-formamido]-1-(cyclohexylmethyl)-2-hydroxy-4-isopropylhexyl]carbamoyl]-2-imidazol-4-ylethyl]carbamoyl]phenethyl]carbamate as an amorphous solid, MS: 789 (M+H)+, and from t-butyl [(S)-α-[[(S)-1-[[(1S,2S,4S)-6-(3-benzyl-2-oxo-1-imidazolinyl)hexyl]carbamoyl]-2-(3-t-butoxycarbonyl)imidazol-4-ylethyl]carbamoyl]-phenethyl]carbamate the t-butyl [(S)-α-[[(S)-1-[[(1S,2S,4S)-6-(3-benzyl-2-oxo-1-imidazolinyl)-hexyl]carbamoyl]-2-imidazol-4-ylethyl]carbamoyl]-phenethyl]carbamate as an amorphous solid, MS: 862 (M+H)+.

The carbamates used as the starting materials were prepared as follows:

t-Butyl [(S)-α-[[(S)-1-[[(1S,2S,4S)-6-[1-(benzyloxy)-formamido]-1-(cyclohexylmethyl)-2-hydroxy-4-isopropylhexyl]carbamoyl]-2-(3-t-butoxycarbonyl)imidazol-4-ylethyl]-carbamoyl]phenethyl]carbamate 5.0 g (12.15 mmol) of t-butyl 4-(cyclohexylmethyl)-5-(4-hydroxy-2-isopropylbutyl)-2,2-dimethyl-3-oxazolidinecarboxylate, 4.68 g (17.8 mmol) of triphenylphosphine and 2.48 g (17 mmol) of phthalimide are dissolved in 70 ml of tetrahydrofuran and cooled to 10°. Then, a solution of 2.8 ml (17.8 mmol) of diethyl azodicarboxylate in 15 ml of tetrahydrofuran is added dropwise within 10 minutes and the reaction mixture is stirred at room temperature for 4 hours. Then, the reaction mixture is evaporated under reduced pressure and the residue is chromatographed on 160 g of silica gel with a mixture of methylene chloride and hexane as the eluting agent, whereby there are obtained 5.4 g of t-butyl (4S,5S)-4-(cyclohexylmethyl)-5-[(S)-2-isopropyl-4-phthalimidobutyl]-2,2-dimethyl-3-oxazolidinecarboxylate as an oil, MS: 525 (M−CH₃)+.

5.4 g (9.99 mmol) of t-butyl (4S,5S)-4-(cyclohexylmethyl)-5-[(S)-2-isopropyl-4-phthalimidobutyl]-2,2-dimethyl-3-oxazolidinecarboxylate are dissolved in 200 ml of ethanol, treated with 2.0 ml (41 mmol) of hydrazine hydrate and heated to reflux for 2.5 hours. Subsequently, the reaction mixture is evaporated under reduced pressure and the residue is suspended in ether and filtered. Evaporation of the filtrate yields 3.82 g of t-butyl (4S,5S)-5-[(S)-4-amino-2-isopropyl]-4-(cyclohexylmethyl)-2,2-dimethyl-3-oxazolidinecarboxylate as an oil, MS: 395 (M−CH₃)+.

3.72 g (9.06 mmol) of t-butyl (4S,5S)-5-[(S)-4-amino-2-isopropyl]-4-(cyclohexylmethyl)-2,2-dimethyl-3-oxazolidinecarboxylate are dissolved in 20 ml of methylene chloride, treated with 1.5 ml (10.7 mmol) of triethylamine and cooled to 0°. Thereafter, there are added at this temperature in portions within 5 minutes 2.49 g (10.7 mmol) of N-(benzyloxycarbonyloxy)succinimide. The reaction mixture is subsequently stirred at room temperature for 2 hours, thereafter evaporated under reduced pressure, treated with 70 ml of ether and 70 ml of 1N sodium hydroxide solution and stirred at room temperature for 1 hour. Subsequently, the reaction mixture is extracted with ether and the ether extracts are dried over magnesium sulphate and evaporated. Chromatography of the residue obtained on 50 g of silica gel with a mixture of methylene chloride and isopropanol as the eluting agent yields 4.23 g of t-butyl (4S,5S)-5-

[(S)-4-[1-(benzyloxy)formamido]-2-isopropylbutyl]-4-(cyclohexylmethyl)-2,2-dimethyl-3-oxazolidinecarboxylate as an oil, MS: 529 (M−CH₃)⁺.

Cleavage of the Boc protecting group with simultaneous opening of the oxazolidine ring with hydrochloric acid in methanol and reaction with Boc-Phe-His-(Boc)-OH yields t-butyl [(S)-α-[[(S)-1-[[(1S,2S,4S)-6-[1-(benzyloxy)formamido]-1-(cyclohexylmethyl)-2-hydroxy-4-isopropylhexyl]carbamoyl]-2-(3-t-butoxycarbonyl)imidazol-4-ylethyl]carbamoyl]phenethyl]carbamate which is used in the next step without further purification.

t-Butyl [(S)-α-[[(S)-1-[[(1S,2S,4S)-6-(3-benzyl-2-oxo-1-imidazolidinyl)hexyl]carbamoyl]-2-(3-t-butoxycarbonyl)imidazol-4-ylethyl]carbamoyl]phenethyl]carbamate 1.0 g (2.4 mmol) of t-butyl 4-(cyclohexylmethyl)-5-(4-hydroxy-2-isopropylbutyl)-2,2-dimethyl-3-oxazolidinecarboxylate, 0.74 g (3.3 mmol) of 1-benzyl-2-benzimidazolidinone and 0.92 g (3.5 mmol) of triphenylphosphine are dissolved in 17 ml of tetrahydrofuran, cooled to 0° and treated with a solution of 0.81 g (3.5 mmol) of di-t-butyl azodicarboxylate in 3 ml of tetrahydrofuran. The reaction mixture is subsequently stirred for 2.5 hours without cooling and thereafter evaporated under reduced pressure. Chromatography of the residue on 36 g of silica gel with a mixture of methylene chloride and isopropanol as the eluting agent yields 1.76 g of a product which is dissolved in 30 ml of methanol and treated with 11 ml (41.8 mmol) of 3.8M hydrochloric acid in methanol while cooling with ice. The thus-obtained reaction mixture is stirred at room temperature for 4 hours and subsequently evaporated under reduced pressure, and the residue is poured into 2N sodium carbonate solution and extracted with methylene chloride. The methylene chloride extracts are dried over magnesium sulphate and evaporated, and the residue is chromatographed on 20 g of silica gel with a mixture of methylene chloride, isopropanol and concentrated aqueous ammonia as the eluting agent. In this manner there is obtained 0.83 g of 1-[(3S,5S,6S)-6-amino-7-cyclohexyl-5-hydroxy-3-isopropylheptyl]-3-benzyl-2-benzimidazolinone as an oil, MS: 478 (M+H)⁺.

Reaction of 1-[(3S,5S,6S)-6-amino-7-cyclohexyl-5-hydroxy-3-isopropylheptyl]-3-benzyl-2-benzimidazolinone with Boc-Phe-His(Boc)-OH yields t-butyl [(S)-α-[[(S)-1-[[(1S,2S,4S)-6-(3-benzyl-2-oxo-1-imidazolinyl)hexyl]carbamoyl]-2-(3-t-butoxycarbonyl)imidazol-4-ylethyl]carbamoyl]phenethyl]carbamate which is used directly in the next step without further purification.

EXAMPLE 16

1.0 g (1.27 mmol) of t-butyl [(S)-α-[[(S)-1-[[(1S,2S,4S)-6-[1-(benzyloxy)formamido[-1-(cyclohexylmethyl)-2-hydroxy-4-isopropylhexyl]carbamoyl]-2-imidazol-4-ylethyl]carbamoyl]phenethyl]carbamate and 0.146 g (1.27 mmol) of pyridine hydrochloride are dissolved in 15 ml of methanol and, after the addition of 0.10 g of palladium on charcoal (5%) hydrogenated for 2.5 hours at room temperature and atmospheric pressure. After completion of the hydrogen uptake the catalyst is filtered off and the filtrate is evaporated under reduced pressure, whereby there is obtained 0.87 g of t-butyl [(S)-α-[[(S)-1-[[(1S,2S,4S)-6-amino-1-(cyclohexylmethyl)-2-hydroxy-4-isopropylhexyl]carbamoyl]-2-imidazol-4-ylethyl]carbamoyl]phenethyl]carbamate hydrochloride as an amorphous solid, MS: 655 (M+H)⁺.

EXAMPLE 17

32 mg (0.2 mmol) of dihydrocinnamic acid, 45 mg (0.2 mmol) of EDC and 37 mg (0.2 mmol) of HOBT are dissolved in 5 ml of methylene chloride and the reaction mixture is treated with 0.09 ml (0.7 mmol) of N-ethylmorpholine and subsequently cooled to −10°. Subsequently, there are added dropwise at this temperature 135 mg (0.195 mmol) of t-butyl [(S)-α-[[(S)-1-[[(1S,2S,4S)-6-amino-1-(cyclohexylmethyl)-2-hydroxy-4-isopropylhexyl]carbamoyl]-2-imidazol-4-ylethyl]carbamoyl]phenethyl]carbamate hydrochloride in 2 ml of dimethylformamide and the reaction mixture is stirred at −10° for 1 hour and at room temperature for 24 hours. Then, the reaction mixture is poured into 2N sodium carbonate solution and extracted with methylene chloride. The methylene chloride extracts are dried over magnesium sulphate and evaporated under reduced pressure. Chromatography of the thus-obtained residue on 5 g of silica gel with a mixture of methylene chloride and isopropanol as the eluting agent yields 93 mg of t-butyl [(S)-α-[[(S)-1-[[(1S,2S,4S)-1-(cyclohexylmethyl)-6-hydrocinnamamido-2-hydroxy-4-isopropylhexyl]carbamoyl]-2-imidazol-4-ylethyl]carbamoyl]phenethyl]carbamate as an amorphous solid, MS: 787 (M+H)⁺.

EXAMPLE 18

The following compounds were manufactured in an analogous manner to that described in Example 17:

From t-butyl [(S)-α-[[(S)-1-[[(1S,2S,4S)-6-amino-1-(cyclohexylmethyl)-2-hydroxy-4-isopropylhexyl]carbamoyl]-2-imidazol-4-ylethyl]carbamoyl]phenethyl]carbamate hydrochloride and 3-(4-pyridyl)propionic acid the t-butyl [(S)-α-[[(S)-1-[[(1S,2S,4S)-1-(cyclohexylmethyl)-2-hydroxy-4-isopropyl-6-[3-(4-pyridyl)propionamido]hexyl]carbamoyl]-2-imidazol-4-ylethyl]carbamoyl]phenethyl]carbamate as an amorphous solid, MS: 788 (M+H)⁺;

from t-butyl [(S)-α-[[(S)-1-[[(1S,2S,4S)-6-amino-1-(cyclohexylmethyl)-2-hydroxy-4-isopropylhexyl]carbamoyl]-2-imidazol-4-ylethyl]carbamoyl]phenethyl]carbamate hydrochloride and 1-benzyl-4-piperidinecarboxylic acid the t-butyl [(S)-α-[[(S)-1-[[(1S,2S,4S)-6-(1-benzyl-4-piperidinecarboxamido)-1-(cyclohexylmethyl)-2-hydroxy-4-isopropylhexyl]carbamoyl]-2-imidazol-4-ylethyl]carbamoyl]phenethyl]carbamate as an amorphous solid, MS: 856 (M+H)⁺;

from t-butyl [(S)-α-[[(S)-1-[[(1S,2S,4S)-6-amino-1-(cyclohexylmethyl)-2-hydroxy-4-isopropylhexyl]carbamoyl]-2-imidazol-4-ylethyl]carbamoyl]phenethyl]carbamate hydrochloride and 2-[7-chloro-5-(2-fluorophenyl)-1,3-dihydro-2-oxo-2H-1,4-benzodiazepin-1-yl]acetic acid the t-butyl [(S)-α-[[(S)-1-[[(1S,2S,4S)-6--[2-[7-chloro-5-(2-fluorophenyl)-2,3-dihydro-2-oxo-1H-[1,4]benzodiazepin-1-yl]acetamido]-1-(cyclohexylmethyl)-2-hydroxy-4-isopropylhexyl]carbamoyl]-2-imidazol-4-ylethyl]carbamoyl]phenethyl]carbamate as an amorphous solid, MS: 983 (M+H)⁺;

from t-butyl [(S)-α-[[(S)-1-[[(1S,2S,4S)-6-amino-1-(cyclohexylmethyl)-2-hydroxy-4-isopropylhexyl]carbamoyl]-2-imidazol-4-ylethyl]carbamoyl]phenethyl]carbamate hydrochloride and 3-(4-imidazolyl)propionic acid the t-butyl [(S)-α-[[(S)-1-[[(1S,2S,4S)-1-(cyclohexylmethyl)-2-hydroxy-6-[imidazol-4-propionamido]-4-isopropylhexyl]carbamoyl]-2-imidazol-4-ylethyl]carbamoyl]phenethyl]carbamate as an amorphous solid, MS: 777 (M+H)+, and from t-butyl [(S)-α-[[(S)-1-[[(1S,2S,4S)-6-amino-1-(cyclohexylmethyl)-2-hydroxy-4-isopropylhexyl]carbamoyl]-2-imidazol-4-ylethyl]carbamoyl]phenethyl]carbamate hydrochloride and 2-benzimidazolylpentanoic acid the t-butyl [(S)-α-[[(S)-1-[[(1S,2S,4S)-6-(2-benzimidazolvaleramido)-1-(cyclohexylmethyl)-2-hydroxy-4-isopropylhexyl]carbamoyl]-2-imidazol-4-ylethyl]carbamoyl]phenethyl]carbamate as an amorphous solid, MS: 855 (M+H)+.

The acids used as the starting materials are known or can be prepared in analogy to the preparation of known compounds.

EXAMPLE 19

0.100 g (0.145 mmol) of t-butyl [(S)-α-[[(S)-1-[[(1S,2S,4S)-6-amino-1-(cyclohexylmethyl)-2-hydroxy-4-isopropylhexyl]carbamoyl]-2-imidazol-4-ylethyl]carbamoyl]phenethyl]carbamate hydrochloride in 1 ml of ethanol is treated with 0.05 ml (0.25 mmol) of Hünig base, cooled to 0° and treated with 0.018 ml (0.16 mmol) of butyl isocyanate in 1 ml of ethanol. Then, the reaction mixture is stirred at room temperature for 2 hours and subsequently evaporated under reduced pressure. Chromatography of the residue on 5 g of silica gel with a mixture of methylene chloride and isopropanol as the eluting agent yields 0.063 g of t-butyl [(S)-α-[[(S)-1-[[(1S,2S,4S)-6-(3-butylureido)-1-(cyclohexylmethyl)-2-hydroxy-4-isopropylhexyl]carbamoyl]-2-imidazol-4-ylethyl]carbamoyl]phenethyl]carbamate as an amorphous solid, MS: 754 (M+H)+.

EXAMPLE 20

0.136 g (0.197 mmol) of t-butyl [(S)-α-[[(S)-1-[[(1S,2S,4S)-6-amino-1-(cyclohexylmethyl)-2-hydroxy-4-isopropylhexyl]carbamoyl]-2-imidazol-4-ylethyl]carbamoyl]phenethyl]carbamate hydrochloride, 0.051 g (0.2 mmol) of benzyl [(methylthio)formimidoyl]carbamate and 0.07 ml (0.34 mmol) of Hünig base in 1 ml of absolute ethanol are stirred at 70° under argon for 3 hours. Thereafter, the reaction mixture is cooled, poured into 2N potassium carbonate solution and extracted with methylene chloride. The methylene chloride extracts are dried over magnesium sulphate and evaporated under reduced pressure. Chromatography of the residue obtained on 2 g of silica gel with a mixture of methylene chloride and isopropanol as the eluting agent yields 0.131 g of benzyl [N-[(3S,5S,6S)-6-[[N-[N-(t-butoxycarbonyl)-3-phenyl-L-alanyl]-L-histidyl]amino]-7-cyclohexyl-5-hydroxy-3-isopropylheptyl]amidino]carbamate as a colourless oil, MS: 831 (M+H)+.

EXAMPLE 21

0.110 g (0.132 mmol) of benzyl [N-[(3S,5S,6S)-6-[[N-[N-(t-butoxycarbonyl)-3-phenyl-L-alanyl]-L-histidyl]amino]-7-cyclohexyl-5-hydroxy-3-isopropylheptyl]amidino]carbamate and 0.015 mg (0.132 mmol) of pyridine hydrochloride are dissolved in 2.4 ml of methanol and hydrogenated in the presence of 20 mg of palladium on charcoal (5%) for 3 hours at room temperature and atmospheric pressure. After completion of the hydrogen uptake the catalyst is filtered off and the filtrate is evaporated under reduced pressure. In this manner there is obtained 0.074 g of t-butyl [(S)-α-[[(S)-1-[[(1S,2S,4S)-1-(cyclohexylmethyl)-6-guanidino-2-hydroxy-4-isopropylhexyl]carbamoyl]-2-imidazol-4-ylethyl]carbamoyl]phenethyl]carbamate hydrochloride as an amorphous solid, MS: 697 (M+H)−.

EXAMPLE 22

The following compounds were manufactured in an analogous manner to that described in Example 6 by cleaving off the Boc protecting group on the imidazole ring:

From (S)-N-[(1S,2S,4S,5S or R)-1-(cyclohexylmethyl)-2,5-dihydroxy-4-isopropyldecyl]-α-[(R)-α-(3,3-dimethyl-2-oxobutyl)hydrocinnamamido]-3-t-butoxycarbonylimidazole-4-propionamide the (S)-N-[(1S,2S,4S,5S or R)-1-(cyclohexylmethyl)-2,5-dihydroxy-4-isopropyldecyl]-α-[(R)-α-(3,3-dimethyl-2-oxobutyl)hydrocinnamamido]imidazole-4-propionamide as an amorphous solid, MS: 695 (M+H)+;

from (S)-N-[(1S,2S,4S,5R or S)-1-(cyclohexylmethyl)-2,5-dihydroxy-4-isopropyldecyl]-α-[(R)-α-(3,3-dimethyl-2-oxobutyl)hydrocinnamamido]-3-t-butoxycarbonylimidazole-4-propionamide the (S)-N-[(1S,2S,4S,5R or S)-1-(cyclohexylmethyl)-2,5-dihydroxy-4-isopropyldecyl]-α-[(R)-α-(3,3-dimethyl-2-oxobutyl)hydrocinnamamido]imidazole-4-propionamide as an amorphous solid, MS: 695 (M+H)+, and from (S)-N-[(1S,2S,4S)-1-(cyclohexylmethyl)-2-hydroxy-4-isopropyl-5-oxodecyl]-α-[(R)-α-(3,3-dimethyl-2-oxobutyl)hydrocinnamamido]-3-t-butoxycarbonylimidazole-4-propionamide the (S)-N-[(1S,2S,4S)-1-(cyclohexylmethyl)-2-hydroxy-4-isopropyl-5-oxodecyl]-α-[(R)-α-(3,3-dimethyl-2-oxobutyl)hydrocinnamamido]imidazole-4-propionamide as an amorphous solid, MS: 675 ((M−H$_2$O)+H)+.

The propionamides used as the starting materials were prepared as follows:

(S)-N-[(1S,2S,4S,5S or R)-1-(Cyclohexylmethyl)-2,5-dihydroxy-4-isopropyldecyl]-α-[(R)-α-(3,3-dimethyl-2-oxobutyl)hydrocinnamamido]-3-t-butoxycarbonylimidazole-4-propionamide 0.32 g (0.013 gram atom) of magnesium shavings are covered with 10 ml of absolute ether and thereafter treated dropwise with a solution of 1.66 ml (13 mmol) of pentyl bromide in 35 ml of absolute ether in such a manner that the reaction mixture boils slightly. After completion of the addition the mixture is heated to reflux for a further 1 hour and subsequently cooled to −50° and treated dropwise at this temperature with a solution of 3.5 g (8.8 mmol) of t-butyl (4S,5S)-4-(cyclohexylmethyl)-5-[(S)-2-formyl-3-methylbutyl]-2,2-dimethyl-3-oxazolidinecarboxylate in 45 ml of absolute ether. After stirring without cooling for 1 hour the reaction mixture is poured into ice-water and extracted with ether. The ether extracts are dried over magnesium sulphate and evaporated under reduced pressure. Chromatography of the residue on 50 g of silica gel with a mixture of methylene chloride and isopropanol as the eluting agent yields 1.73 g of t-butyl (4S,5S)-4-(cyclohexylmethyl)-5-[(2S,3S or R)-3-hydroxy-2-isopropyloctyl]-2,2-dimethyl-3-oxazolidinecarboxylate and 1.41 g of the epimeric t-butyl (4S,5S)-4-(cyclohexylmethyl)-5-[(2S,3R or S)-3-hydroxy-2-isopropyloctyl]-2,2-dimethyl-3-oxazolydinecarboxylate as well as 0.65 g of a mixture of the two epimers, both as oils, MS: (both): 452 (M−CH$_3$)+.

Cleavage of the Boc protecting group with the simultaneous opening of the oxazolidine ring with hydrochloric acid in methanol from t-butyl (4S,5S)-4-(cyclohexylmethyl)-5-[(2S,3S or R)-3-hydroxy-2-isopropyloctyl]-2,2-dimethyl-3-oxazolidinecarboxylate and reaction with 1-(t-butoxycarbonyl)-N-[(R)-α-(3,3-dimethyl-2-oxobutyl)hydrocinnamoyl]-L-histidine yields (S)-N-[(1S,2S,4S,5S or R)-1-(cyclohexylmethyl)-2,5-dihydroxy-4-isopropyldecyl]-α-[(R)-α-(3,3-dimethyl-2-oxobutyl)hydrocinnamamido]-3-t-butoxycarbonylimidazole-4-propionamide which is used directly in the next step without further purification.

(S)-N-[(1S,2S,4S,5R or S)-1-(cyclohexylmethyl)-2,5-dihydroxy-4-isopropyldecyl]-α-[(R)-α-(3,3-dimethyl-2-oxobutyl)hydrocinnamamido]-3-t-butoxycarbonylimidazole-4-propionamide By cleaving off the Boc protecting group with the simultaneous opening of the oxazolidine ring with hydrochloric acid in methanol and reacting with 1-(t-butoxycarbonyl)-N-[(R)-α-(3,3-dimethyl-2-oxobutyl)hydrocinnamoyl]-L-histidine there is obtained from t-butyl (4S,5S)-4-(cyclohexylmethyl)-5-[(2S,3R or S)-3-hydroxy-2-isopropyloctyl]-2,2-dimethyl-3-oxazolidinecarboxylate the (S)-N-[(1S,2S,4S,5R or S)-1-(cyclohexylmethyl)-2,5-dihydroxy-4-isopropyldecyl]-α-[(R)-α-(3,3-dimethyl-2-oxobutyl)hydrocinnamamido]-3-t-butoxycarbonylimidazole-4-propionamide which is used directly in the next step without further purification.

(S)-N-[(1S,2S,4S)-1-(Cyclohexylmethyl)-2-hydroxy-4-isopropyl-5-oxodecyl]-α-[(R)-α-(3,3-dimethyl-2-oxobutyl)hydrocinnamamido]-3-t-butoxycarbonylimidazole-4-propionamide 235 mg (0.5 mmol) of the mixture of epimers of t-butyl (4S,5S)-4-(cyclohexylmethyl)-5-[(2S,3S or R)-3-hydroxy-2-isopropyloctyl]-2,2-dimethyl-3-oxazolidinecarboxylate and t-butyl (4S,5S)-4-(cyclohexylmethyl)-5-[(2S,3R or S)-3-hydroxy-2-isopropyloctyl]-2,2-dimethyl-3-oxazolidinecarboxylate are dissolved in 5 ml of methylene chloride and treated with 400 mg of molecular sieve (3 Å), 0.05 ml (0.87 mmol) of acetic acid as well as 280 mg (0.7 mmol) of pyridinium dichromate and stirred at room temperature for 1 hour. Thereafter, the reaction mixture is filtered through Dicalit and the filtrate is evaporated under reduced pressure. Chromatography of the residue on 5 g of silica gel with methylene chloride as the eluting agent yields 197 mg of t-butyl (4S,5S)-4-(cyclohexylmethyl)-5-[(S)-2-isopropyl-3-oxooctyl]-2,2-dimethyl-3-oxazolidinecarboxylate as an oil, MS: 450 (M−CH$_3$)+.

Cleavage of the Boc protecting group with the simultaneous opening of the oxazolidine ring with hydrochloric acid in methanol and reaction with 1-(t-butoxycarbonyl)-N-[(R)-α-(3,3-dimethyl-2-oxobutyl)hydrocinnamoyl]-L-histidine yields (S)-N-[(1S,2S,4S)-1-(cyclohexylmethyl)-2-hydroxy-4-isopropyl-5-oxodecyl]-α-[(R)-α-(3,3-dimethyl-2-oxobutyl)hydrocinnamamido]-3-t-butoxycarbonylimidazole-4-propionamide which is used directly in the next step without further purification.

EXAMPLE 23

0.4 g (0.5 mmol) of (S)-N-[(1S,2S,4S)-4-benzoyl-1-(cyclohexylmethyl)-2-hydroxy-5-methylhexyl]-α-[(R)-α-(3,3-dimethyl-2-oxobutyl)hydrocinnamamido]-3-t-butoxycarbonylimidazole-4-propionamide is dissolved in 5 ml of methylene chloride and treated with 2 ml of 90% trifluoroacetic acid and stirred at room temperature for 4 hours. Thereafter, the reaction mixture is poured into 2N sodium bicarbonate solution and extracted with methylene chloride. The methylene chloride extracts are dried over potassium carbonate and evaporated under reduced pressure. Chromatography of the residue on 8 g of silica gel with a mixture of methylene chloride and isopropanol as the eluting agent yields 0.087 g of (S)-N-[(1S,2S,4S)-4-benzoyl-1-(cyclohexylmethyl)-2-hydroxy-5-methylhexyl]-α-[(R)-α-(3,3-dimethyl-2-oxobutyl)hyrocinnamamido]imidazole-4-propionamide as an amorphous solid, MS: 699 (M+H)+.

The (S)-N-[(1S,2S,4S)-4-benzoyl-1-(cyclohexylmethyl)-2-hydroxy-5-methylhexyl]-α-[(R)-α-(3,3-dimethyl-2-oxobutyl)hydrocinnamamido]-3-t-butoxycarbonylimidazole-4-propionamide used as the starting material was prepared as follows:

0.237 g (0.01 gram atom) of magnesium shavings are covered with 5 ml of absolute ether and treated dropwise with a solution of 1.03 ml (10 mmol) of bromobenzene in 30 ml of absolute ether in such a manner that the reaction mixture boils slightly. Subsequently, the mixture is heated to reflux for 1 hour and then cooled to −30° and treated dropwise with a solution of 2.60 g (6.5 mmol) of t-butyl (4S,5S)-4-(cyclohexylmethyl)-5-[(S)-2-formyl-3-methylbutyl]-2,2-dimethyl-3-oxazolidinecarboxylate in 35 ml of absolute ether at −15°. After stirring for 1 hour without cooling the reaction mixture is poured into ice-water and extracted with ether. The ether extracts are dried over magnesium sulphate and evaporated under reduced pressure. Chromatography of the residue on 40 g of silica gel with a mixture of methylene chloride and isopropanol as the eluting agent yields 3.1 g of t-butyl (4S,5S)-4-(cyclohexylmethyl)-5-[(S)-2-[(R or S)-α-hydroxybenzyl]-3-methylbutyl]-2,2-dimethyl-3-oxazolidinecarboxylate as an oil, MS: 458 (M−CH$_3$)+.

2.2 g (4.65 mmol) of t-butyl (4S,5S)-4-(cyclohexylmethyl)-5-[(S)-2-[(R or S)-α-hydroxybenzyl]-3-methylbutyl]-2,2-dimethyl-3-oxazolidinecarboxylate are dissolved in 100 ml of methylene chloride, treated with 22 g (253 mmol) of manganese dioxide and stirred at room temperature for 1 hour. A further 11 g (126 mmol) of manganese dioxide are added twice, in each case after 1 hour. The reaction mixture is subsequently stirred for a further 2.5 hours and then filtered. The filtrate is evaporated under reduced pressure and the residue is chromatographed on 20 g of silica gel with methylene chloride as the eluting agent, whereby there are obtained 1.69 g of t-butyl (4S,5S)-5-[(S)-2-benzoyl-3-methylbutyl]-4-(cyclohexylmethyl)-2,2-dimethyl-3-oxazolidinecarboxylate as an oil, MS: 471 (M+H)+.

400 mg (0.85 mmol) of t-butyl (4S,5S)-5-[(S)-2-benzoyl-3-methylbutyl]-4-(cyclohexylmethyl)-2,2-dimethyl-3-oxazolidinecarboxylate are dissolved in 15 ml of methanol and treated with 4.7 ml (18 mmol) of 3.9M hydrochloric acid in methanol. The reaction mixture is thereafter stirred at room temperature for 20 hours and subsequently evaporated under reduced pressure. The residue is dissolved in 5 ml of methanol and the solution is treated with 0.2 ml (1.8 mmol) of trimethyl orthoformate and a few crystals of p-toluenesulphonic acid and stirred at room temperature for 2 hours and at 50° for 2 hours. Thereafter, the reaction mixture is poured into 2N sodium bicarbonate solution and extracted with methylene chloride. The methylene chloride extracts are dried over magnesium sulphate and evaporated under reduced pressure, whereby there is obtained 0.27 g of (αS,2S,4S)-α-(cyclohexylmethyl)tetrahydro-4-isopropyl-5-methoxy-5-phenyl-2-furanmethanamine as an oil, MS: 313 (M−CH₃OH)⁺.

250 mg (0.72 mmol) of (αS,2S,4S)-α-(cyclohexylmethyl)tetrahydro-4-isopropyl-5-methoxy-5-phenyl-2-furanmethanamine and 390 mg (0.80 mmol) of 1-(t-butoxycarbonyl)-N-[(R)-α-(3,3-dimethyl-2-oxobutyl)-hydrocinnamoyl]-L-histidine are dissolved in 5 ml of methylene chloride and treated dropwise at −20° with firstly 0.15 ml (0.8 mmol) of Hünig base and subsequently 0.13 ml (0.8 mmol) of diethyl cyanophosphonate. Thereafter, the reaction mixture is stirred at room temperature for 45 hours and subsequently poured into water and extracted with methylene chloride. The methylene chloride extracts are dried over potassium carbonate and evaporated under reduced pressure. Chromatography of the residue obtained on 10 g of silica gel with a mixture of methylene chloride and isopropanol as the eluting agent yields 400 mg of (S)-N-[(1S,2S,4S)-4-benzoyl-1-(cyclohexylmethyl)-2-hydroxy-5-methylhexyl]-α-[(R)-α-(3,3-dimethyl-2-oxobutyl)hydrocinnamamido]-3-t-butoxycarbonylimidazole-4-propionamide which is used directly in the next step without further purification.

EXAMPLE 24

The following compounds were manufactured in an analogous manner to that described in Example 6 by cleaving off the Boc protecting group on the imidazole ring:

From t-butyl [(S)-[[(S)-1-[[(1S,2S,4S,E)-1-(cyclohexylmethyl)-2-hydroxy-4-isopropyl-7-(phenethylcarbamoyl)-6-heptenyl]carbamoyl]-2-(3-t-butoxycarbonyl)imidazol-4-ylethyl]carbamoyl]phenethyl]carbamate the t-butyl [(S)-[[(S)-1-[[(1S,2S,4S,E)-1-(cyclohexylmethyl)-2-hydroxy-4-isopropyl-7-(phenethylcarbamoyl)-6-heptenyl]carbamoyl]-2-imidazol-4-ylethyl]carbamoyl]phenethyl]carbamate as an amorphous solid, MS: 799 (M+H)⁺, and from t-butyl [(S)-α-[[(S)-1-[[(1S,2S,4S,E)-1-(cyclohexylmethyl)-2-hydroxy-4-isopropyl-7-(2-pyridylcarbamoyl)-6-heptenyl]carbamoyl]-2-(3-t-butoxycarbonyl)imidazol-4-ylethyl]carbamoyl]phenethyl]carbamate the t-butyl [(S)-α-[[(S)-1-[[(1S,2S,4S,E)-1-(cyclohexylmethyl)-2-hydroxy-4-isopropyl-7-(2-pyridylcarbamoyl)-6-heptenyl]carbamoyl]-2-imidazol-4-ylethyl]-carbamoyl]phenethyl]carbamate as an amorphous solid, MS: 786 (M+H)⁺.

The carbamates used as the starting materials were prepared as follows:

t-Butyl [(S)-[[(S)-1-[[(1S,2S,4S,E)-1-(cyclohexylmethyl)-2-hydroxy-4-isopropyl-7-(phenethylcarbamoyl)-6-heptenyl]carbamoyl]-2-(3-t-butoxycarbonyl)imidazol-4-ylethyl]carbamoyl]phenethyl]carbamate 2.0 g (4.86 mmol) of t-butyl 4-(cyclohexylmethyl)-5-(4-hydroxy-2-isopropylbutyl)-2,2-dimethyl-3-oxazolidinecarboxylate in 10 ml of methylene chloride are added dropwise at room temperature within 10 minutes to a suspension of 2.74 g (7.3 mmol) of pyridinium dichromate in 70 ml of methylene chloride and the mixture is subsequently stirred intensively at room temperature for 24 hours. Thereafter, the reaction mixture is evaporated under reduced pressure and the residue is chromatographed twice on 20 g of silica gel with a mixture of methylene chloride and isopropanol as the eluting agent, whereby there are obtained 1.7 g of t-butyl (4S,5S)-4-(cyclohexymethyl)-5-[(R)-2-formylmethyl-3-methylbutyl]-2,2-dimethyl-3-oxazoldinecarboxylate as a yellowish oil, MS: 394 (M−CH₃)⁺.

0.39 g of a sodium hydride suspension (50% in mineral oil) is washed with hexane and covered with 30 ml of tetrahydrofuran. After cooling to 0° a solution of 2.4 ml (12 mmol) of triethyl phosphonoacetate in 5 ml of tetrahydrofuran is added dropwise at 0° within 5 minutes. Thereafter, the reaction mixture is stirred at room temperature for 30 minutes. After again cooling to 0° 1.65 g (4.02 mmol) of t-butyl (4S,5S)-4-(cyclohexymethyl)-5-[(R)-2-formylmethyl-3-methylbutyl]-2,2-dimethyl-3-oxazoldinecarboxylate in 10 ml of tetrahydrofuran is added dropwise within five minutes. After completion of the addition the reaction mixture is stirred at room temperature for 2 hours, subsequently poured into ice-water and extracted with ethyl acetate. The ethyl acetate extracts are dried over magnesium sulphate and evaporated. Chromatography of the residue on 30 g of silica gel with a mixture of methylene chloride and isopropanol as the eluting agent yields 1.78 g of t-butyl (4S,5S)-4-(cyclohexylmethyl)-5-[(S,E)-5-(ethoxycarbonyl)-2-isopropyl-4-pentenyl]-2,2-dimethyl-3-oxazolidinecarboxylate as an oil, MS: 464 (M−CH₃)⁺.

1.7 g (3.5 mmol) of t-butyl (4S,5S)-4-(cyclohexylmethyl)-5-[(S,E)-5-(ethoxycarbonyl)-2-isopropyl-4-pentenyl]-2,2-dimethy--3-oxazolidinecarboxylate are dissolved in 20 ml of dioxan and treated with 7 ml (7.0 mmol) of 1N sodium hydroxide solution. Thereafter, the reaction mixture is stirred at 90° for 2.5 hours, cooled and poured into ice-water. Then, the reaction mixture is adjusted to pH 3 with a pH 2 buffer of potassium hydrogen sulphate and potassium sulphate and extracted with methylene chloride. The methylene chloride extracts are dried over magnesium sulphate and evaporated under reduced pressure. Chromatography of the residue on 18 g of silica gel with a mixture of methylene chloride and isopropanol as the eluting agent yields 1.28 g of (E,S)-5-[[(4S,5S)-3-(t-butoxycarbonyl)-4-(cyclohexylmethyl)-2,2-dimethyl-5-oxazolidinyl]methyl]-6-methyl-2-heptenoic acid as an oil, MS: 436 (M−CH₃)⁺.

A mixture of 0.63 g (1.39 mmol) of (E,S)-5-[[(4S,5S)-3-(t-butoxycarbonyl)-4-(cyclohexylmethyl)-2,2-dimethyl-5-oxazolidinyl]methyl]-6-methyl-2-heptenoic acid, 0.32 g (1.7 mmol) of EDC, 0.28 g (2 mmol) of HOBT and 20 ml of methylene chloride is cooled to −10°, treated with 0.35 ml (2.7 mmol) of N-ethylmorpholine and 0.26 ml (2 mmol) of 2-phenethylamine in 10 ml of methylene chloride and stirred at −10° for 1.5 hours and at room temperature for 20 hours. Thereafter, the reaction mixture is poured into ice-water, adjusted to pH 3 with a pH 2 buffer of potassium hydrogen sulphate and potassium sulphate and extracted with methylene chloride. The methylene chloride extracts are washed with 2N sodium carbonate solution, dried over magnesium sulphate and evaporated under reduced pressure. Chromatography of the residue on 7.5 g of silica gel yields 0.66 g of t-butyl (4S,5S)-4-(cyclohexylmethyl)-5-[(S)-2-isopropyl-5-(phenethylcarbamoyl)-4-pentenyl]-2,2-dimethyl-3-oxazolidinecarboxylate as a colourless resin, MS: 539 (M−CH₃)⁺.

Cleavage of the Boc protecting group with simultaneous opening of the oxazolidine ring with hydrochloric acid in methanol and reaction with Boc-Phe-His-(Boc)-OH yields t-butyl [(S)-[[(S)-1-[[(1S,2S,4S,E)-1-(cyclohexylmethyl)-2-hydroxy-4-isopropyl-7-(phenethylcarbamoyl)-6-heptenyl]carbamoyl]-2-(3-t-butoxycarbonyl)imidazol-4-ylethyl]carbamoyl]phenethyl]-carbamate which is used directly in the next step without further purification.

t-Butyl [(S)-α-[[(S)-1-[[(1S,2S,4S,E)-1-(cyclohexylmethyl)-2-hydroxy-4-isopropyl-7-(2-pyridylcarbamoyl)-6-heptenyl]carbamoyl]-2-(3-t-butoxycarbonyl)imidazol-4-ylethyl]carbamoyl]phenethyl]carbamate This compound is obtained in an analogous manner to that described above by reacting (E,S)-5-[[(4S,5S)-3-(t-butoxycarbonyl)-4-(cyclohexylmethyl)-2,2-dimethyl-5-oxazolidinyl]methyl]-6-methyl-2-heptenoic acid with 2-pyridylmethylamine, cleaving off the Boc protecting group with simultaneous opening of the oxazolidine ring with hydrochloric acid in methanol from the resulting t-butyl (4S,5S)-4-(cyclohexylmethyl)-5-[(E,S)-2-isopropyl-5-[(2-pyridylmethyl)carbamoyl]-4-pentenyl]-2,2-dimethyl-3-oxazolidinecarboxylate [yellowish resin, MS: 541 (M+H)+] and reacting with Boc-Phe-His(-Boc)-OH, which is used directly in the next step without further purification.

EXAMPLE 25

80 mg (0.10 mmol) of t-butyl [(S)-[[(S)-1-[[(1S,2S,4S,E)-1-(cyclohexylmethyl)-2-hydroxy-4-isopropyl-7-(phenethylcarbamoyl)-6-heptenyl]carbamoyl]-2-imidazol-4-ylethyl]carbamoyl]phenethyl]-carbamate are dissolved in 1 ml of methanol and, after the addition of 0.015 g of palladium on charcoal (5%), hydrogenated for 7 hours at room temperature and atmospheric pressure. After completion of the hydrogen uptake the catalyst is filtered off and the filtrate is evaporated under reduced pressure, whereby there are obtained 64 mg of t-butyl [(S)-α-[[(S)-1-[[(1S,2S,4S)-1-(cyclohexylmethyl)-2-hydroxy-4-isopropyl-7-(phenethylcarbamoyl)heptyl]carbamoyl]-2-imidazol-4-ylethyl]carbamoyl]phenethyl]carbamate as an amorphous solid, MS: 801 (M+H)+.

In an analogous manner to that described above, by hydrogenating t-butyl [(S)-α-[[(S)-1-[[(1S,2S,4S,E)-1-(cyclohexylmethyl)-2-hydroxy-4-isopropyl-7-(2-pyridylcarbamoyl)-6-heptenyl]carbamoyl]-2-imidazol-4-ylethyl]carbamoyl]phenethyl]carbamate there was obtained t-butyl [(S)-α-[[(S)-1-[[(1S,2S,4S)-1-(cyclohexylmethyl)-2-hydroxy-4-isopropyl-7-[(2-pyridylmethyl)carbamoyl]heptyl]carbamoyl]-2-imidazol-4-ylethyl]carbamoyl]phenethyl]carbamate as a beige amorphous powder, MS: 788 (M+H)+.

EXAMPLE 26

In an analogous manner to that described in Example 6, by cleaving off the Boc protecting group on the imidazole ring with potassium carbonate in methanol from (S)-N-[(1S,2S,4R)-4-[(butylcarbamoyl)methyl)]-1-(cyclohexylmethyl)-2-hydroxy-5-methylhexyl]-α-[(R)-α-(3,3-dimethyl-2-oxobutyl)hydrocinnamamido]-3-t-butoxycarbonylimidazole-4-propionamide there was obtained (S)-N-[(1S,2S,4R)-4-[(butylcarbamoyl)methyl]-1-(cyclohexylmethyl)-2-hydroxy-5-methylhexyl]-α-[(R)-α-(3,3-dimethyl-2-oxobutyl)hydrocinnamamido]imidazole-4-propionamide as an amorphous solid, MS: 708 (M+H)+.

The (S)-N-[(1S,2S,4R)-4-[(butylcarbamoyl)methyl]-1-(cyclohexylmethyl)-2-hydroxy-5-methylhexyl]-α-[(R)-α-(3,3-dimethyl-2-oxobutyl)hydrocinnamamido]-3-t-butoxycarbonylimidazole-4-propionamide used as the starting material was prepared as follows:

1.5 g (3.64 mmol) of t-butyl 4-(cyclohexylmethyl)-5-(4-hydroxy-2-isopropylbutyl)-2,2-dimethyl-3-oxazolidinecarboxylate are dissolved in 22 ml of benzene and treated with 2.85 g (18 mmol) of finely powdered potassium permanganate and 12 ml of water. The reaction mixture is then cooled to 10° and treated while stirring with a solution of 0.51 g of tricaprylmethylammonium chloride in 2 ml of benzene and subsequently with 2.4 ml (42 mmol) of glacial acetic acid. Thereafter, the reaction mixture is stirred intensively at room temperature for 18 hours. For the working-up, the reaction mixture is then poured into ice-water, decolorized with sodium pyrosulphite and subsequently extracted with ether. The ether extracts are dried over magnesium sulphate and evaporated under reduced pressure. Chromatography of the residue on 25 g of silica gel with a mixture of methylene chloride and isopropanol as the eluting agent yields 1.3 g of (αR,4S,5S)-3-(t-butoxycarbonyl)-4-(cyclohexylmethyl)-β-isopropyl-2,2-dimethyl-5-oxazolidinebutyric acid as an oil, MS: 410 (M−CH₃)+.

A mixture of 1.25 g (2.94 mmol) of (αR,4S,5S)-3-(t-butoxycarbonyl)-4-(cyclohexylmethyl)-β-isopropyl-2,2-dimethyl-5-oxazolidinebutyric acid, 0.473 g (3.5 mmol) of HOBT, 0.671 g (3.5 mmol) of EDC, 0.72 ml (5.7 mmol) of N-ethylmorpholine and 60 ml of methylene chloride is cooled to −10° and treated with 0.32 g (4.4 mmol) of butylamine in 10 ml of methylene chloride. Thereafter, the reaction mixture is stirred for 18 hours without cooling, then poured into ice-water and extracted with methylene chloride. The methylene chloride extracts are washed with a pH 2 buffer of potassium hydrogen sulphate and potassium sulphate and with 2N sodium carbonate solution, dried over magnesium sulphate and evaporated under reduced pressure. In this manner there are obtained 1.38 g of t-butyl (4S,5S)-5-[(R)-2-[(butylcarbamoyl)methyl]-3-methylbutyl]-4-(cyclohexylmethyl)-2,2-dimethyl-3-oxazolidinecarboxylate as an oil, MS: 465 (M−CH₃)+.

By cleavage of the Boc protecting group with simultaneous opening of the oxazolidine ring and reaction with 1-(t-butoxycarbonyl)-N-[(R)-α-(3,3-dimethyl-2-oxobutyl)hydrocinnamoyl]-L-histidine there is obtained (S)-N-[(1S,2S,4R)-4-[(butylcarbamoyl)methyl]-1-(cyclohexylmethyl)-2-hydroxy-5-methylhexyl]-α-[(R)-α-(3,3-dimethyl-2-oxobutyl)hydrocinnamamido]-3-t-butoxycarbonylimidazole-4-propionamide which is used directly in the next step without further purification.

EXAMPLE 27

In an analogous manner to that described in Example 9, by reacting (3R,5S,6S)-6-amino-7-cyclohexyl-5-hydroxy-3-isopropylheptanoic acid butylamide with Boc-Phe-His-OH there is obtained t-butyl [(S)-α-[[(S)-1-[[(1S,2S,4R)-4-[(butylcarbamoyl)methyl]-1-(cyclohexylmethyl)-2-hydroxy-5-methylhexyl]carbamoyl]-2-imidazol-4-ylethyl]carbamoyl]phenethyl]carbamate as an amorphous solid, MS: 725 (M+H)+.

The (3R,5S,6S)-6-amino-7-cyclohexyl-5-hydroxy-3-isopropylheptanoic acid butylamide used as the starting material was prepared as follows:

This compound was obtained by cleaving off the Boc protecting group with simultaneous opening of the oxazolidine ring with hydrochloric acid in methanol from t-butyl (4S,5S)-5-[(R)-2-[(butylcarbamoyl)methyl]-3- methylbutyl]-4-(cyclohexylmethyl)-2,2-dimethyl-3-oxazolidinecarboxylate and was used directly in the next step without further purification.

EXAMPLE A

A sterile filtered aqueous solution of (S)-N-[(1S,2S,4R)-4-(butylcarbamoyl)methyl]-1-(cyclohexylmethyl)-2-hydroxy-5-methylhexyl]-α-[(R)-α-(3,3-dimethyl-2-oxobutyl)hydrocinnamamido]imidazole-4-propionamide is mixed while warming with a sterile gelatine solution, which contains phenol as a preserving agent, under aseptic conditions so that 1.0 ml of solution has the following composition:

| | |
|---|---|
| (S)-N-[(1S,2S,4R)-4-(Butylcarbamoyl)methyl]-1-(cyclohexylmethyl)-2-hydroxy-5-methylhexyl]-α-[(R)-α-(3,3-dimethyl-2-oxobutyl)-hydrocinnamamido]imidazole-4-propionamide | 3.0 mg |
| Gelatine | 150.0 mg |
| Phenol | 4.7 mg |
| Dist. water ad | 1.0 ml |

The mixture is filled into 1.0 ml vials under aseptic conditions.

EXAMPLE B 5 mg of (S)-N-[(1S,2S,4R)-4-(butylcarbamoyl)methyl]-1-(cyclohexylmethyl)-2-hydroxy-5-methylhexyl]-α-[(R)-α-(3,3-dimethyl-2-oxobutyl)hydrocinnamamido]imidazole-4-propionamide are dissolved in 1 ml of an aqueous solution with 20 mg of mannitol. The solution is filtered sterile and filled under aseptic conditions into a 2 ml ampoule, cooled to a low temperature and lyophilized. Prior to administration the lyophilizate is dissolved in 1 ml of distilled water or 1 ml of physiological saline. The solution is used intramuscularly or intravenously. This formulation can also be filled into double chamber injection ampoules.

EXAMPLE C 500 mg of finely milled (5.0 μm) (S)-N-[(1S,2S,4R)-4-(butylcarbamoyl)methyl]-1-(cyclohexylmethyl)-2-hydroxy-5-methylhexyl]-α-[(R)-α-(3,3-dimethyl-2-oxobutyl)-hydrocinnamamido]imidazole-4-propionamide are suspended in a mixture of 3.5 ml of Myglyol 812 and 0.08 g of benzyl alcohol. This suspension is filled into a container having a dosage valve. 5.0 g of Freon 12 are filled into the container through the valve under pressure. The Freon is dissolved in the Myglyol-benzyl alcohol mixture. This spray container contains about 100 individual dosages which can be applied individually.

EXAMPLE D

When the procedures described in Examples A–C are followed, corresponding galenical preparations can be manufactured from the following, likewise preferred, compounds:

t-Butyl [(S)-α-[[(S)-1-[[(1S,2S,4R)-4-[(butylcarbamoyl)methyl]-1-(cyclohexylmethyl)-2-hydroxy-5-methylhexyl]carbamoyl]-2-imidazol-4-ylethyl]carbamoyl]phenethyl]carbamate;

(S)-N-[1S,2S,4S)-1-(cyclohexylmethyl)-2-hydroxy-4-isopropyl-5-oxodecyl]-α-[(R)-α-(3,3-dimethyl-2-oxobutyl]hydrocinnamamido]imidazole-4-propionamide;

(S)-N-[(1S,2S,4S,E)-1-(cyclohexylmethyl)-2-hydroxy-4-isopropyl-6-[(2-pyridylmethyl)carbamoyl]-5-hexenyl]-α-[(R)-α-(3,3-dimethyl-2-oxobutyl)hydrocinnamamido]-imidazole-4-propionamide;

t-butyl [(S)-α-[[(S)-1-[[(1S,2S,4S)-1-(cyclohexylmethyl)-2-hydroxy-4-isopropyl-6-(propionyloxy)hexyl]carbamoyl]-2-imidazol-4-ylethyl]carbamoyl]phenethyl]carbamate;

t-butyl (R)-2-[[(S)-α-[[(R and S)-1-[[(1S,2S,4S)-1-(cyclohexylmethyl)-2-hydroxy-4-isopropyl-6-(pivaloyloxy)hexyl]carbamoyl]-2-imidazol-4-ylethyl]carbamoyl]phenethyl]carbamoyl]-1-pyrrolidinecarboxylate;

(2S or R,3S,5S,6S)-6-(Boc-D-Pro-Phe-His-NH)-7-cyclohexyl-3-isopropyl-1-(phenethylamino)-2,5-heptanediol;

(2R or S,3S,5S,6S)-6-(Boc-D-Pro-Phe-His-NH)-7-cyclohexyl-3-isopropyl-1-(phenethylamino)-2,5-heptanediol and (2RS,3S,5S,6S)-6-(Boc-D-Pro-Phe-His-NH)-7-cyclohexyl-3-isopropyl-1-[(2-pyridylmethyl)amino]-2,5-heptanediol.

We claim:

1. An amino acid derivative of the general formula

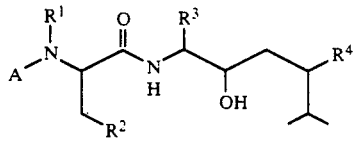

wherein $R^1$ is hydrogen or methyl, $R^2$ is ethyl, propyl, isopropyl, imidazol-2-yl, imidazol-4-yl, pyrazol-3-yl, thiazol-4-yl, thien-2-yl, ethoxycarbonyl, t-butylcarbonylmethyl, benzyloxycarbonylmethyl or t-butoxy, $R^3$ is isobutyl, cyclohexylmethyl or benzyl, A is

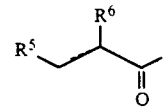

or —Y—Z and $R^4$ is alkanoyl, arylcarbonyl, 2,2-dialkylvinyl, —CH=CH—$R^7$,

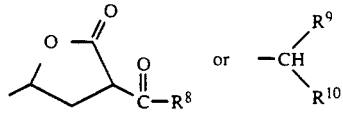

in which the dotted line is an additional bond which may or may not be present, $R^5$ is phenyl, substituted phenyl, benzyl or naphthyl and $R^6$ is hydrogen, alkoxycarbonylalkyl, alkylcarbonylalkyl, cycloalkylcarbonylalkyl, heterocycloalkylcarbonylalkyl, arylcarbonylalkyl, aminocarbonylalkyl, substituted aminocarbonylalkyl, aminoalkylcarbonylalkyl, substituted aminoalkylcarbonylalkyl, aminoalkylsulphonylalkyl, substituted aminoalkylsulphonylalkyl, alkoxycarbonylhydroxyalkyl, alkylcarbonylhydroxyalkyl, cycloalkylcarbonylhydroxyalkyl, heterocycloalkylcarbonylhydroxyalkyl, arylcarbonylhydroxyalkyl, aminocarbonylhydroxyalkyl, substituted aminocarbonylhydroxyalkyl, dialkoxyphosphoroxyalkyl, diphenyloxyphosphoroxyalkyl, arylalkyl, alkoxycarbonylamino, arylalkoxycarbonylamino, alkylthioalkyl, alkylsulphinylalkyl, alkylsulphonylalkyl, arylthioalkyl, arylsulphinylalkyl, arylsulphonylalkyl, arylalkylthioalkyl, arylalkylsulphinylalkyl or arylalkylsulphonylalkyl, with the proviso that $R^6$ can not be alkoxycarbonylamino or arylalkoxycarbonylamino when $R^5$ is phenyl, benzyl or α-naphthyl, Y is the bivalent residue of optionally N- and/or α-methylated phenylglycine, cyclohexylglycine, phenylalanine, cyclohexylalanine, 4-fluorophenylalanine, 4-chlorophenylalanine, tyrosine, O-methyltyrosine, α-naphthylalanine or homophenylalanine linked with Z at the N-terminal, Z is acyl, $R^7$ is aryl, heteroaryl, alkylaminocarbonyl, arylalkylaminocarbonyl or heteroarylalkylaminocarbonyl, $R^8$ is alkoxy, $R^9$ is hydrogen or hydroxy and $R^{10}$ is azidomethyl, —CH=CH—$R^7$, —$CH_2$—$OR^{11}$,

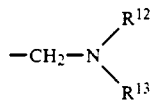

or —$(CH_2)_n$—$R^7$ in which $R^{11}$ is hydrogen, alkyl, arylalkyl, aryl, alkanoyl, arylalkylcarbonyl, heteroarylalkylcarbonyl or alkylcarbamoyl, $R^{12}$ and $R^{13}$ each independently is hydrogen, alkyl, arylalkyl, heteroarylalkyl, aryl, alkanoyl, alkoxycarbonyl, arylalkylcarbonyl, arylalkoxycarbonyl, heteroarylalkylcarbonyl, heterocycloalkylcarbonyl, alkylcarbamoyl or

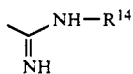

or $R^{12}$ and $R^{13}$ together with the nitrogen atom to which they are attached are a 5- or 6-membered heterocycle or optionally substituted benzimidazolonyl, n is 0, 1 or 2 and $R^{14}$ is hydrogen or arylalkoxycarbonyl, in the form of optically pure diastereomers, mixtures of diastereomers, diastereomeric racemates or mixtures of diastereomeric racemates as well as a pharmaceutically usable salt of such a compound.

2. An amino acid derivative as recited in claim 1, wherein $R^1$ is hydrogen.

3. An amino acid derivative as recited in claim 1, wherein $R^2$ is imidazol-2-yl, imidazol-4-yl or thiazol-4-yl.

4. An amino acid derivative as recited in claim 1, wherein $R^3$ is cyclohexylmethyl.

5. An amino acid derivative as recited in claim 1, wherein $R^4$ is alkanoyl, —CH=CH—$R^7$ or

6. An amino acid derivative as recited in claim 5, wherein $R^7$ is heteroarylalkylaminocarbonyl.

7. An amino acid derivative as recited in claim 5, wherein $R^{10}$ is —$CH_2$—$OR^{11}$,

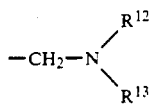

or —$(CH_2)_n$—$R^7$.

8. An amino acid derivative as recited in claim 7, wherein $R^{11}$ is alkanoyl.

9. An amino acid derivative as recited in claim 7, wherein $R^{12}$ is hydrogen.

10. An amino acid derivative as recited in claim 7, wherein $R^{13}$ is alkyl, arylalkyl, heteroarylalkyl or heteroarylalkylcarbonyl.

11. An amino acid derivative as recited in claim 1, wherein A is Y—Z.

12. An amino acid derivative as recited in claim 11, wherein Y is the bivalent residue of phenylalanine linked with Z at the N-terminal.

13. An amino acid derivative as recited in claim 11, wherein Z is the group $R^a$—O—CO— or the residue of an α-amino acid, said residue being acylated by this group, wherein $R^a$ is an optionally substituted, saturated aliphatic hydrocarbon residue with up to 10 carbon atoms or an optionally substituted heteroaromatic hydrocarbon residue with up to 18 carbon atoms.

14. An amino acid derivative as recited in claim 1, wherein A is

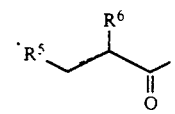

and $R^5$ is phenyl or substituted phenyl.

15. An amino acid derivative as recited in claim 1, wherein $R^6$ is alkylcarbonylalkyl, aminoalkylcarbonylalkyl, substituted aminoalkylcarbonylalkyl, aminoalkylsulphonylalkyl, substituted aminoalkylsulphonylalkyl or alkylsulphonylalkyl.

16. An amino acid derivative as recited in claim 1, wherein $R^1$ is hydrogen, $R^2$ is imidazol-4-yl, $R^3$ is cyclohexylmethyl, $R^4$ is alkanoyl or

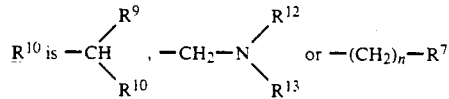

in which n is 0 and $R^7$ is alkylaminocarbonyl, $R^{12}$ is hydrogen, $R^{13}$ is arylalkyl or heteroarylalkyl, Y is a bivalent residue of phenylalanine linked with Z at the N-terminal and Z is the group $R^a$—O—CO— or the residue of proline which is acylated by this group, wherein $R^a$ is a saturated, aliphatic hydrocarbon residue with up to 6 carbon atoms.

17. An amino acid derivative selected from the group consisting of (S)-N-[[(1S,2S,4R)-4-[(butylcarbamoyl)-methyl]-1-(cyclohexylmethyl)-2-hydroxy-5-methylhexyl]-α-[(R)-α-(3,3-dimethyl-2-oxobutyl)hydrocinnamamido]imidazole-4-propionamide, t-butyl [(S)-α-[[(S)-1-[[(1S, 2S,4R)-4-[(butylcarbamoyl)methyl]]-1-(cyclohexylmethyl)-2-hydroxy-5-methylhexyl]carbamoyl]-2-imidazol-4-ylethyl]carbamoyl]phenethyl]carbamate, (S)-N-[(1S,2S,4S)-1-(cyclohexylmethyl)-2-hydroxy-4-isopropyl-5-oxodecyl]-α-[(R)-α-(3,3-dimethyl-2-oxobutyl]hydrocinnamamido]imidazole-4-propionamide, (S)-N-[(1S,2S,4S,E)-1-(cyclohexylmethyl)-2-hydroxy-4-isopropyl-6-[(2-pyridylmethyl)carbamoyl]-5-hexenyl]-α-[(R)-α-(3,3-dimethyl-2-oxobutyl)hydrocinnamamido]imidazole-4-propionamide, t-butyl [(S)-α-[[(S)-1-[[(1S,2S,4S)-1-(cyclohexylmethyl)-2-hydroxy-4-isopropyl-6-(propionyloxy)hexyl]carbamoyl]-2-imidazol-4-ylethyl]carbamoyl]phenethyl]carbamate, t-butyl (R)-2-[[(S)-α-[[(R and S)-1-[[(1S,2S,4S)-1-(cyclohexylmethyl)-2-hydroxy-4-isopropyl-6-(pivaloyloxy)hexyl]carbamoyl]-2-imidazol-4-ylethyl]carbamoyl]phenethyl]carbamoyl]-1-pyrrolidinecarboxylate, (2S or R,3S,5S,6S)-6-(Boc-D-Pro-Phe-His-NH)-7-cyclohexyl-3-isopropyl-1-(phenethylamino)-2,5-heptanediol, (2R or S,3S,5S,6S)-6(Boc-D-Pro-Phe-His-NH)-7-cyclohexyl-3-isopropyl-1-(phenethylamino)-2,5-heptanediol, and (2RS,3S,5S,6S)-6-(Boc-D-Pro-Phe-His-NH)-7-cyclohexyl-3-isopropyl-1-[(2-pyridylmethyl)amino]-2,5-heptanediol.

18. A compound selected from the group consisting of:

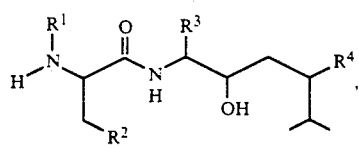  II

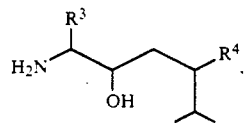  III

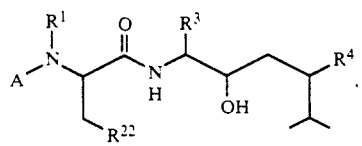  V'

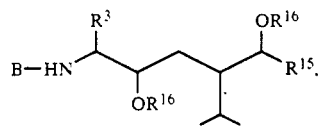  VI

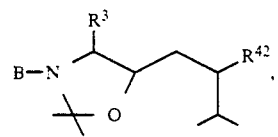

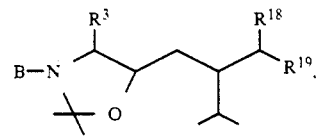  VII

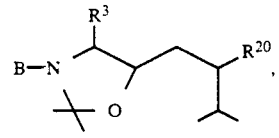

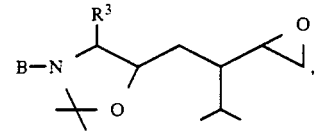

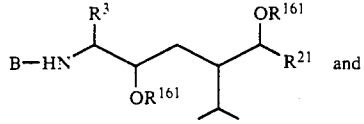 and

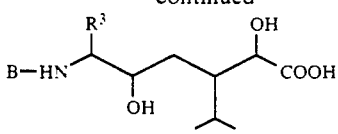

wherein $R^1$ is hydrogen or methyl. $R^2$ is ethyl, propyl, isopropyl, imidazol-2-yl, imidazol-4-yl, pyrazol-3-yl, thiazol-4-yl, thien-2-yl, ethoxycarbonyl, t-butylcarbonylmethyl, benzyloxycarbonylmethyl or t-butoxy, $R^3$ is isobutyl, cyclohexylmethyl or benzyl, A is

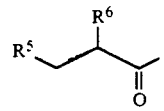

or —Y—Z and $R^4$ is alkanoyl, arylcarbonyl, 2,2-dialkylvinyl, —CH=CH—$R^7$,

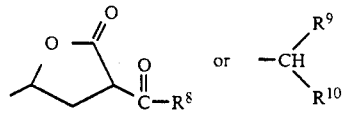

wherein the dotted line can be an additional bond which may or may not be present $R^5$ is phenyl, substituted phenyl, benzyl or naphthyl and $R^6$ is hydrogen, alkoxycarbonylalkyl, alkylcarbonylalkyl, cycloalkylcarbonylalkyl, heterocycloalkylcarbonylalkyl, arylcarbonylalkyl, aminocarbonylalkyl, substituted aminocarbonylalkyl, aminoalkylcarbonylalkyl, substituted aminoalkylcarbonylalkyl, aminoalkylsulphonylalkyl, substituted aminoalkylsulphonylalkyl, alkoxycarbonylhydroxyalkyl, alkylcarbonylhydroxyalkyl, cycloalkylcarbonylhydroxyalkyl, heterocycloalkylcarbonylhydroxyalkyl, arylcarbonylhydroxyalkyl, aminocarbonylhydroxyalkyl, substituted aminocarbonylhydroxyalkyl, dialkoxyphosphoroxyalkyl, diphenyloxyphosphoroxyalkyl, arylalkyl, alkoxycarbonylamino, arylalkoxycarbonylamino, alkylthioalkyl, alkylsulphinylalkyl, alkylsulphonylalkyl, arylthioalkyl, arylsulphinylalkyl, arylsulphonylalkyl, arylalkylthioalkyl, arylalkylsulphinylalkyl or arylalkylsulphonylalkyl, with the proviso that $R^6$ can not be alkoxycarbonylamino or arylalkoxycarbonylamino when $R^5$ is phenyl, benzyl or α-naphthyl, Y is the bivalent residue of optionally N- and/or α-methylated phenylglycine, cyclohexylglycine, phenylalanine, cyclohexylalanine, 4-fluorophenylalanine, 4-chlorophenylalanine, tyrosine, O-methyltyrosine, α-naphthylalanine or homophenylalanine linked with Z at the N-terminal, Z is acyl, $R^7$ is alkyl, aryl, heteroaryl, alkylaminocarbonyl, arylalkylaminocarbonyl or heteroarylalkylaminocarbonyl, $R^8$ is alkoxy, $R^9$ is hydrogen or hydroxy and $R^{10}$ is azidomethyl, —CH=CH—$R^7$, —CH$_2$—O$R^{11}$,

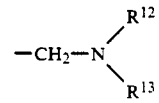

or —(CH$_2$)$_n$—$R^7$ wherein $R^{11}$ is hydrogen, alkyl, arylalkyl, aryl, alkanoyl, arylalkylcarbonyl, heteroarylalkylcarbonyl or alkylcarbamoyl, $R^{12}$ and $R^{13}$ each independently is hydrogen, alkyl, arylalkyl, heteroarylalkyl, aryl, alkanoyl, alkoxycarbonyl, arylalkylcarbonyl, arylalkoxycarbonyl, heteroarylalkylcarbonyl, heterocycloalkylcarbonyl, alkylcarbamoyl or

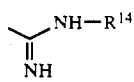

or R$^{12}$ and R$^{13}$ together with the nitrogen atom to which they are attached are a 5- or 6-membered heterocycle or optionally substituted benzimidazolonyl, n is 0, 1 or 2 and R$^{14}$ is hydrogen or arylalkoxycarbonyl, R$^{22}$ is N-protected imidazol-2-yl, imidazol-4-yl or pyrazol-3-yl, B is an amino protecting group, R$^{15}$ is —CH$_2$—OR$^{11}$, alkylaminocarbonylethyl, arylalkylaminocarbonylethyl or heteroarylalkylaminocarbonylethyl and R$^{16}$ is an O-protecting group or R$^{15}$ is alkylaminocarbonyl, arylalkylaminocarbonyl or heteroarylalkylaminocarbonyl and R$^{16}$ is hydrogen and R$^{42}$ is alkanoyl, arylcarbonyl, 2,2-dialkylvinyl —CH=CH—R$^7$,

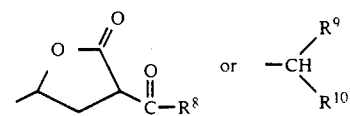

with the proviso that in

R$^9$ is hydrogen when R$^{10}$ is —CH$_2$—OR$^{11}$ or —(CH$_2$)$_n$—R$^7$ in which n is 0 or 2 and R$^7$ is alkylaminocarbonyl, arylalkylaminocarbonyl or heteroarylalkylaminocarbonyl, R$^{18}$ is hydrogen and R$^{19}$ is hydroxymethyl, carboxyl, formyl, 2-ethoxycarbonylvinyl, 2-carboxyvinyl, carboxymethyl or the groups —OX or —CH$_2$OX or R$^{18}$ is hydroxy and R$^{19}$ is cyano or carboxymethyl, R$^{20}$ is 2-ethoxycarbonylvinyl or 2-carboxyvinyl, R$^{21}$ is hydroxymethyl, carboxyl, formyl or the group —CH=CH—R$^{72}$, R$^{161}$ is an O-protecting group, X is p-tolylsulphonyl, methylsulphonyl, trifluoromethylsulphonyl or p-bromobenzenesulphonyl and R$^{72}$ is alkylaminocarbonyl, arylalkylaminocarbonyl or heteroarylalkylaminocarbonyl.

19. A process for the manufacture of a compound in accordance with claim 1, which process comprises a) reacting a compound of the general formula

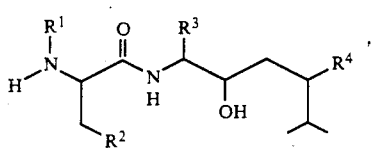

wherein R$^1$, R$^2$, R$^3$ and R$^4$ have the significance given in claim 1, with an acylating agent yielding the group

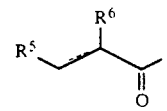

or

wherein R$^5$, R$^6$, Y, Z and the dotted line have the significance given in claim 1, or b) reacting a compound of the general formula

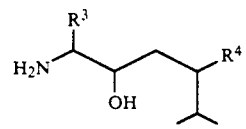

wherein R$^3$ and R$^4$ have the significance given in claim 1, with a compound of the general formula

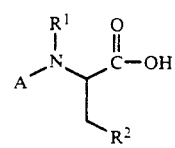

wherein R$^1$, R$^2$ and A have the significance given in claim 1, or an activated derivative thereof, or c) reacting a compound corresponding to formula I, but in which Z is hydrogen and the remaining symbols have the significance given in claim 1 with an acylated amino acid or an acylated dipeptide, or d) for the manufacture of a compound of formula I in which R$^2$ is imidazol-2-yl, imidazol-4-yl or pyrazol-3-yl and/or R$^{12}$ is hydrogen, cleaving off the N-protecting group and/or the substituent R$^{12}$ from a compound of the general formula

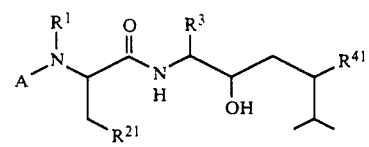

wherein R$^{21}$ is ethyl, propyl, isopropyl, thiazolyl-4-yl, thien-2-yl, ethoxycarbonyl, t-butyl-carbonylmethyl, benzyloxycarbonylmethyl, t-butoxy or optionally N-protected imidazol-2-yl, imidazol-4-yl or pyrazol-3-yl and R$^{41}$ is alkanoyl, arylcarbonyl, 2,2-dialkylvinyl, —CH=CH—R$^7$,

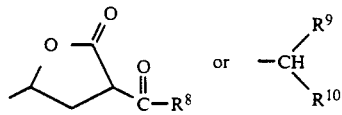

in which R$^7$ is aryl, heteroaryl, alkylaminocarbonyl, arylalkylaminocarbonyl or heteroarylalkylaminocarbonyl, R$^8$ is alkoxy, R$^9$ is hydrogen or hydroxy and R$^{10}$ is azidomethyl, —CH=CH—R$^7$, —CH$_2$—OR$^{11}$,

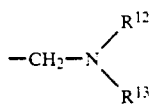

or $-(CH_2)_n-R^7$ in which $R^{11}$ is hydrogen, alkyl, arylalkyl, aryl, alkanoyl, arylalkylcarbonyl, heteroarylalkylcarbonyl or alkylcarbamoyl, $R^{12}$ and $R^{13}$ each independently is hydrogen, alkyl, arylalkyl, heteroarylalkyl, aryl, alkanoyl, alkoxycarbonyl, arylalkylcarbonyl, arylalkoxycarbonyl, heteroarylalkylcarbonyl, heterocycloalkylcarbonyl, alkylcarbamoyl or

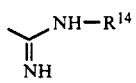

or $R^{12}$ and $R^{13}$ together with the nitrogen atom to which they are attached are a 5- or 6-membered heterocycle or optionally substituted benzimidazolonyl, n is O, 1 or 2 and $R^{14}$ is hydrogen or arylalkoxycarbonyl, and the remaining symbols have the significance given in claim 1, with the proviso that $R^{21}$ is N-protected imidazol-2-yl, imidazol-4-yl or pyrazol-3-yl and/or $R^{41}$ is

in which $R^{10}$ is

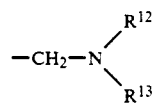

and $R^{12}$ is readily cleavable arylalkyl, alkoxycarbonyl or arylalkoxycarbonyl, and e) if desired, separating a mixture of diastereomeric racemates into the diastereomeric racemates or optically pure diastereomers, and/or f) if desired, separating a mixture of diastereomers into the optically pure diastereomers, and/or g) if desired, converting a compound obtained into a pharmaceutically usable salt.

20. A compound composition for the control or prevention of high blood pressure and cardiac insufficiency, containing an amino acid derivative as recited in claim 1 and a physiologically acceptable carrier.

21. A process for treating high blood pressure and cardiac insufficiency comprising administering a therapeutically effective amount of an amino acid derivative as recited in claim 1 and a physiologically acceptable carrier.

* * * * *

UNITED STATES PATENT AND TRADEMARK OFFICE
CERTIFICATE OF CORRECTION

PATENT NO. : 5,140,011

DATED : August 18, 1992

INVENTOR(S) : Quirico Branca, Hans Peter Marki, Werner Neidhart
Henri Ranuz, Wolfgang Wostl It is certified that error appears in the above-identified patent and that said Letters Patent is hereby corrected as shown below:

In claim 20, column 64, line 24, before "composition", delete "compound"

Signed and Sealed this

Twelfth Day of October, 1993

Attest:

BRUCE LEHMAN

*Attesting Officer*  *Commissioner of Patents and Trademarks*